US012767965B2

(12) United States Patent
Geissler et al.

(10) Patent No.: US 12,767,965 B2
(45) Date of Patent: Oct. 20, 2026

(54) METHODS FOR THE BIOTECHNOLOGICAL PRODUCTION OF ALDEHYDE MIXTURES

(71) Applicant: SYMRISE AG, Holzminden (DE)

(72) Inventors: Torsten Geissler, Einbeck (DE); Jakob Peter Ley, Holzminden (DE); Michael Backes, Holzminden (DE); Christoph Harms, Holzminden (DE); Uwe Bornscheuer, Greifswald (DE); Kathleen Balke, Greifswald (DE); Holger Zorn, Wettenberg (DE); Marco Alexander Fraatz, Gießen (DE); Andreas Hammer, Bad Nauheim (DE)

(73) Assignee: SYMRISE AG, Holzminden (DE)

( * ) Notice: Subject to any disclaimer, the term of this patent is extended or adjusted under 35 U.S.C. 154(b) by 877 days.

(21) Appl. No.: 17/910,649

(22) PCT Filed: Mar. 12, 2020

(86) PCT No.: PCT/EP2020/056678

§ 371 (c)(1),
(2) Date: Sep. 9, 2022

(87) PCT Pub. No.: WO2021/180327

PCT Pub. Date: Sep. 16, 2021

(65) Prior Publication Data

US 2023/0407349 A1 Dec. 21, 2023

(51) Int. Cl.

| | |
|---|---|
| ***C12P 7/40*** | (2006.01) |
| ***C12N 15/63*** | (2006.01) |
| ***C12P 7/24*** | (2006.01) |

(52) U.S. Cl.

CPC ................ *C12P 7/40* (2013.01); *C12N 15/63* (2013.01); *C12P 7/24* (2013.01); *C12Y 102/01003* (2013.01); *C12Y 113/11* (2013.01)

(58) Field of Classification Search

None

See application file for complete search history.

(56) References Cited

U.S. PATENT DOCUMENTS

| | | | | |
|---|---|---|---|---|
| 10,017,790 | B2 * | 7/2018 | Sporleder | C12P 7/24 |
| 10,767,198 | B2 * | 9/2020 | Fraatz | C12N 9/0083 |
| 2013/0149756 | A1 | 6/2013 | Sporleder et al. | |
| 2019/0367954 | A1 * | 12/2019 | Fraatz | C07C 45/27 |

FOREIGN PATENT DOCUMENTS

| | | | |
|---|---|---|---|
| JP | 63233914 | A | 9/1988 |
| JP | 05000974 | A | 8/2012 |
| JP | 2014043409 | A | 3/2014 |
| JP | 2019-500861 | A | 1/2019 |
| WO | 2012025629 | A1 | 3/2012 |

OTHER PUBLICATIONS

Chica et al. Curr Opin Biotechnol. Aug. 2005; 16(4):378-84. (Year: 2005).*

Singh et al. Curr Protein Pept Sci. 2017, 18, 1-11 (Year: 2017).*

Accession AZT69170. Apr. 12, 2012 (Year: 2012).*

Accession Q56694. Jun. 20, 2001 (Year: 2001).*

Accession ADJ56682. May 6, 2004 (Year: 2004).*

International Searching Authority (ISA/EP). International Search Report and Written Opinion, issued in PCT Application No. PCT/EP2020/056678 on Feb. 1, 2021. 21 pages, including English translation of International Search Report.

Buchhaupt, Markus et al. "Oxidation of fatty aldehydes to fatty acids by *Escherichia coli* cells expressing the Vibrio harveyi fatty aldehyde dehydrogenase (FALDH)." World Journal of Microbiology and Biotechnology 29.3 (2013): 569-575.

Maurer, Susanne et al. "Investigation of fatty aldehyde and alcohol synthesis from fatty acids by αDox-or CAR-expressing *Escherichia coli*." Journal of biotechnology 305 (2019): 11-17.

Hamberg, Mats et al. "Fatty acid α-dioxygenases." Prostaglandins & other lipid mediators 68 (2002): 363-374.

Akakabe, Yoshihiko, et al. "Concise synthesis of (8Z, 11Z, 14Z)-8, 11, 14-heptadecatrienal,(7Z, 10Z, 13Z)-7, 10, 13-hexadecatrienal, and (8Z, 11Z)-8, 11-heptadecadienal, components of the essential oil of marine green alga Ulva pertusa." Bioscience, biotechnology, and biochemistry 69.7 (2005): 1348-1352.

Ishige, Takeru, et al. "Long-chain aldehyde dehydrogenase that participates in n-alkane utilization and wax ester synthesis in *Acinetobacter* sp. strain M-1." Applied and environmental microbiology 66.8 (2000): 3481-3486.

Kato, Tomohisa, et al. "Gene cloning and characterization of an aldehyde dehydrogenase from long-chain alkane-degrading Geobacillus thermoleovorans B23." Extremophiles 14.1 (2010): 33-39.

Fujimura, T., & Kajiwara, T. (1990). Production of bioflavor by regeneration from protoplasts of Ulva pertusa (Ulvales, Chlorophyta). Hydrobiologia, 204-205(1), 143-149. doi:10.1007/bf00040226.

Hasan, Fariha, Aamer Ali Shah, and Abdul Hameed. "Industrial applications of microbial lipases." Enzyme and Microbial technology 39.2 (2006): 235-251.

Smith, Temple F., and Michael S. Waterman. "Identification of common molecular subsequences." Journal of molecular biology 147.1 (1981): 195-197.

Notice of Reasons for Rejection for Japanese application No. 2022-554676, Jan. 15, 2024.

Buchhaupt, Markus et al. "Oxidation of fatty aldehydes to fatty acids by *Escherichia coli* cells expressing the Vibrio harveyi fatty aldehyde dehydrogenase (FALDH)," World J Microbiol Biotechnol (2013) 29:569-575. Nov. 21, 2012.

(Continued)

*Primary Examiner* — Christian L Fronda

(74) *Attorney, Agent, or Firm* — Meunier Carlin & Curfman LLC

(57) ABSTRACT

The present invention relates to biotechnological methods for the production of saturated as well as unsaturated aldehydes, and mixtures thereof using at least one alpha-dioxygenase and at least one aldehyde dehydrogenase. The method may be carried out either fermentatively or enzymatically. Furthermore, the present invention relates to a vector system, as well as sequences and recombinant microorganisms encoding the enzymes that can be used to produce the aldehydes and mixtures according to the invention. Further, the present invention relates to compositions obtained by the methods according to the present invention.

11 Claims, 7 Drawing Sheets

Specification includes a Sequence Listing.

(56) References Cited

OTHER PUBLICATIONS

Kaehne, Fenja et al. "A recombinant alpha-dioxygenase from rice to produce fatty aldehydes using *E. coli*," Appl Microbiol Biotechnol (2011) 90:989 995, Feb. 24, 2011.
Maurer, Susanne et al. "Investigation of fatty aldehyde and alcohol synthesis from fatty acides by alphaDox- or CAR-expressing *Escherichia coli*," Journal of Biology 305 (2019) 11-17, Aug. 17, 2019.
Hamberg, Mats et al. "Fatty acid alpha-dioxygenases," Prostaglandins & other Lipids Mediators 68-69 (2002) 363-274.

* cited by examiner

METHODS FOR THE BIOTECHNOLOGICAL PRODUCTION OF ALDEHYDE MIXTURES

REFERENCE TO AN ELECTRONIC SEQUENCE LISTING

The content of the electronic sequence listing submitted on Mar. 22, 2023, as a text file named "SM_5974-05US_11463-009US1" created on Feb. 8, 2023, and having a size of 228 KB, is herein incorporated by reference in its entirety pursuant to 37 C.F.R. § 1.52 (e) (5).

TECHNICAL FIELD

The present invention relates to biotechnological methods for the production of saturated and unsaturated aldehydes, as well as mixtures thereof, using at least one alpha-dioxygenase and at least one aldehyde dehydrogenase. The method may be carried out either fermentatively or enzymatically. Furthermore, the present invention relates to a vector system, as well as sequences and recombinant microorganisms encoding the enzymes that can be used to produce the aldehydes and mixtures according to the invention. Further, the present invention relates to compositions obtained by the methods according to the present invention.

BACKGROUND OF THE INVENTION

In the field of industrial production of flavors, there is a constant need for efficient and cost-effective ways of synthesizing flavors. An example of such flavors are (un) saturated aldehydes. An exemplary aldehyde is 8Z-tetradecenal or 1-decenal. This class of substances is mainly found in meat preparations and citrus oils. At present, however, no generally applicable biotechnological process for the production of these aldehydes and the corresponding acids has been described.

Processes for the preparation of unsaturated aldehydes are known from the prior art. For example, 8Z,11Z-heptadecadienal can be obtained by the chemical oxidation of the unsaturated alcohol (JP 63233914). Various aldehydes can also be produced in a known manner from fatty acids by alpha-oxidation using plant enzymes, as described in WO2012025629 A1. The use of algal biomass to produce unsaturated aldehydes is also known ("*Concise synthesis of* (*8Z,11Z,14Z*)-8,11,14-*heptadecatrienal*, (*7Z,10Z,3Z*)-7,10,13-*hexadecatrienal, and* (*8Z11Z*)-8,11-*heptadecadienal, components of the essential oil of marine green alga Ulva pertusa,*" Biosci Biotechnol Biochem. 2005 July; 69(7): 1348-52). Furthermore, processes for the preparation of 4,7,10,13,16-nonadecapentaenal or 3,6,9,12,15,18-heneicosahexaenal are known (Preparation of halopolyenes and their intermediates, JP05000974A).

Furthermore, numerous processes using aldehyde dehydrogenases are known to oxidize aldehydes to acids (Takeru Ishige et al., *Appl. Environ. Microbiol.* 2000, 66, 3481-3486; Tomohisa Kato et al., *Extremophiles* 2010, 14, 33.).

The above-mentioned chemical methods as well as methods based exclusively on the use of a very special enzyme alone have the disadvantage, however, that no comprehensive spectrum of aldehydes or mixtures thereof is accessible. Furthermore, some of the methods are based on the reaction with chemical reagents as well as catalysts, which is why such methods are not considered natural processes in the sense of EC 1334/2008. A combined method that specifically combines an alpha-dioxygenase with an aldehyde dehydrogenase and specifically expands the production spectrum is not known. In a recombinant reaction system with two or more enzymes, where the desired catalytic reactions are to proceed sequentially and specifically with respect to substrate specificity and selectivity, it is necessary to precisely match the enzymes used so that they are not interfered with by, for example in the case of whole-cell catalysis, endogenous enzymes of the production organism. The reaction control is therefore crucial to ensure that the intermediates are also recognized by the second or respective next enzyme in the cascade and are available for the latter. Such coordination or combination is always technically challenging and cannot be predicted in a straight line, but rather requires intensive analyses on the enzymes of interest in the respective biotechnological context.

The natural occurrence of some unsaturated aldehydes with one or more double bonds such as 8Z-heptadecenal, 8Z,11Z-heptadecadienal or 8Z,11Z,14Z-heptadecatrienal has been reported in pressed juices of cucumber (*Cucumber Aroma formation of cucumber* (*Cucumis sativus* L.) *and bitter gourd* (*Momordica charantia* L.) *by salt-squeezing, Journal of Home Economics of Japan Vol.* 60 (2009) *No.* 10 p. 877-885) or the alga *Ulva pertusa* (*Production of bioflavor by regeneration from protoplasts of Ulvapertusa* (*Ulvales, Chlorophyta*) *Hydrobiologia,* 1990, *Vol.* 204, pp 143-149). The content of the aldehydes 8Z-heptadecenal, 8Z,11Z-heptadecadienal, 8Z,11Z,14Z-heptadecatrienal is reported in the literature as 2%, 19.9% and 26.1%.

The odor of 8Z,11Z-heptadecadienal is described as typical of algae (*Production of bioflavor by regeneration from protoplasts of Ulva pertusa* (*Ulvales, Chlorophyta*), *Hydrobiologia,* 1990, *Vol.* 204, pp 143-149).

In contrast, the taste of 4Z,7Z,10Z,13Z-nonadecatetraenal, 4Z,7Z,10Z,13Z,16Z-nonadecapentaenal, or 3,6,9,12,15,18-heneicosahexaenoic acid has not been described.

8Z-pentadecenal is known to be a naturally occurring constituent of cucumber (Kemp, *A C15 aldehyde from Cucumis sativus, Phytochemistry, Volume* 16, *Issue* 11, 1977, Pages 1831-1832). The flavor of 8Z-pentadecenal is described primarily as oily, and flavor-enhancing properties on chicken and grilled beef are also described. Furthermore, a method for the production from 1-nonine and 6-bromo-1-hexanol is known, but this cannot be classified as a natural production process according to EC 1334/2008 (JP 2014043409).

The taste of 4Z,7Z,10Z,13Z-nonadecatetraenal is not known and no manufacturing methods existed until now.

Various aldehydes can be produced from fatty acids by alpha-oxidation using plant enzymes, as described in WO2012025629 A1. The use of algal biomass for the production of unsaturated aldehydes is also known.

Other processes for the production of fatty acids from the corresponding oils or fats by enzymatic cleavage are also known from the prior art. Bacterial lipases such as enzymes from *Aspergillus niger, Rhizopus oryzae, Penicillium camembertii, Mucor juvanicus, Penicillium roquefortii*, porcine pancreas, *Candida rugosa, Rhizomucor miehei, Candida antarctica* or *Rhizops delemar* are mainly used for this purpose (*Industrial applications of microbial lipases, Enzyme and Microbial Technology Volume* 39, *Issue* 2, 26 Jun. 2006, Pages 235-251).

It was therefore an object of the present invention to provide a method for the production of aldehydes or aldehyde mixtures which can be classified as a natural production process according to EC 1334/2008. Furthermore, it was an object to provide an integrated biotechnological process by selective tuning of enzymatic metabolic steps, which can provide the products of interest in high yield and purity without intermediate chemical steps.

SUMMARY OF THE INVENTION

Accordingly, in accordance with a primary aspect, the present invention relates to providing a method for producing saturated and unsaturated aldehydes using at least one alpha-dioxygenase and at least one aldehyde dehydrogenase.

Furthermore, according to one embodiment, the present invention relates to a fermentative method for the production of saturated and unsaturated aldehydes and mixtures thereof. In another embodiment of the method according to the present invention, an enzymatic method is provided.

In a further embodiment, the method according to the present invention relates to the use of reactants (educts) which are either of biotechnological, natural or chemical origin.

In yet another embodiment, the method according to the invention relates to preferred reactants selected from the group of carboxylic acids and carboxylic acids esterified with alcohols.

Furthermore, the method according to the invention relates to preferred product mixtures, microorganisms used in the method as well as amino acid sequences of the enzymes to be preferably used and nucleotide sequences or nucleic acid segments coding for the enzymes to be used.

Another aspect of the present invention relates to the provision of a vector system encoding the enzymes used according to the invention.

Another aspect of the present invention relates to a composition obtained by a method according to the invention.

BRIEF DESCRIPTION OF THE SEQUENCES

Figure 1:
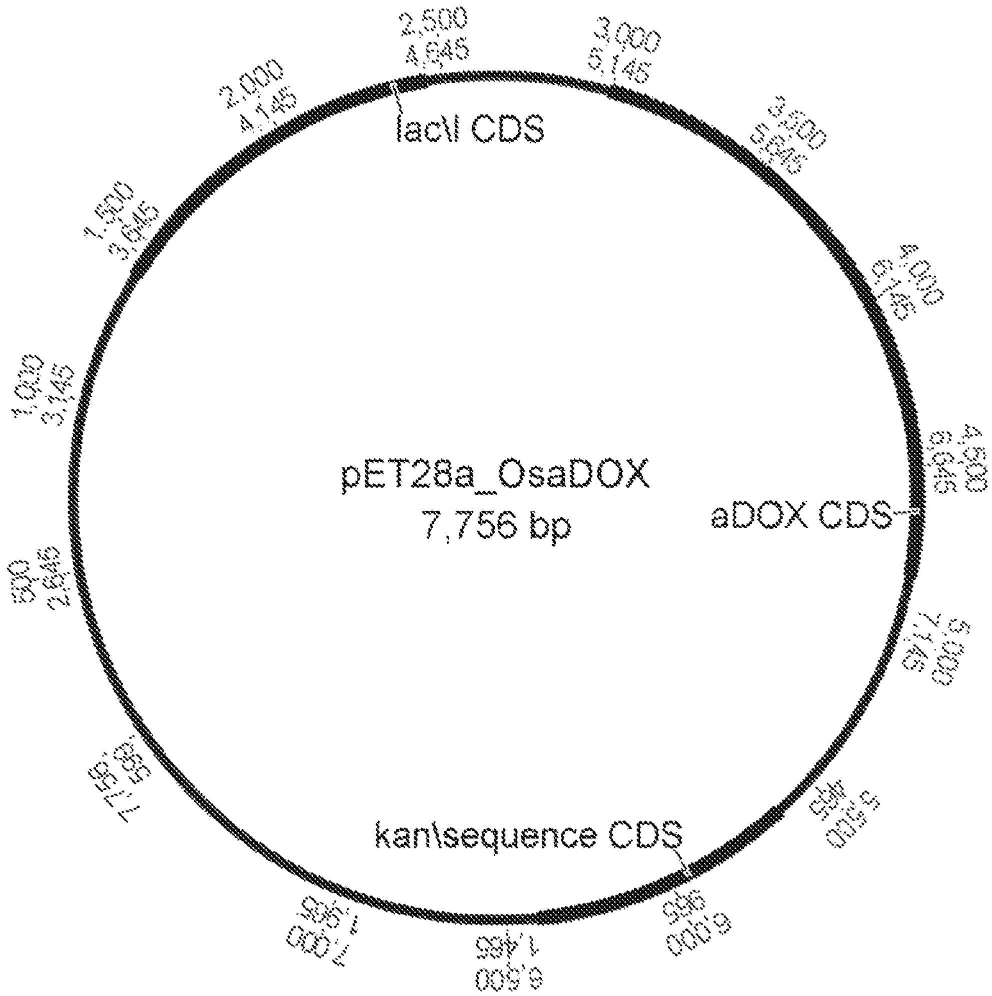
FIG. 1: Plasmid pET28a_OSaDOX with genes encoding an alpha-dioxygenase.
Figure 2:
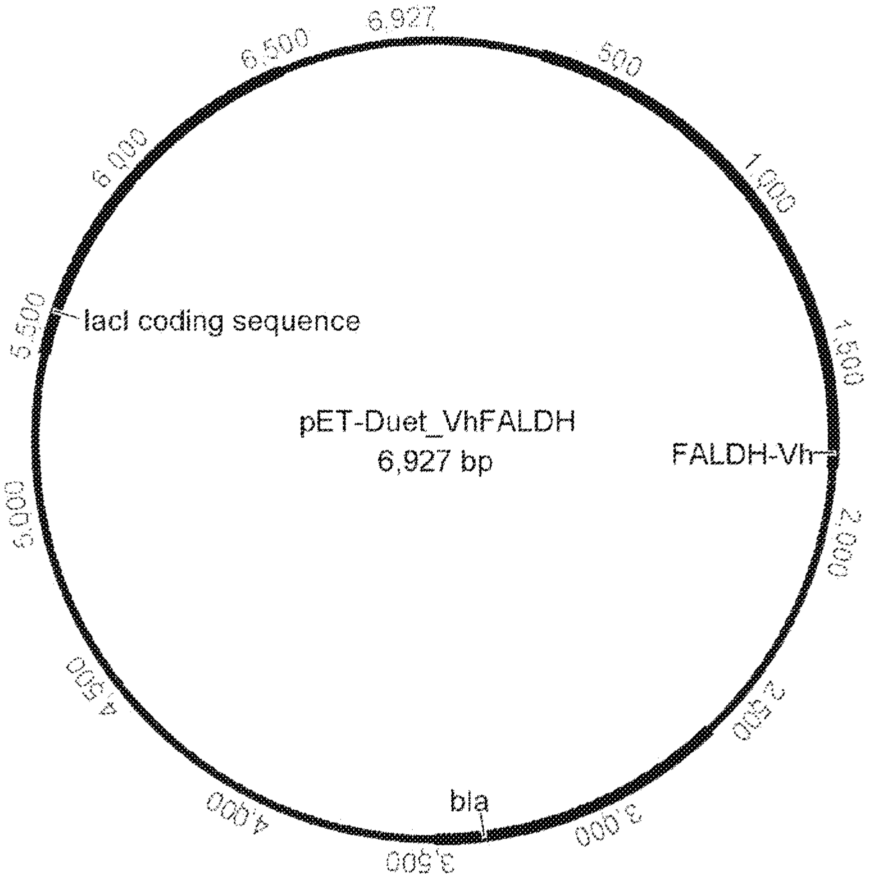
FIG. 2: Plasmid pET-Duet_VhFALDH with genes encoding an aldehyde dehydrogenase.
Figure 3:
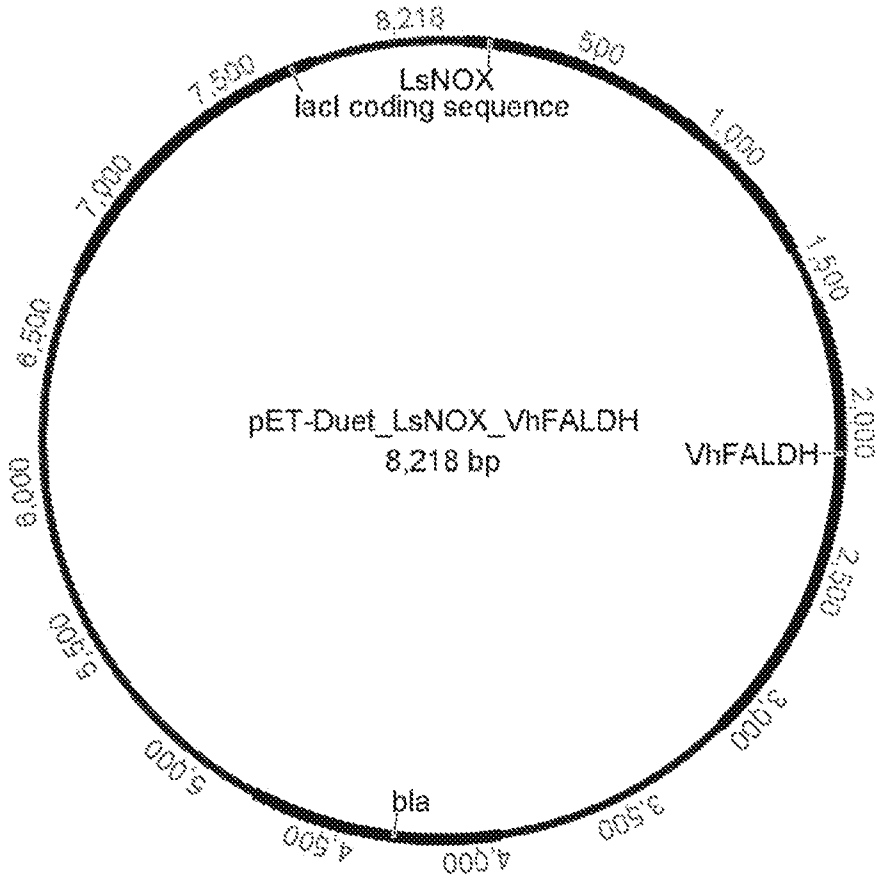
FIG. 3: Plasmid pET-Duet_LsNOX_VhFALDH with genes encoding an aldehyde dehydrogenase and an $NADH^-$ oxidase.
Figure 4:
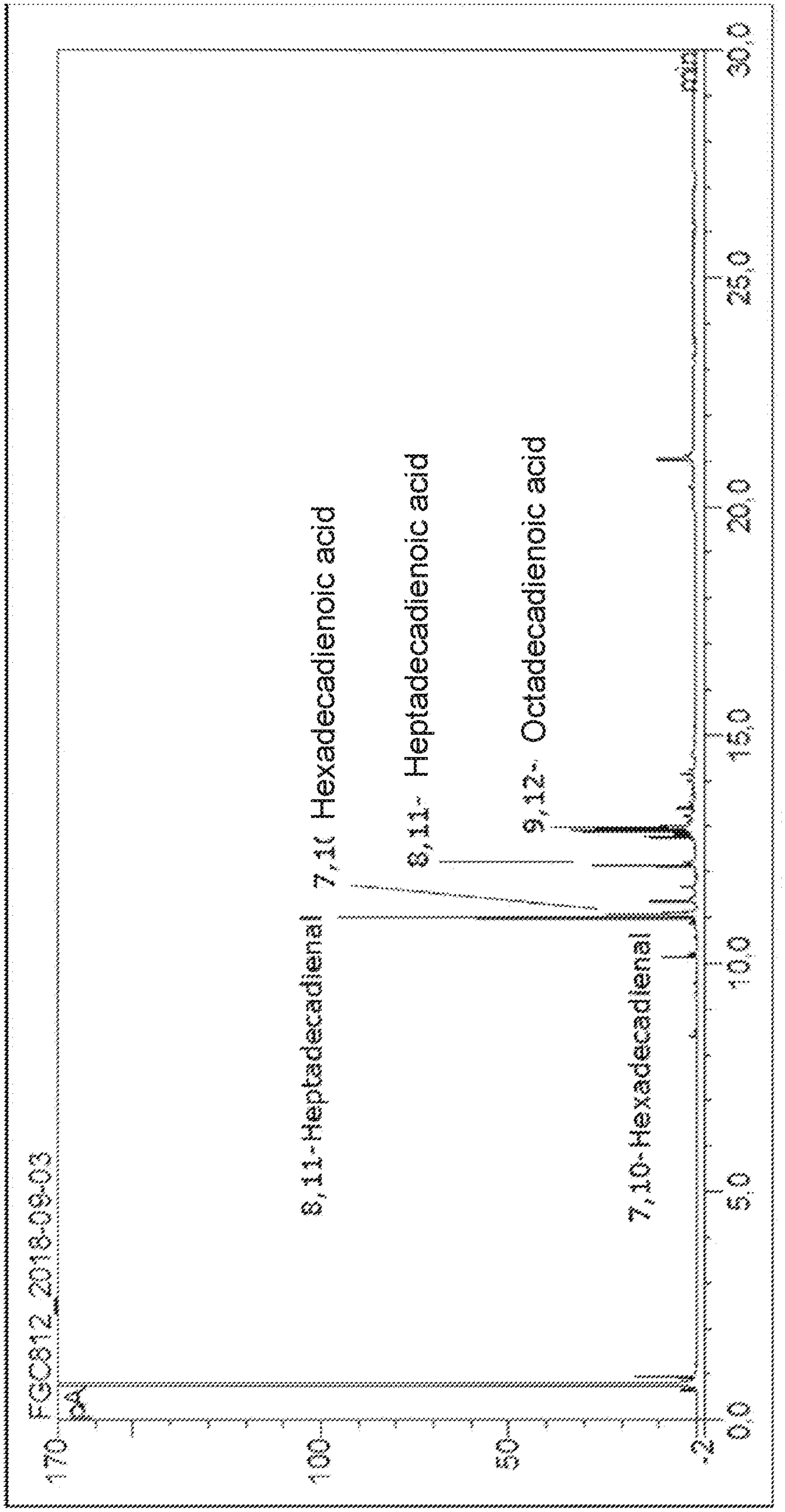
FIG. 4: Biocatalytic conversion of a mixture of oleic acid and linoleic acid to an aldehyde mixture containing 8,11-heptadecadienal and 7,10-hexadecadienal.
Figure 5:
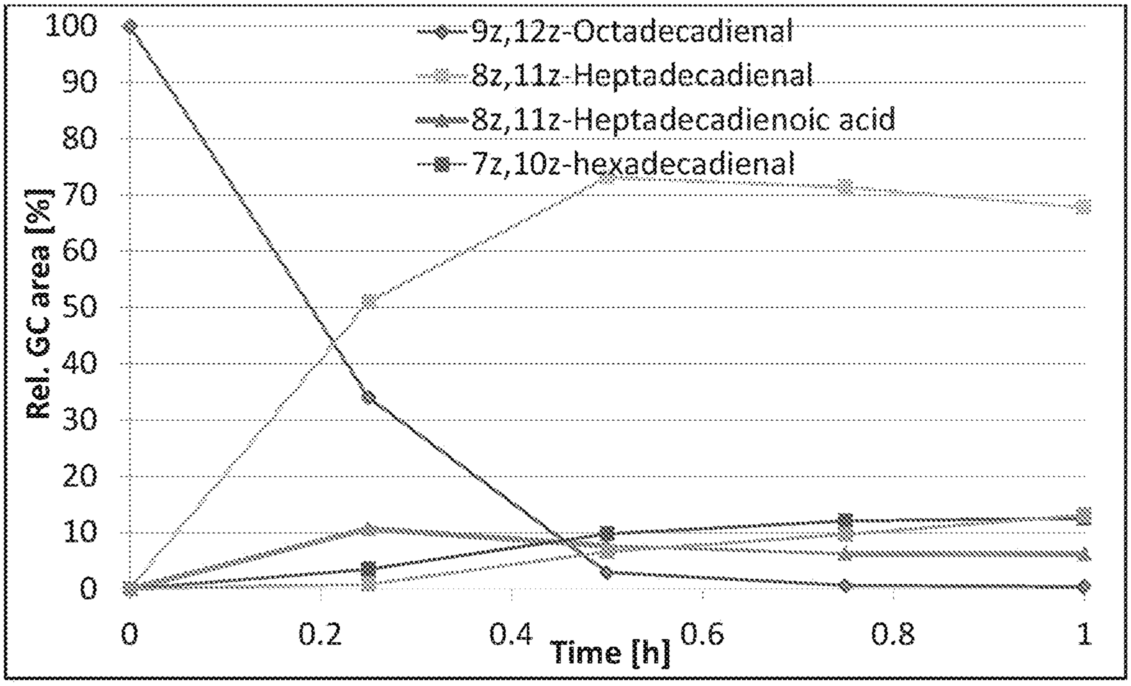
FIG. 5: Time course of a biocatalytic conversion of a mixture of oleic acid and linoleic acid by alpha-dioxygenase, aldehyde dehydrogenase and NADH oxidase to a corresponding aldehyde mixture within one hour.
Figure 6:
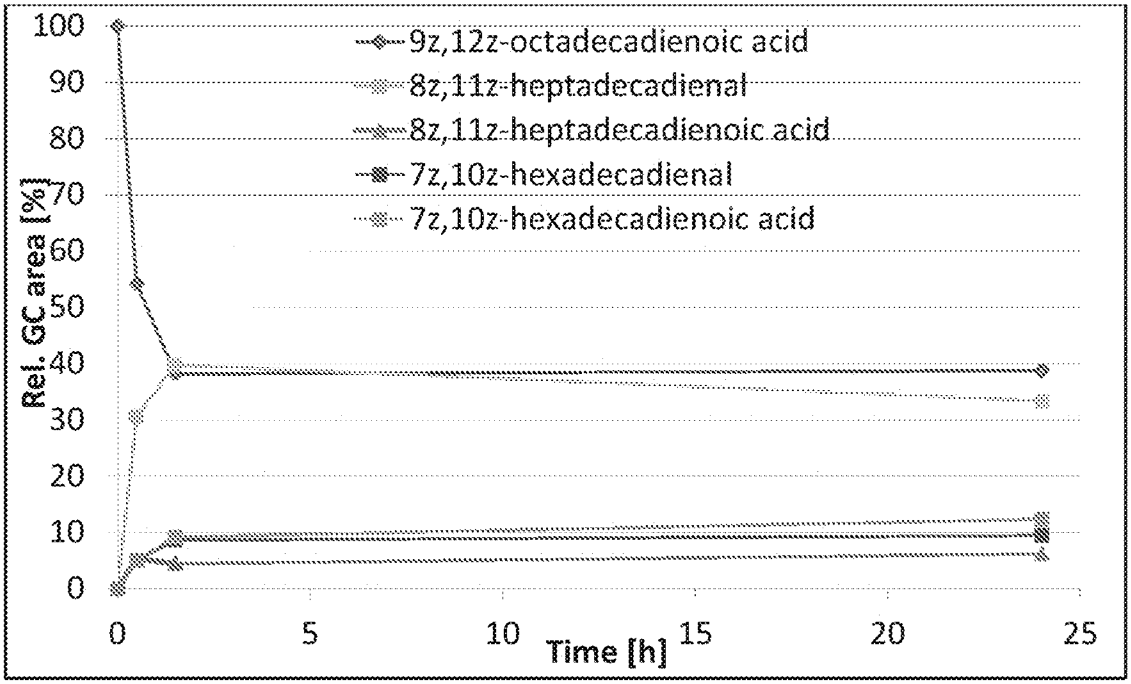
FIG. 6: Time course of a biocatalytic conversion of a mixture of oleic acid and linoleic acid by alpha-dioxygenase and aldehyde dehydrogenase without NADH oxidase to a corresponding aldehyde mixture within 24 hours.
Figure 7:
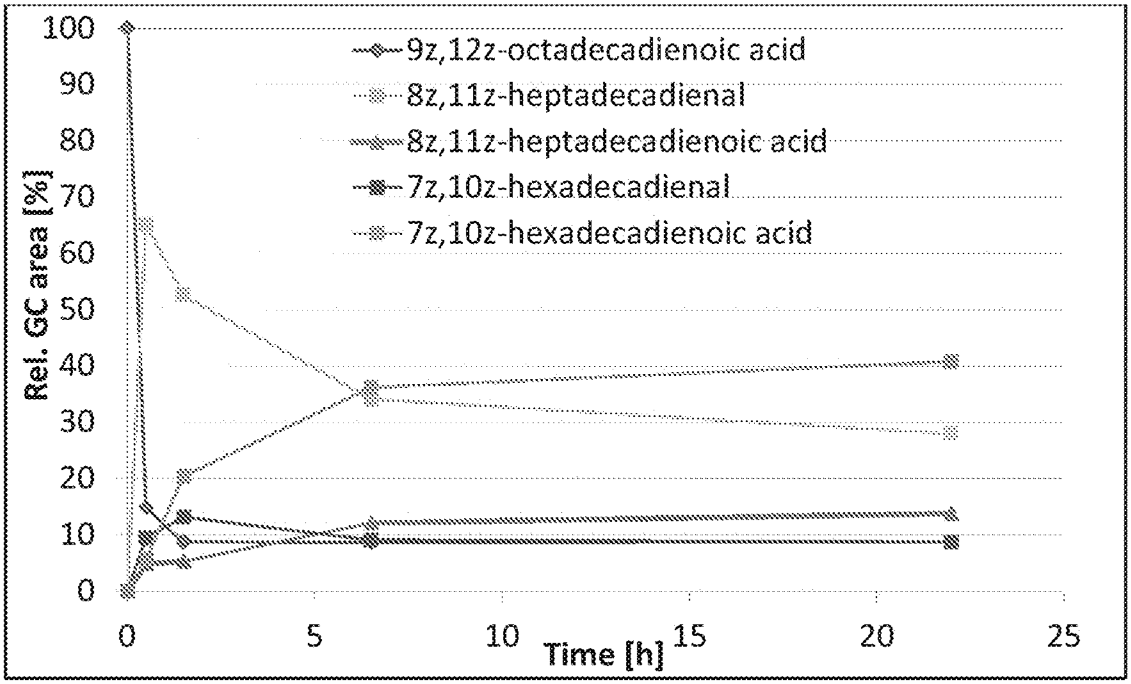
FIG. 7: Increased time course of a biocatalytic conversion of a mixture of oleic acid and linoleic acid by alpha-dioxygenase and aldehyde dehydrogenase with NADH oxidase to a corresponding aldehyde mixture within 24 hours.

SEQ ID NO 1: Nucleic acid sequence encoding the enzyme Os-alpha-DOX from *Oryza sativa.*

SEQ ID NO 2: Nucleic acid sequence encoding the enzyme VhFALDH from *Vibrio harveyi.*

SEQ ID NO 3: Nucleic acid sequence encoding the 175Q mutant of the enzyme VhFALDH from *Vibrio harveyi.*

SEQ ID NO 4: Nucleic acid sequence encoding the enzyme LsNOX from *Lactobacillus sanfranciscenis.*

SEQ ID NO 5: Nucleic acid sequence encoding the enzyme ReALDH from *Rhodococcus erythropolis* UPV-1.

SEQ ID NO 6: Nucleic acid sequence encoding the enzyme GtALDH from *Geobacillus thermodenitrificans.*

SEQ ID NO 7: Nucleic acid sequence encoding the enzyme Maqu3410, an aldehyde dehydrogenase from *Marinobacter aquaeolei* VT8.

SEQ ID NO 8: Amino acid sequence encoding the enzyme Os-alpha-DOX from *Oryza sativa.*

SEQ ID NO 9: Amino acid sequence encoding the enzyme VhFALDH from *Vibrio harveyi.*

SEQ ID NO 10: Amino acid sequence encoding the 175Q mutant of the enzyme VhFALDH from *Vibrio harveyi.*

SEQ ID NO 11: Amino acid sequence encoding the enzyme LsNOX from *Lactobacillus sanfranciscenis.*

SEQ ID NO 12: Amino acid sequence encoding the enzyme ReALDH from *Rhodococcus erythropolis* UPV-1.

SEQ ID NO 13: Amino acid sequence encoding the enzyme GtALDH from *Geobacillus thermodenitrificans.*

SEQ ID NO 14: Amino acid sequence encoding the enzyme Maqu3410, an aldehyde dehydrogenase from *Marinobacter aquaeolei* VT8.

SEQ ID NO 15: Nucleic acid sequence encoding a forward primer.

SEQ ID NO 16: Nucleic acid sequence encoding a reverse primer.

SEQ ID NO 17: Nucleic acid sequence encoding the enzyme At-alpha-DOX from *Arabidopsis thaliana.*

SEQ ID NO 18: Nucleic acid sequence encoding the enzyme At-alpha-DOX from *Arabidopsis thaliana.*

SEQ ID NO 19: Nucleic acid sequence encoding the enzyme CaaDOX from *Capsicum annuum.*

SEQ ID NO 20: Nucleic acid sequence encoding the enzyme CbaDOX from *Cercospora beticola.*

SEQ ID NO 21: Nucleic acid sequence encoding the enzyme CsaDOX2 from *Cucumis sativus.*

SEQ ID NO 22: Nucleic acid sequence encoding the enzyme CsaDOX from *Cucumis sativus.*

SEQ ID NO 23: Nucleic acid sequence encoding the enzyme CsaDOxlike1 from *Cucumis sativus.*

SEQ ID NO 24: Nucleic acid sequence encoding the enzyme Le-alpha-DOX1 from *Solanum lycopersicum.*

SEQ ID NO 25: Nucleic acid sequence encoding the enzyme Le-alpha-DOX2 from *Solanum lycopersicum.*

SEQ ID NO 26: Nucleic acid sequence encoding the enzyme NaaDOX2 from *Nicotiana attenuata.*

SEQ ID NO 27: Nucleic acid sequence encoding the enzyme Na-alpha-DOX from *Nicotiana attenuata.*

SEQ ID NO 28: Nucleic acid sequence encoding the enzyme Nt-alpha-DOX from *Nicotiana tabacum.*

SEQ ID NO 29: Nucleic acid sequence encoding the enzyme PpaDOX from *Physcomitrella patens.*

SEQ ID NO 30: Nucleic acid sequence encoding the enzyme Ps-alpha-DOX from *Pisum sativum.*

SEQ ID NO 31: Nucleic acid sequence encoding the enzyme StaDOX2 from *Solanum lycopersicum.*

SEQ ID NO 32: Nucleic acid sequence encoding the enzyme StaDOX1.1 from *Solanum lycopersicum.*

SEQ ID NO 33: Nucleic acid sequence encoding the enzyme StaDOX1.2 from *Solanum lycopersicum.*

SEQ ID NO 34: Nucleic acid sequence encoding the enzyme StaDOX1.3 from *Solanum lycopersicum.*

SEQ ID NO 35: Nucleic acid sequence encoding the enzyme StaDOX1 from *Solanum tuberosum.*

SEQ ID NO 36: Nucleic acid sequence encoding the enzyme StaDOX2 from *Solanum tuberosum.*

SEQ ID NO 37: Amino acid sequence encoding the enzyme At-alpha-DOX2 from *Arabidopsis thaliana.*

SEQ ID NO 38: Amino acid sequence encoding the enzyme At-alpha-DOX from *Arabidopsis thaliana.*

SEQ ID NO 39: Amino acid sequence encoding the enzyme CaaDOX from *Capsicum annuum.*

SEQ ID NO 40: Amino acid sequence encoding the enzyme CbaDOX from *Cercospora beticola.*

SEQ ID NO 41: Amino acid sequence encoding the enzyme CsaDOX2 from *Cucumis sativus.*

SEQ ID NO 42: Amino acid sequence encoding the enzyme CsaDOX from *Cucumis sativus.*

SEQ ID NO 43: Amino acid sequence encoding the enzyme CsaDOxlike1 from *Cucumis sativus.*

SEQ ID NO 44: Amino acid sequence encoding the enzyme Le-alpha-DOX1 from *Solanum lycopersicum.*

SEQ ID NO 45: Amino acid sequence encoding the enzyme Le-alpha-DOX2 from *Solanum lycopersicum.*

SEQ ID NO 46: Amino acid sequence encoding the enzyme NaaDOX2 from *Nicotiana attenuata.*

SEQ ID NO 47: Amino acid sequence encoding the enzyme Na-alpha-DOX from *Nicotiana attenuata.*

SEQ ID NO 48: Amino acid sequence encoding the enzyme Nt-alpha-DOX from *Nicotiana tabacum.*

SEQ ID NO 49: Amino acid sequence encoding the enzyme PpaDOX from *Physcomitrella patens.*

SEQ ID NO 50: Amino acid sequence encoding the enzyme Ps-alpha-DOX from *Pisum sativum.*

SEQ ID NO 51: Amino acid sequence encoding the enzyme StaDOX2 from *Solanum lycopersicum.*

SEQ ID NO 52: Amino acid sequence encoding the enzyme StaDOX1.1 from *Solanum lycopersicum.*

SEQ ID NO 53: Amino acid sequence encoding the enzyme StaDOX1.2 from *Solanum lycopersicum.*

SEQ ID NO 54: Amino acid sequence encoding the enzyme StaDOX1.3 from *Solanum lycopersicum.*

SEQ ID NO 55: Amino acid sequence encoding the enzyme StaDOX1 from *Solanum tuberosum.*

SEQ ID NO 56: Amino acid sequence encoding the enzyme StaDOX2 from *Solanum tuberosum.*

SEQ ID NO 57: Nucleic acid sequence encoding the enzyme Ald1 from *Acinetobacter* sp. strain M1.

SEQ ID NO 58: Nucleic acid sequence encoding the enzyme HFD4, an aldehyde dehydrogenase from *Yarrowia lipolytica.*

SEQ ID NO 59: Amino acid sequence encoding the enzyme Ald1 from *Acinetobacter* sp. strain M1.

SEQ ID NO 60: Amino acid sequence encoding the enzyme HFD4, an aldehyde dehydrogenase from *Yarrowia lipolytica.*

SEQ ID NO 61: Nucleic acid sequence encoding an NAD(P)H oxidase from *Lactobacillus sanfranciscensis.*

SEQ ID NO 62: Amino acid sequence encoding an NAD(P)H oxidase from *Lactobacillus sanfranciscensis.*

SEQ ID NO 63: Nucleic acid sequence encoding an NADH oxidase from *Lactobacillus brevis.*

SEQ ID NO 64: Amino acid sequence encoding an NADH oxidase from *Lactobacillus brevis.*

DEFINITIONS

The term vector system as used herein means a system consisting of or containing at least one or more vectors or plasmid vectors. Thus, a vector system may include a (plasmid) vector encoding multiple different target genes. A vector system may further comprise multiple (plasmid) vectors, which in turn comprise at least one target gene according to the present disclosure. Thus, a vector system may comprise only one (plasmid) vector construct or multiple (plasmid) vector constructs, the latter of which may be stably or transiently transformed simultaneously or sequentially into the corresponding recombinant host organism such that the target genes encoded by the individual constructs may be transcribed and translated by the host organism.

The terms amino acid, protein and polypeptide are used interchangeably herein. The amino acids disclosed herein, or functional portions thereof, have enzymatic function after correct folding. Accordingly, the term enzyme is also used herein interchangeably for the term amino acid.

Whenever the present disclosure refers to sequence homologies or sequence identities of nucleic or protein sequences in terms of percentages, such references are to values as can be calculated using EMBOSS Water Pairwise Sequence Alignments (nucleotides) (http://www.ebi.ac.uk/Tools/psa/emboss_water/nucleotide.html) for nucleic acid sequences and EMBOSS Water Pairwise Sequence Alignments (proteins) (http://www.ebi.ac.uk/Tools/psa/emboss-_water/) for amino acid sequences, respectively. Local sequence alignment tools provided by the European Molecular Biology Laboratory (EMBL) European Bioninformatics Institute (EBI) use a modified Smith-Waterman algorithm (see http://www.ebi.ac.uk/Tools/psa/ and Smith, T. F. & Waterman, M. S. "Identification of common molecular subsequences" *Journal of Molecular Biology,* 1981 147 (1): 195-197). Furthermore, here, when performing the respective pairwise alignment of two sequences using the modified Smith-Waterman algorithm, reference is made to the default parameters currently given by EMBL-EBI. These are (i) for amino acid sequences: Matrix=BLOSUM62, Gap open penalty=10 and Gap extend penalty=0.5 and (ii) for nucleic acid sequences: Matrix=DNAfull, Gap open penalty=10 and Gap extend penalty=0.5.

The growing and cultivation, isolation and purification of a recombinant microorganism or fungus or a protein or enzyme encoded by a nucleic acid according to the disclosure of the present invention is known to those skilled in the art.

The terms protein, polypeptide and enzyme are used interchangeably due to the invariably enzymatic function of the gene products disclosed herein. Likewise, the terms gene and nucleic acid (segment) are used interchangeably for purposes of the present disclosure.

The nucleic acids, nucleotide sequences or nucleic acid segments (these terms are used interchangeably for DNA sequences encoding a functional enzyme, or a functional region thereof) used according to the present invention to express a desired target protein may optionally be codon-optimized, i.e., the codon usage of a gene is adapted to that of the recombinant microorganism or fungus selected as the expression strain. It is known to those skilled in the art that a desired target gene encoding a protein of interest can be modified without altering the translated protein sequence to accommodate specific species-dependent codon usage. Thus, the nucleic acids of the present invention to be transformed can be specifically adapted to the codon usage of *E. coli* or another bacterium, *Saccharomyces* spp. or another yeast.

The disclosed carboxylic acids can be present either in their free form or esterified to alcohols, which occur, for example, as components of lipids.

Where the configuration(s) of (Z)/(E) isomers is not specifically indicated herein for a named compound, the indication includes all possible configurational isomers of the corresponding compound, or a mixture thereof. It should be noted that certain enzymes mentioned herein are capable of recognizing and converting both isomers of a compound of interest.

DETAILED DESCRIPTION

The problem of the present invention is primarily solved by providing a biotechnological method for the production of at least one unsaturated aldehyde and its corresponding carboxylic acid and/or at least one saturated aldehyde and its corresponding carboxylic acid, the method comprising providing at least one alpha-dioxygenase and at least one aldehyde dehydrogenase.

The aldehyde obtained is always shortened by one carbon atom compared to the reactant used. A saturated aldehyde in the context of the present invention refers to an aldehyde without double bonds, whereas an unsaturated aldehyde refers to aldehydes with double bonds present. The corresponding carboxylic acid in this case is a compound with the same chain length and the same degree of saturation as the aldehyde obtained, but which carries at least one carboxyl group. The at least one alpha-dioxygenase used according to the invention catalyzes the oxidation of carboxylic acids of chain length C6-C22 at the alpha carbon atom, so that the aldehyde corresponding to the carboxylic acid and shortened by one carbon atom is formed.

Due to its substrate specificity, the at least one aldehyde dehydrogenase used catalyzes the oxidation of an aldehyde to the corresponding carboxylic acid, which in turn can be further converted to an aldehyde shortened by one carbon atom with the alpha-dioxygenase. Thus, the method of the invention can be used to selectively produce aldehyde mixtures with aldehydes that have different chain lengths.

In one embodiment of the method according to the invention, the alpha-oxidation and the aldehyde oxidation can be carried out simultaneously, whereas in another embodiment, the alpha-oxidation can be carried out first and then the aldehyde oxidation, whereby the reaction cycle can be continued in both embodiments until the desired product is obtained.

In a preferred embodiment of the method according to the invention, the biotechnological production method may be a fermentative method comprising the following steps:

i. Providing at least one recombinant microorganism or fungus containing a nucleic acid segment comprising at least one gene encoding an alpha-dioxygenase and/or at least one gene encoding an aldehyde dehydrogenase;
ii. Culturing the at least one recombinant microorganism under conditions that allow expression of the corresponding expression product;
iii. Adding at least one carboxylic acid or at least one carboxylic acid esterified with an alcohol to the at least one cultured recombinant microorganism;
iv. Obtaining at least one unsaturated aldehyde and its corresponding carboxylic acid and/or at least one saturated aldehyde and its corresponding carboxylic acid by reacting the at least one alpha-dioxygenase and the at least one aldehyde dehydrogenase with the at least one carboxylic acid or carboxylic acid esterified to an alcohol of step iii.

A fermentative method in the context of the present invention refers to a method in which, in at least one step, a recombinant microorganism is cultured that expresses the at least one alpha-dioxygenase and the at least one aldehyde dehydrogenase required to produce the product of the invention. The expression product here is the at least one alpha-dioxygenase and/or the at least one aldehyde dehydrogenase. Thereby, according to one embodiment, the reaction of the reactant can take place by secretion of the enzyme into the reaction mixture in which the reactants are present, whereas according to another embodiment, the reaction can take place in the cytosol of the at least one microorganism and the product can subsequently be secreted.

Providing in the context of the present invention always means involving an active step to make available a reactant, an enzyme or the like. According to one embodiment, providing may always be a technical step, such as cloning a reaction organism or producing a reactant.

In another preferred embodiment of the method according to the invention, the biotechnological production method may be an enzymatic method comprising the following steps:

i. Providing at least one alpha-dioxygenase and at least one aldehyde dehydrogenase, wherein the at least one alpha-dioxygenase and/or the at least one aldehyde dehydrogenase may be naturally, chemically or biotechnologically produced;
ii. Adding at least one carboxylic acid or at least one carboxylic acid esterified with an alcohol to the provided enzymes of step i;
iii. Obtaining at least one unsaturated aldehyde and its corresponding carboxylic acid and/or at least one saturated aldehyde and its corresponding carboxylic acid by reacting the at least one alpha-dioxygenase and the at least one aldehyde dehydrogenase with the at least one carboxylic acid or carboxylic acid esterified to an alcohol of step ii.

An enzymatic method in the context of the present invention denotes a method in which the at least one alpha-dioxygenase and the at least one aldehyde dehydrogenase may be present purified or partially purified outside a microorganism. In one embodiment, the two enzymes may be present as a cell lysate, which denotes the state of microorganisms that can no longer be cultured and that have been digested by physical, chemical or enzymatic processes. In a further embodiment, the enzymes may be present with a purity of >80%, having been purified by a purification process familiar to those skilled in the art. In yet another embodiment, the enzymes may be present at <80% purity, having been partially purified by a purification process known to those skilled in the art. In still another embodiment, the enzymes may be obtained by protein synthesis and optionally purified.

A reactant (starting material) of biotechnological origin is a reactant produced by fermentation of microorganisms, whereby a reactant of natural origin may be obtained from a natural source, for example, a plant, fungus, animal, microorganism, or soil. A reactant of chemical origin may be produced by a chemical synthesis from precursors of the reactant.

In a further preferred embodiment, at least one of the reactants of the method according to the invention may be of biotechnological, natural or chemical origin. The above applies to the reactants of biotechnological, natural or chemical origin.

According to a further preferred embodiment of the method of the invention, the reactants can be selected from the group of carboxylic acids and carboxylic acids esterified with alcohols. Preferred reactants are those selected from the group consisting of palmitoleic acid, arachidonic acid, alpha-linolenic acid, linoleic acid, gamma-linolenic acid, oleic acid, punicic acid, alpha-elaeostearic acid, docosahexaenoic acid, eicosapentaenoic acid, petroselinic acid, chaulmoogric acid, alpha-licaric acid, olive oil, canola oil, macadamia nut oil, sea buckthorn fruit oil, tung oil, fish oil, borage oil, chaulmoogra oil, parsley oil, oiticica oil, pomegranate seed oil, coconut oil, sunflower oil, field stone seed oil and grape seed oil, as well as fungal oils obtained from genera independently selected from *Conidiobolus, Flammulina, Fomes, Ganoderma, Mortierella, Panellus, Pleurotus, Psathyrella, Stereum, Umbelopsis.*

In a further preferred embodiment, the product of the method according to the invention may be at least a saturated aldehyde and its corresponding carboxylic acid and/or an unsaturated aldehyde and its corresponding carboxylic acid. Here, the products of the method according to the invention can preferably be selected from the group comprising 7Z,10Z-hexadecadienal, 8Z,11Z-heptadecadienal, 6E,9E-pentadecadienal, 7Z-hexadecenal, 8Z-pentadecenal, 7Z-tetradecenal, 8Z,11Z,14Z-heptadecatrienal, 7Z,10Z,13Z-hexadecatrienal, 4Z,7Z,10Z,13Z-nonadecatetraenal, 8Z,10E,12E-heptadecatrienal, 8Z,10E,12Z-heptadecatrienal, 7Z,9E,11Z-hexadecatrienal, 7Z,9E,11E-hexadecatrienal, 9-decenal, 10-undecenal, 3Z-decenal, 4Z-undecenal, 7Z-dodecenal, 8Z-tridecenal, 7Z-tetradecenal, 8Z-pentadecenal, 9Z-tetradecenal, 10Z-pentadecenal, 7Z-pentadecenal, 8Z-hexadecenal, 9Z-hexadecenal, 10Z-heptadecenal, 5Z,8Z-tetradecadienal, 6Z,9Z-pentadecadienal, 7Z,10Z-tetradecadienal, 8Z,11Z-pentadecadienal, 7Z,9E-hexadecadienal, 8Z,10E-heptadecadienal, 8E,10Z-hexadecadienal, 9E,11Z-heptadecadienal, 9-methylundecanal-, 10-methylundecanal, 10-methyldodecanal, 11-methyldodecanal, 11-methyltridecanal-, 12-methyltridecanal, 12-methyltetradecanal, 13-methyltetradecanal and 13-methylpentadecanal.

In the context of the present invention, all compounds in which the positions of the double bond are not specifically indicated with respect to the (Z)/(E) configuration include all possible positions of the double bond and mixtures of the relevant compounds.

According to a further embodiment of the method of the invention, the at least one recombinant microorganism may be selected from the group consisting of *Escherichia coli*, preferably *E. coli* BL21, *E. coli* MG1655, *E. coli* W3110, and their derivatives, *Bacillus* spp, preferably *B. licheniformis, B. subitilis* or *B. amyloliquefaciens*, and their derivatives, *Saccharomyces* spp, preferably *S. cerevesiae*, and their derivatives, *Hansenula* or *Komagatella* spp, preferably *K. phaffii* and *H. polymorpha*, and their derivatives, *Kluyveromyces* spp, preferably *K. lactis.*

According to a preferred embodiment, at least one NADH oxidase and/or at least one lipase may additionally be provided.

NADH oxidases are those that can catalyze the oxidation of an aldehyde due to their substrate specificity and regioselectivity. In a preferred embodiment of the method according to the invention, these can be used as additional enzymes to make the closely coordinated methods even more efficient by recycling the corresponding cofactor.

In another preferred embodiment of the method of the invention, the at least one NADH oxidase may comprise an amino acid sequence, wherein the amino acid sequence is independently selected from the group consisting of SEQ IDs NO: 62 and 64, or a sequence having at least 90%, 91%, 92%, 93%, 94%, 95%, 96%, 97%, 98%, 99% or 100% sequence identity thereto. In one embodiment, the amino acid sequence encoding the NADH oxidase is encoded by a nucleic acid sequence selected from the group consisting of SEQ IDs NO: 61 and 62, or a sequence having at least 90%, 91%, 92%, 93%, 94%, 95%, 96%, 97%, 98%, 99% or 100% sequence identity thereto.

Furthermore, an enzyme that catalyzes the reaction according to the invention according to the various aspects and embodiments of the present invention may be a catalytically active domain or fragment of the particular enzyme from which it is derived.

In another preferred embodiment, the at least one lipase may be a commercial lipase selected from the group consisting of *Candida antarctica, Aspergillus niger, Rhizopus oryzae, Penicillium camembertii, Mucor juvanicus, Penicillium roqueforti, porcine pancreas, Candida rugosa, Rhizomucor miehei* or *Rhizopus delemar.*

In yet another preferred embodiment of the method of the invention, the alpha-dioxygenase may comprise an amino acid sequence selected from the group consisting of SEQ ID NOs: 8, 11, 37, 38, 39, 40, 41, 43, 44, 45, 46, 47, 48, 50, 51, 52, 53, 54, 55, or 56 or a sequence having at least 90%, 91%, 92%, 93%, 94%, 95%, 96%, 97%, 98%, 99%, or 100% sequence identity thereto.

In another preferred embodiment, the at least one aldehyde dehydrogenase may comprise or consist of an amino acid sequence, wherein the amino acid sequence may be selected from the group consisting of SEQ ID NOs: 9, 10, 12, 13, 14, 59, or 60 or a sequence having at least 90%, 91%, 92%, 93%, 94%, 95%, 96%, 97%, 98%, 99%, or 100% sequence identity thereto.

Another embodiment of the present invention may be directed to nucleic acid sequences or segments thereof encoding polypeptides having enzymatic function for the purpose of purification, secretion, detection or localization of the at least one alpha-dioxygenase and/or the at least one aldehyde dehydrogenase and/or the at least one lipase and/or the at least one NADH oxidase. These nucleic acid segments are also referred to as tag sequences and may precede (N-terminal) and/or follow (C-terminal) the nucleic acid segments encoding the at least one alpha-dioxygenase and/or the at least one aldehyde dehydrogenase. Preferred tag sequences are selected from the following list: Polyhistidine (His) tag, glutathione S-transferase (GST) tag, thioredoxin tag, FLAG tag, green fluorescent protein (GFP) tag, streptavidin tag, maltose binding protein (MBP) tag, chloroplast transit peptide, mitochondrial transit peptide and/or secretion tag. Moreover, the skilled person is aware of a number of other suitable tag sequences for microorganisms or fungi of interest as a production strain, wherein these tag sequences allow secretion of a polypeptide of interest directly into the culture supernatant. This may be advantageous in some embodiments to facilitate obtaining and optionally purifying a polypeptide of interest.

In another aspect of the present invention, the invention relates to a vector system, preferably a plasmid vector system, which comprises at least one vector or plasmid vector comprising a nucleic acid segment (a) comprising at least one gene coding for an alpha-dioxygenase, and a nucleic acid segment (b) comprising at least one gene coding for an aldehyde dehydrogenase, and optionally comprising, as part of the nucleic acid segment (a) and/or (b), a nucleic acid segment comprising at least one gene encoding an NADH oxidase and/or a nucleic acid segment comprising at least one gene encoding a lipase, wherein the nucleic acid segment (a) and/or the nucleic acid segment (b) is provided on the same vector, or on two or more separate vectors.

According to a preferred embodiment, the vector system may encode expression of at least one polypeptide, wherein said polypeptide is selected from the group consisting of SEQ ID NOs: 8, 9, 10, 11, 12, 13, 14, 37, 38, 39, 40, 41, 43, 44, 45, 46, 47, 48, 50, 51, 52, 53, 54, 55, 56, 59 or 60 or a sequence having at least 90%, 91%, 92%, 93%, 94%, 95%, 96%, 97%, 98%, 99% or 100% sequence identity thereto.

In another aspect, the present invention relates to a composition comprising an aldehyde mixture obtained by a method according to the invention, characterized in that the composition comprises at least one, or preferably at least two or three, aldehydes selected from the group consisting of 7Z-tetradecenal, 8Z-pentadecenal, pentadecanal, 7Z-hexadecenal and 8Z-heptadecenal, wherein the one or more aldehydes are each present in a proportion of about 0.0001-20 wt. %, preferably 0.001-10 wt. %, more preferably 0.01-5 wt. %, each with respect to the total composition, and wherein the composition optionally contains further aldehydes obtained by a method according to any of claims 1 to 12, or wherein the composition comprises 7Z-tetradecenal in a proportion of about 0.0001-20 wt. %, or wherein the composition comprises 8Z-pentadecenal in a proportion of about 0.0001-20 wt %, relative to the total composition, or wherein the composition comprises pentadecanal in an amount of about 0.0001-20 wt. %, relative to the total composition, or wherein the composition comprises 7Z-hexadecenal in an amount of about 0.0001-20 wt. %, relative to the total composition, or wherein the composition comprises 8Z-heptadecenal in an amount of about 0.0001-20 wt. %, relative to the total composition, or wherein the composition comprises at least 8Z-pentadecenal and pentadecanal, wherein the proportion of 8Z-pentadecenal and pentadecanal in the total composition comprises about 0.0001-20 wt. %, or wherein the composition comprises at least 8Z-pentadecenal and 8Z-heptadecenal, wherein the proportion of 8Z-pentadecenal and 8Z-heptadecenal in the total composition comprises about 0.0001-20 wt. %.

A composition in the context of the present invention is a semi-finished or finished product composition and is preferably selected from the group consisting of a preparation serving nourishment or pleasure or a cosmetic or cleansing preparation.

Preparations serving nourishment or pleasure in the sense of the present invention are e.g. bakery products (e.g. bread, dry cookies, cakes, other pastries), confectionery (e.g. chocolates, chocolate bar products, other bar products, fruit gums, hard and soft caramels, chewing gum), alcoholic or non-alcoholic beverages (e.g., coffee, tea, wine, wine-based beverages, beer, beer-based beverages, liquors, spirits, brandies, fruit-based sodas, isotonic beverages, soft drinks, nectars, fruit and vegetable juices, fruit or vegetable juice preparations), instant beverages (e.g., instant cocoa drinks, instant tea drinks, instant coffee drinks, instant fruit drinks), meat products (e.g., ham, fresh or raw sausage preparations, seasoned or marinated fresh or cured meat products), eggs or egg products (dried egg, egg white, egg yolk), cereal products (e.g., breakfast cereals, cereal bars, pre-cooked ready-to-eat rice products), dairy products (e.g. milk drinks, buttermilk drinks, milk ice cream, yogurt, kefir, cream cheese, soft cheese, hard cheese, dried milk powder, whey, butter, buttermilk, partially or wholly hydrolyzed milk protein-containing products), products made from soy protein or other soybean fractions (e.g. soy milk and products made therefrom, fruit drinks containing soy protein, preparations containing soy lecithin, fermented products such as tofu or tempeh or products made therefrom), fruit preparations (e.g., jams, fruit ice cream, fruit sauces, fruit fillings), vegetable preparations (e.g., ketchup, sauces, dried vegetables, frozen vegetables, pre-cooked vegetables, cooked vegetables), snacks (e.g. baked or deep-fried potato chips or potato dough products, corn- or peanut-based extrudates), fat- and oil-based products or emulsions thereof (e.g. mayonnaise, remoulade, dressings), other ready meals and soups (e.g. dry soups, instant soups, pre-cooked soups), spices, seasoning mixtures and in particular seasonings, which are used for example in the snack sector. The preparations in the sense of the invention can also serve as semi-finished goods for the production of further preparations serving nourishment or pleasure. The preparations within the meaning of the invention may also be in the form of capsules, tablets (uncoated as well as coated tablets, e.g. enteric coatings), lozenges, granules, pellets, solid mixtures, dispersions in liquid phases, as emulsions, as powders, as solutions, as pastes or as other preparations which can be swallowed or chewed as food supplements.

A cosmetic or cleansing preparation in the sense of the present invention is a preparation which can be used for cleaning, caring for or perfuming the body or for cleansing. Preferred cosmetic preparations are selected from the group consisting of floor cleaners, window glass cleaners, dishwashing detergents, bathroom and sanitary cleaners, scouring milks, solid and liquid toilet cleaners, powder and foam carpet cleaners, textile fresheners, ironing aids, liquid detergents, powder detergents, laundry pretreatment agents such as bleaches, softeners, soaking agents and stain removers, laundry softeners, washing soaps, washing tablets, disinfectants, surface disinfectants and air fresheners in liquid, gel or solid form, aerosol sprays, waxes and polishes such as furniture polishes, floor waxes, shoe polishes and personal care products such as solid and liquid soaps, shower gels, shampoos, shaving soaps, shaving foams, bath oils, cosmetic emulsions of the oil-in-water type, water-in-oil type and water-in-oil-in-water type, such as skin creams and lotions, facial creams and lotions, sunscreen creams and lotions, after-sun creams and lotions, hand creams and lotions, foot creams and lotions, depilatory creams and lotions, after-shave creams and lotions, tanning creams and lotions, hair care products, such as hair sprays, hair gels, setting hair lotions, hair conditioners, permanent and semi-permanent hair colorants, hair shaping products such as cold waves and hair straightening products, hair tonics, hair creams and lotions, deodorants and antiperspirants such as underarm sprays, roll-ons, deodorant sticks, deodorant creams, decorative cosmetic products such as eye shadows, nail polishes, make-ups, lipsticks, mascara, as well as candles, lamp oils, incense sticks, insecticides, repellents and propellants.

In a preferred embodiment, the obtained composition contains further aldehydes, carboxylic acids or alcohols selected from the group consisting of dodecanol, tridecanal, tridecanol, tetradecanal, 8Z-tetradecenol, tetradecanol, pentadecanal, pentadecanol, octanoic acid, decanoic acid, tridecanal, tridecenal, pentadecenal and 8Z-tetradecenal, depending on the embodiment of the method according to the invention.

In a further embodiment, the individual components of the mixtures obtained can be partially or completely purified by a method known to the skilled person. Accordingly, a major advantage of these mixtures is their universal applicability in a wide range of industries, since they can be used both as mixtures and as individual components.

The present invention is further explained below with reference to non-limiting examples and based on the disclosure provided in the sequence listing and drawings.

EXAMPLES

Example 1: Creation of Single Constructs

For the generation of the single constructs used for protein expression, a suitable vector with a coding sequence was generated. For this purpose, the respective coding sequence of different target genes was synthesized and cloned between two restriction sites into the vector pET28a (Merck Chemicals GmbH, Schwalbach) or pETDuet-1 (Merck Chemicals GmbH, Schwalbach). An overview of the cloned genes with the respective restriction sites used for cloning is summarized in Table 1. For all SEQ ID Nos, the codon usage of the gene was adapted to *E. coli* as one of the intended expression hosts. In addition, SEQ ID NO: 3 carries a point mutation relative to the sequence of origin obtained from the respective organism.

TABLE 1

Overview of the genes, vectors and restriction sites used.

| Gene | SEQ ID NO (nucleic acid/protein) | Vector used | Restriction sites used |
|---|---|---|---|
| Osa-DOX | 1/8 | pET28a | BamHI, XhoI |
| VhFaldh | 2/9 | pETDuet-1 | NdeI, BsuRI |
| Maqu3410 | 7/14 | pETDuet-1 | NdeI, PvuI |
| ReAldh | 5/12 | pET28a | NdeI, BamHI |
| GtAldh | 6/13 | pET28a | NdeI, BamHI |
| LsNOX | 4/11 | pETDuet-1_ VhFAldh pETDuet-1_ Maqu3410 | XbaI, HindII |
| VhFaldh T175Q | 3/10 | pETDuet-1_VhFAldh | |

Using standard transformation methods (Maniatis et al. 1983), obtained plasmids were introduced into competent *E. coli* BL21 (DE3) cells, and the cells were grown for 18 h at 37° C. on selective solid medium (LB+ampicillin (100 mg/L)+6 g/L agar).

Example 2: Generation of Different VhAldh Variants by Mutagenesis

Starting from the plasmid pET-Duet_LsNOX_VhFALDH, different enzyme variants were generated using the QuikChange II Site-Directed Mutagenesis Kit (Agilent, Waldbronn, Germany). In this process, targeted mutations were introduced in the coding sequence of VhFaldh using specific primers according to the manufacturer's instructions. For the variant pET-Duet_LsNOX_VhFALDHT175Q of VhFALDH, primers VhFALDH-T175Q_fw (SEQ ID NO:15) and VhFALDH-T175Q_rv (SEQ ID NO:16) were used. The sequences of the nucleic acid or the corresponding translated protein are shown in SEQ ID NO: 3 and 10, respectively.

Example 3: Protein Expression and Purification Osa-DOX

To prepare protein expression in a volume of 50 mL, a preculture of 5 mL LB medium (Carl Roth GmbH, Karlsruhe, Germany) was first prepared with the appropriate antibiotic, and using an inoculating loop, *E. coli* BL21 (DE3) cells containing pET28a_OsaDOX were removed from the agar plate and transferred to the preculture. This was then incubated for 16 h at 37° C. and 150 rpm. From the preculture, the main culture was inoculated with 50 mL of LB medium (Carl Roth GmbH, Karlsruhe, Germany) and the appropriate antibiotic so that an optical density at 600 nm of 0.05 was present. The main culture was then incubated at 37° C. and 200 rpm until an optical density at 600 nm of 0.6-1.0 was obtained. To induce protein expression, 0.5 mM isopropyl-β-D-thiogalactopyranoside was added at this time point and the culture was incubated for an additional 16 h at 21° C. Finally, the main culture was centrifuged at 17,105×g for 10 min to obtain the cell pellet and subsequently perform protein extraction and purification. For this purpose, cell disruption was first performed using B-PER protein extraction reagent (Thermo Fisher Scientific, Bonn, Germany) according to the manufacturer's instructions. The cell lysate obtained was then either used directly or processed using a 1 mL HisPur Ni-NTA chromatography column (Thermo Fisher Scientific, Bonn, Germany) according to the manufacturer's instructions.

Example 4: Protein Expression of VhFaldh and LsNOX

To prepare protein expression in a volume of 50 mL, a preculture of 5 mL LB medium (Carl Roth GmbH, Karlsruhe, Germany) was first prepared with the appropriate antibiotic, and using an inoculating loop, *E. coli* BL21 (DE3) cells containing pET-Duet_LsNOX_VhFALDH were removed from the agar plate and transferred to the preculture. This was then incubated for 16 h at 37° C. and 150 rpm. From the preculture, the main culture was inoculated with 50 mL of LB medium (Carl Roth GmbH, Karlsruhe, Germany) and the appropriate antibiotic to give an optical density at 600 nm of 0.1. The main culture was then incubated at 37° C. and 200 rpm until an optical density at 600 nm of 0.6-0.8 was obtained. To induce protein expression, 0.5 mM isopropyl-β-D-thiogalactopyranoside was added at this time point and the culture was incubated for an additional 16 h at 16° C. Finally, the main culture was centrifuged at 17,105×g for 10 min to obtain the cell pellet and subsequently perform protein extraction and purification. For this purpose, cell disruption was first performed using B-PER protein extraction reagent (Thermo Fisher Scientific, Bonn, Germany) according to the manufacturer's instructions. The unclarified cell lysate obtained was then used directly.

Example 5: Hydrolysis of Fatty Acid Triglycerides

In a 1 L round bottom flask, 5-10 g of CALB-imm (Novozym 435; 10,000 U/g) was stirred for 0.5-3 h in 380 mL of tert-butanol (Carl Roth). Then 50 g of triglycerides, and 15 mL of 200 mM Tris-HCl pH 8 buffer were added. The reaction was carried out under vigorous stirring for 15-21 h at 60° C. Subsequently, the enzyme was removed by filtration and the reaction mixture was concentrated to dryness using a rotary evaporator. The product was stored overnight at 4° C. and then taken up in 200 mL 200 mM Tris-HCl pH 2. The fatty acids were extracted by adding 500 mL of tert-butyl methyl ether (Honeywell) with stirring for 1 h. The mixture was transferred to a separatory funnel until phase separation occurred. The organic phase was subsequently transferred to a round bottom flask and concentrated to dryness using a rotary evaporator. The product was stored at −20° C. and the composition was analyzed by GC-MS (20m ZB-1, 60-9-300, split 60:1). Retention indices of the products were determined by comparison with standards.

Example 6: Preparation of Aldehyde Mixtures Using Os-alpha-Dox and VhFaldh

For the reaction of different fatty acids or hydrolysates according to example *E. coli* BL21 (DE3) cells containing pET28a_ OsaDOX according to Example 3 and lysate from *E. coli* BL21 (DE3) cells containing pET-Duet_Ls-NOX_VhFALDH according to Example 4 were used. For this purpose, 25 mM linoleic acid (Sigma-Aldrich), 40 g/L *E. coli* alpha-Dox according to Example 3, lysate from 10 g/L *E. coli* VhFALDH_NOX, 3.25 mM $NAD^+$ (Sigma Aldrich), 0.5% glucose, 0.1% (w/v) gum arabic, and 4.7 mL potassium phosphate buffer pH 8 were suspended in a 50 mL reaction tube.

Here, buffer, linoleic acid, $NAD^+$, glucose, and gum arabic were combined in a 100 mL shake flask with a baffle and mixed at 200 rpm and 37° C. for 5 min. Then indicated cells or lysates were added and the reaction was incubated at 200 rpm and 37° C. for 24 h.

Subsequently, the mixture was adjusted to pH 2 using hydrochloric acid and extracted twice by adding the same volume of ethyl acetate (Sigma-Aldrich) under vortexing (1 min). Separation of the organic from the aqueous phase was performed by centrifugation for 10 min at 17.105×g. Samples were analyzed by gas chromatography (20 m ZB-1 df:0.18 μm i.D.:0.18 mm/60-12-300° KAS). Retention indices for the selected GC method were determined by comparison with standards and GC-MS data.

Example 7: Aldehyde Mixtures According to the Invention

Tables 2 and 3 show exemplary mixtures obtained by the process according to the invention. In addition to the mixtures obtained, the individual components can be purified in a subsequent step.

TABLE 2

Aldehyde mixtures prepared by the method of the invention

| Name | Proportion [%] |
|---|---|
| Dodecanol | 0.847 |
| Tridecanal | 1.768 |
| Tridecanol | 1.640 |
| 7Z-Tridecanal | 3.067 |
| Tetradecanal | 8.739 |
| 8Z-tetradecenol | 2.278 |
| Tetradecanol | 2.649 |
| 8Z-Pentadecenal | 17.770 |
| Pentadecanal | 20.946 |
| Pentadecanol | 0.930 |
| 7Z hexadecenal | 1.893 |
| 8Z-Heptadecenal | 8.543 |

TABLE 3

Aldehyde mixtures prepared by the method of the invention.

| Name | Proportion [%] |
|---|---|
| Octanoic acid | 0.273 |
| Decanoic acid | 0.334 |
| Tridecanal | 0.624 |
| 7Z-tetradecanal | 3.726 |
| Tetradecenal | 2.496 |
| Tridecenoic acid | 0.776 |
| 8Z-Pentadecenal | 19.938 |
| Pentadecanal | 13.124 |
| 8-Tetradecenoic acid | 8.094 |
| 7Z hexadecenal | 6.186 |
| 8Z-Heptadecenal | 34.596 |

The invention claimed is:

1. A biotechnological method for producing at least one unsaturated aldehyde and its corresponding carboxylic acid and/or at least one saturated aldehyde and its corresponding carboxylic acid, the process comprising:

a) providing at least one alpha-dioxygenase comprising an amino acid sequence selected from the group consisting of SEQ ID NOs: 8, 11, 37, 38, 39, 40, 41, 43, 44, 45, 46, 47, 48, 50, 51, 52, 53, 54, 55, or 56 or a sequence having at least 90%, 91%, 92%, 93%, 94%, 95%, 96%, 97%, 98%, 99%, 100% sequence identity thereto;

b) providing at least one aldehyde dehydrogenase comprising an amino acid sequence selected from the group consisting of SEQ ID NOs: 9, 10, 12, 13, 14, 59, or 60 or a sequence having at least 90%, 91%, 92%, 93%, 94%, 95%, 96%, 97%, 98%, 99%, or 100% sequence identity thereto; and c) providing a reactant selected from the group consisting of carboxylic acids and carboxylic acids esterified with alcohols, wherein the alpha-oxidation and the aldehyde oxidation are carried out simultaneously.

2. The method of claim 1, wherein the biotechnological method is a fermentative method comprising the steps of:

i. Providing at least one recombinant microorganism or fungus containing a nucleic acid segment comprising at least one gene encoding an alpha-dioxygenase and/or at least one gene encoding an aldehyde dehydrogenase;

ii. Culturing the at least one recombinant microorganism under conditions that allow expression of the corresponding expression product;

iii. Adding at least one carboxylic acid or at least one carboxylic acid esterified with an alcohol to the at least one cultured recombinant microorganism;

iv. Obtaining at least one unsaturated aldehyde and its corresponding carboxylic acid and/or at least one saturated aldehyde and its corresponding carboxylic acid by reacting the at least one alpha-dioxygenase and the at least one aldehyde dehydrogenase with the at least one carboxylic acid or the carboxylic acid esterified with an alcohol of step iii.

3. The method of claim 1, wherein the biotechnological method is an enzymatic method comprising the steps of:

i. Providing at least one alpha-dioxygenase and at least one aldehyde dehydrogenase, wherein the at least one alpha-dioxygenase and/or the at least one aldehyde dehydrogenase may be naturally, chemically or biotechnologically produced;

ii. Adding at least one carboxylic acid or at least one carboxylic acid esterified with an alcohol to the provided enzymes of step i;

iii. Obtaining at least one unsaturated aldehyde and its corresponding carboxylic acid and/or at least one saturated aldehyde and its corresponding carboxylic acid by reacting the at least one alpha-dioxygenase and the at least one aldehyde dehydrogenase with the at least one carboxylic acid or the carboxylic acid esterified with an alcohol of step ii.

4. The method of claim 1, wherein at least one of the reactants is of biotechnological, natural or chemical origin, or a combination thereof.

5. The method of claim 1, wherein the product of the process is at least one saturated aldehyde and its corresponding carboxylic acid and/or at least one unsaturated aldehyde and its corresponding carboxylic acid selected from the group consisting of 7Z,10Z-hexadecadienal, 8Z,11Z-heptadecadienal, 6E,9E-pentadecadienal, 7Z-hexadecenal, 8Z-pentadecenal, 8Z,11Z,14Z-heptadecatrienal, 7Z,10Z,13Z-hexadecatrienal, 4Z,7Z,10Z,13Z-nonadecatetraenal, 8Z,10E,12E-heptadecatrienal, 8Z,10E,12Z-heptadecatrienal, 7Z,9E,11Z-hexadecatrienal, 7Z,9E,11E-hexadecatrienal, 9-decenal, 10-undecenal, 3Z-decenal, 4Z-undecenal, 7Z-dodecenal, 8Z-tridecenal, 7Z-tetradecenal, 8Z-pentadecenal, 9Z-tetradecenal, 10Z-pentadecenal, 7Z-pentadecenal, 8Z-hexadecenal, 9Z-hexadecenal, 10Z-heptadecenal, 5Z,8Z-tetradecadienal, 6Z,9Z-pentadecadienal, 7Z,10Z-tetradecadienal, 8Z,11Z-pentadecadienal, 7Z,9E-hexadecadienal, 8Z,10E-heptadecadienal, 8E,10Z-hexadecadienal, 9E,11Z-heptadecadienal, 9-methylundecanal, 10-methylundecanal-, 10-methyldodecanal, 11-methyldodecanal, 11-methyltridecanal, 12-methyltridecanal, 12-methyltetradecanal, 13-methyltetradecanal and 13-methylpentadecanal.

6. The method of claim 1, wherein the at least one recombinant microorganism is selected from the group consisting of *Escherichia coli, Bacillus* spp, *Saccharomyces* spp, *Hansenula* or *Komagatella* spp, and *Kluyveromyces* spp.

7. The method of claim 1, wherein additionally at least one NADH oxidase and/or at least one lipase is provided.

8. The method of claim 7, wherein the at least one NADH oxidase comprises an amino acid sequence, wherein the amino acid sequence is selected from the group consisting of SEQ IDs NOs: 62 and 64, or a sequence having at least 90%, 91%, 92%, 93%, 94%, 95%, 96%, 97%, 98%, 99%, or 100% sequence identity thereto.

9. The method of claim 7, wherein the at least one lipase is a commercial lipase selected from the group consisting of *Candida antarctica, Aspergillus niger, Rhizopus oryzae, Penicillium camembertii, Mucor juvanicus, Penicillium roqueforti, porcine pancreas, Candida rugosa, Rhizomucor miehei, Candida antarctica* and *Rhizopus delemar.*

10. The method of claim 1, wherein the reactants are selected from the group consisting of palmitoleic acid, arachidonic acid, alpha-linolenic acid, oleic acid, punicic acid, alpha-elaeostearic acid, docosahexaenoic acid, eicosapentaenoic acid, petroselinic acid, chaulmoogric acid, alpha-licaric acid, olive oil, rapeseed oil, macadamia nut oil, sea buckthorn fruit oil, tung oil, fish oil, borage oil, chaulmoogr oil, parsley oil, oiticica oil, pomegranate seed oil, coconut oil, sunflower oil, grape seed oil, and fungal oils obtained from any of the genera selected from *Conidiobolus, Flammulina, Fomes, Ganoderma, Mortierella, Panellus, Pleurotus, Psathyrella, Stereum, Umbelopsis* and derivatives thereof.

11. The method of claim 6, wherein the at least one recombinant microorganism is selected from the group consisting of *E. coli* BL21, *E. coli* MG1655, *E. coli* W3110, *B. licheniformis, B. subtilis, B. amyloliquefaciens, S. cerevisiae, K. phaffii, H. polymorpha, K. lactis*, and their derivatives.

* * * * *

SEQUENCE LISTING

```
<160> NUMBER OF SEQ ID NOS: 64

<210> SEQ ID NO 1
<211> LENGTH: 1857
<212> TYPE: DNA
<213> ORGANISM: Oryza sativa

<400> SEQUENCE: 1

atgggtagcg gtctgtttaa accgcgtgtt catccggatc tgcgtgatgt ttttagcaaa     60

atgagcttct tcgacaaaat cggctttctg tttatccacg cctttgataa acgtaacctg    120

tggcataaag ttccggttcc gattggtctg ctgtatctga atacccgtcg taccctgctg    180

gaaaaataca atctgctggc agttggtcgt agcagccatg gtgcactgtt tgatccgaaa    240

gaatttctgt atcgtaccga ggatggcaaa tataacgatc cgcataatgc agaagcaggt    300

agccagaata cctttttttgg tcgtaatatg gaaccggttg atcagcagga tgaactgatg    360

agtccggatc cgtttgttgt tgcaaccaaa ctgctggcac gtcgtgaata taaagatacc    420

ggtaaacagt ttaacattct ggcagcagca tggattcagt ttatggttca tgattggatg    480

gaccacatgg aagatacagg tcagattggt attaccgcac cgaaagaagt tgcaaatgaa    540

tgtccgctga aaagctttaa attccacccg accaaagaac tgccgaccaa tagtgatggt    600

atcaaaattg gccattacaa tattcgtacc gcatggtggg atggtagcgc agtgtatggt    660

aataatgaag aacgtgcaga aaaactgcgt acctatgttg atggtaaact ggtgattggt    720

gatgatggcc tgctgctgca taaagaaaat ggtgttgcac tgagcggtga tattcgtaat    780

agctgggcag gcgttagcat tctgcaggcc ctgtttgtta aagaacataa tgccgtttgt    840
```

```
gacgccatca aagaagaaca tccgaatctg tcagatgaag aactgtatcg ttatgccaaa    900

ctggttacca gcgcagttat tgcaaaagtg cataccattg attggaccgt tgaactgctg    960

aaaaccaaaa ccatgcgtgc agcaatgcgt gcaaattggt atggactgct gggcaaaaaa   1020

atcaaagata cctttggtca tattggcggt ccgattctgg gtggtctggt tggtctgaaa   1080

aaaccgaata atcatggtgt tccgtatagc ctgaccgaag aatttaccag cgtttatcgt   1140

atgcatagcc tgattccgag caccctgaaa ctgcgtgatc cgaccggtca gccggatgca   1200

aataatagcc ctccgtgtct ggaagatatt gatattggtg aaatgattgg cctgaaaggt   1260

gaagaacagc tgagcaaaat tggttttgaa aaacaggcac tgagcatggg ttatcaggca   1320

tgtggtgccc tggaactgtg gaattatccg agctttttc gtaatctgat tccgcagaat   1380

ctggatggca ccaatcgtag cgatcgtatt gatctggcag ccctggaagt ttatcgtgat   1440

cgtgaacgta gcgttccgcg ttataatgaa tttcgtcgtc gtctgtttct gatcccgatt   1500

aaaagctggg aagatctgac cagcgataaa gatgcaattg aaaccattcg tgccatttat   1560

ggtgatgacg ttgaaaaact ggatctgctg gttggcctga tggcagagaa aaaaatcaaa   1620

ggttttgcca ttagcgaaac cgcctttaac atttttatcc tgatggccag ccgtcgcctg   1680

gaagcagatc gtttttttac cagtaacttt aacgaggaaa cctatacaaa aaaaggcatg   1740

cagtgggtta aaaccaccga aggtctgcgt gacgttatta atcgtcatta tccggaaatt   1800

accgccaaat ggatgaaaag cagcagcgca tttagcgttt gggatgcaga ttattaa      1857


<210> SEQ ID NO 2
<211> LENGTH: 1533
<212> TYPE: DNA
<213> ORGANISM: Vibrio harveyi

<400> SEQUENCE: 2

atgaatccgc agaccgataa tgtttttat gccaccaatg cctttaccgg tgaagcactg     60

ccgctggcat ttccggttca taccgaagtt gaagttaatc aggcagcaac cgcagcagca    120

aaagttgcac gtgattttcg tcgtctgaat aatagcaaac gtgcaagcct gctgcgtacc    180

attgcaagcg aactggaagc acgtagtgat gatattattg cacgtgcaca tctggaaacc    240

gcactgccgg aagttcgtct gaccggtgaa attgcacgta ccgcaaatca gctgcgtctg    300

tttgcagatg ttgttaatag cggtagctat catcaggcaa ttctggatac cccgaatccg    360

acccgtgcac cgctgccgaa accggatatt cgtcgtcagc agattgcact gggtccggtt    420

gcagtttttg gtgcaagcaa ttttccgctg gcctttagcg cagccggtgg tgataccgca    480

agcgcactgg ctgcaggttg tccggttatt gttaaaggtc ataccgcaca tccgggtaca    540

agccagattg ttgcagaatg tattgaacag gccctgaaac aagaacagct gccgcaggca    600

atttttacac tgctgcaggg taatcagcgt gccctgggtc aggcactggt tagccatccg    660

gaaattaaag cagttggttt taccggtagc gttggtggtg gtcgtgcact gtttaatctg    720

gcacatgaac gtccggaacc gattccgttt tatggtgaac tgggtgcaat taatccgacc    780

tttatttttc cgagcgcaat gcgtgcaaaa gcagacctgg cagatcagtt tgttgcaagc    840

atgacaatgg gttgtggtca gttttgtacc aaaccgggtg ttgtttttgc actgaataca    900

ccggaaaccc aggcatttat tgaaaccgca cagagcctga ttcgtcagca gagcccgagc    960

accctgctga ctccgggtat tcgtgattca tatcagagcc aggttgttag ccgtggtagt   1020

gatgatggta ttgatgttac ctttagccag gcagaaagcc cgtgtgttgc cagcgcactg   1080
```

```
tttgttacca gcagcgaaaa ttggcgtaaa catccggcat gggaagaaga aatttttggt   1140

ccgcagagtc tgattgttgt ttgtgaaaat gttgccgata tgctgagcct gagcgaaatg   1200

ctggcaggta gcctgaccgc aaccattcat gcaaccgaag aagattatcc gcaggttagc   1260

cagctgattc cgcgtctgga agaaattgca ggtcgtctgg tttttaatgg ttggccgacc   1320

ggtgttgaag ttggttatgc aatggttcat ggtggtccgt atccggcaag cacccatagc   1380

gcaagcacca gcgttggtgc agaagcaatt catcgttggc tgcgtcctgt tgcatatcag   1440

gccctgccgg aaagcctgct gccggatagc ctgaaagcag aaaatccgct ggaaattgcc   1500

cgtgcagttg atggtaaagc agcacatagc taa                                1533
```

<210> SEQ ID NO 3
<211> LENGTH: 1533
<212> TYPE: DNA
<213> ORGANISM: Vibrio harveyi

<400> SEQUENCE: 3

```
atgaatccgc agaccgataa tgttttttat gccaccaatg cctttaccgg tgaagcactg     60

ccgctggcat ttccggttca taccgaagtt gaagttaatc aggcagcaac cgcagcagca    120

aaagttgcac gtgattttcg tcgtctgaat aatagcaaac gtgcaagcct gctgcgtacc    180

attgcaagcg aactggaagc acgtagtgat gatattattg cacgtgcaca tctggaaacc    240

gcactgccgg aagttcgtct gaccggtgaa attgcacgta ccgcaaatca gctgcgtctg    300

tttgcagatg ttgttaatag cggtagctat catcaggcaa ttctggatac cccgaatccg    360

acccgtgcac cgctgccgaa accggatatt cgtcgtcagc agattgcact gggtccggtt    420

gcagtttttg gtgcaagcaa ttttccgctg gcctttagcg cagccggtgg tgataccgca    480

agcgcactgg ctgcaggttg tccggttatt gttaaaggtc atcaggcaca tccgggtaca    540

agccagattg ttgcagaatg tattgaacag gccctgaaac aagaacagct gccgcaggca    600

atttttacac tgctgcaggg taatcagcgt gccctgggtc aggcactggt tagccatccg    660

gaaattaaag cagttggttt taccggtagc gttggtggtg gtcgtgcact gtttaatctg    720

gcacatgaac gtccggaacc gattccgttt tatggtgaac tgggtgcaat taatccgacc    780

tttatttttc cgagcgcaat gcgtgcaaaa gcagacctgg cagatcagtt tgttgcaagc    840

atgacaatgg gttgtggtca gttttgtacc aaaccgggtg ttgtttttgc actgaataca    900

ccggaaaccc aggcatttat tgaaaccgca cagagcctga ttcgtcagca gagcccgagc    960

accctgctga ctccgggtat tcgtgattca tatcagagcc aggttgttag ccgtggtagt   1020

gatgatggta ttgatgttac ctttagccag gcagaaagcc cgtgtgttgc cagcgcactg   1080

tttgttacca gcagcgaaaa ttggcgtaaa catccggcat gggaagaaga aatttttggt   1140

ccgcagagtc tgattgttgt ttgtgaaaat gttgccgata tgctgagcct gagcgaaatg   1200

ctggcaggta gcctgaccgc aaccattcat gcaaccgaag aagattatcc gcaggttagc   1260

cagctgattc cgcgtctgga agaaattgca ggtcgtctgg tttttaatgg ttggccgacc   1320

ggtgttgaag ttggttatgc aatggttcat ggtggtccgt atccggcaag cacccatagc   1380

gcaagcacca gcgttggtgc agaagcaatt catcgttggc tgcgtcctgt tgcatatcag   1440

gccctgccgg aaagcctgct gccggatagc ctgaaagcag aaaatccgct ggaaattgcc   1500

cgtgcagttg atggtaaagc agcacatagc taa                                1533
```

<210> SEQ ID NO 4
<211> LENGTH: 1359

<212> TYPE: DNA
<213> ORGANISM: Lactobacillus sanfrancisco

<400> SEQUENCE: 4

```
atgaaagtta ttgtagtagg ttgtactcac gctggcactt ttgcagttaa gcaaacgatt     60
gccgatcacc ccgatgcaga tgtgactgta tatgaaatga atgataacat ttccttttta    120
tcatgtggaa tcgcccttta cttaggtaaa gaaattaaaa acaatgatcc ccgagggctt    180
ttctactcaa gtccagaaga attaagcaat cttggagcta acgtccaaat gcgtcatcaa    240
gttacaaacg ttgatccaga aacaaaaaca atcaaagtta aagatttaat caccaacgaa    300
gaaaaaacag aagcatatga caaattaatt atgaccactg gttctaagcc tactgttcct    360
ccaatccctg gaatcgatag tagtcgcgtt tacctttgta aaaactataa cgatgctaaa    420
aagttatttg aagaagctcc caaagctaaa acgattacta tcattggttc tggttatatt    480
ggtgccgaac tggctgaagc ctactcaaac caaaattata acgttaattt aattgatggt    540
catgaacgag ttctttacaa gtattttgat aaagaattta ctgatatttt agccaaagat    600
tatgaagctc atggtgttaa cctggttctt ggttcaaaag tagctgcttt tgaagaagtc    660
gatgatgaaa ttatcactaa aaccctagat ggtaaagaaa ttaaatctga tattgcaatt    720
ctttgtatcg gtttccgccc taacactgaa ttacttaaag gtaaagttgc catgttggat    780
aacggtgcaa tcattactga tgaatacatg cattcatcaa atcgcgacat ttttgctgct    840
ggtgatagtg ccgccgttca ctacaacccc actaattcta acgcctacat tcctttagct    900
accaacgccg tacgccaagg gagattagtt ggcctaaatc tgactgaaga caaagtaaaa    960
gacatgggaa cccaatcttc atctggtctt aaactatacg gtcggactta tgtctcaact   1020
ggaatcaata cggctcttgc taaagccaat aatttaaaag ttagcgaagt aatcatagct   1080
gataattatc gtccagaatt tatgttatca acggatgaag ttttaatgtc attagtgtat   1140
gatcctaaga ctcgtgtaat tttgggaggg gcgctttcaa gtatgcacga tgtttcgcaa   1200
tcagcgaacg tcttatcagt atgtattcaa aataaaaaca cgattgacga tttagcaatg   1260
gtggatatgt tattccaacc acaatttgat cgtccgttta actacttaaa cattctaggc   1320
caagctgctc aagcacaagc tgacaaagca cataaataa                          1359
```

<210> SEQ ID NO 5
<211> LENGTH: 1524
<212> TYPE: DNA
<213> ORGANISM: Rhodococcus erythropolis

<400> SEQUENCE: 5

```
atgaccgtgt atgcccgtcc gggtaccgca gatgccatta tgagctttca gagtcgttat     60
gataattgga ttggtaatga atgggttgca ccggtgaaag gtcagtattt tgaaaatccg    120
accccggtta ccggccagaa tttttgcgat gtggcccgta gcaccgccga agatattgaa    180
ctggccctgg atgcagcaca tgcagccgca ccggcatggg gtaaaaccag cgttgcagaa    240
cgtgccatta ttctgaataa aattgcagat cgcatggaag aaaatctgga aagcattgcc    300
ctggccgaaa gttgggataa tggcaaaccg attcgcgaaa ccctgaatgc agatattccg    360
ctggccattg atcattttcg ttattttgcc ggcgcaattc gtgcacagga aggcagtctg    420
agtgaaatta atagtgatac cgtggcatat cattttcatg aaccgctggg cgtggtgggt    480
cagattattc cgtggaattt tccgattctg atggcagttt ggaaactggc cccggcactg    540
gcagcaggca atgcaattgt tctgaaaccg gcagaacaga ccccggttag tattctgcat    600
```

-continued

```
ctgattggta ttattggcga tctgctgccg gcaggtgtgc tgaatattgt gaatggtttt    660
ggcgtggaag ccggtaaacc gctggcaagc agcccgcgta ttaaaaaaat tgcctttacc    720
ggtgaaacca ccaccggtcg tctgattatg cagtatgcca gccagaatct gattccggtt    780
accctggaac tgggtggcaa aagtccgaat attttttta gtgatgtgct ggccagtaat     840
gatgattatc aggataaagc actggaaggt tttaccatgt ttgccctgaa tcagggcgaa    900
gtgtgcacct gcccgagtcg cagtctgatt caggaagata tttttgatga attcctggcc    960
atggcagcca ttcgcaccaa agcagttcgt cagggtgatc cgctggatac cgataccatg   1020
attggtgcac aggccagtaa tgaccagctg gaaaaaattc tgagctatat tgaaatcggc   1080
aaagcagaag gtgccaaagt tattaccggt ggtgaacgtg cagaactggg tggtgatctg   1140
agcggtggtt attatgtgca gccgaccgtt tttaccggta ataataaaat gcgcattttc   1200
caggaagaaa tttttggccc ggtggtgagt gtgaccagtt ttaaagatta tgatgaagcc   1260
attgagatcg ccaatgatac cctgtatggt ctgggcgcag gcgtttggag ccgcgatggt   1320
ggtgtggcct atcgtgccgg tcgcgatatt caggccggcc gtgtttggac caatacctat   1380
catcagtatc cggcccatgc agcatttggt ggctataaac agagtggtat tggccgcgaa   1440
aatcatctga tgatgctgag ccattatcag cagaccaaaa atctgctggt tagctatgca   1500
cagaaagcac agggcttttt ttaa                                          1524
```

<210> SEQ ID NO 6
<211> LENGTH: 1521
<212> TYPE: DNA
<213> ORGANISM: Geobacillus thermodenitrificans

<400> SEQUENCE: 6

```
atgatctacg cacagccggg ccagccgggc gcattagtta cctttaaaaa acgttatgag     60
aacttcatcg gtggcaaatg ggttccgccg gtggatggcg aatattttga aaatattacc    120
ccgattaccg gtaaaccgta ttgtgaagtg ccgcgtagta aagccgccga tattgaactg    180
gcactggatg cagcacatgc cgcaaaagat gaatggggcc gcaccagccc ggccaaacgt    240
gcaagactgc tgaataaaat tgccgatcgc atggaagaaa atctggaact gctggcagtg    300
gcagaaacct gggaaaatgg taaaccgatt cgcgaaaccc tggcagccga tattccgctg    360
gcaattgatc attttcgcta ttttgcaagt tgcattcgtg cacaggaagg taccattagt    420
gaaattgatc atgataccgt tgcctatcat tttaaagaac cgctgggtgt ggttggtcag    480
attattccgt ggaattttcc gattctgatg gccgcatgga aactggcacc ggcactggcc    540
gcaggtaatt gcgtggttct gaaaccggca gaacagaccc cgaccagcat tctggtgctg    600
attgaactga ttgaagattt actgccgccg ggcgtggtga atattgttaa tggttttggc    660
ctggaagccg gtaaaccgct ggcaagcaat ccgcgcgtgg ccaaagttgc atttaccggt    720
gaaaccacca ccggccgcct gattatgcag tatgcaagcc agaatattgt tccggtgacc    780
ctggaactgg gtggcaaaag cccgaatatt ttttttgcag atgttatgga taaggacgat    840
gaatttttg ataaggccct ggaaggtttt accatgtttg ccctgaatca gggcgaagtt     900
tgtacctgcc cgagccgtgc actgattcat gaaagtattt atgatgcctt tatggaacgc    960
gcactggaac gcgtgaaaca gattaaacag ggtaatccgc tggataccga aaccatgatt   1020
ggcgcccagg caagtagcga acagctggaa aaaattctga gttatattga tatcggcaag   1080
caggaaggtg cagaactgct gattggcggt gaacgtaata tgctggaagg cgaactggcc   1140
ggtggctatt atgttaaacc gaccattttt aaaggccata ataaaatgcg tatcttccag   1200
```

gaagaaattt ttggcccggt gctggccgtg accaccttta aagatgaaga tgaagccctg 1260
gcaattgcca atgaaaccct gtatggtctg ggtgcaggtg tttggacccg caatattaat 1320
accgcctatc gttttggtcg tggtattcag gccggccgcg tgtggaccaa ttgctatcat 1380
gtttatccgg cccatgccgc ctttggtggt tataaaatga gtggcattgg ccgcgaaacc 1440
cataaaatga tgctggatca ttatcagcag accaaaaata tgctggttag ctatagcccg 1500
aaaaaactgg gtctgtttta a 1521

<210> SEQ ID NO 7
<211> LENGTH: 1518
<212> TYPE: DNA
<213> ORGANISM: Marinobacter aquaeolei

<400> SEQUENCE: 7
atgatctacg cacagccggg tcaggaaggt agtgtggtga gttttaaaag tcgttatgaa 60
aattacatcg gcggtgaatg ggtggcaccg gttaaaggcc agtattttga taatattacc 120
ccggttaccg gtgcagtgtt ttgtgaagtg ccgcgcagta ccgcagaaga tattgatctg 180
gcactggatg ccgcacataa agcagccccg gcctggggta aaaccagtcc gaccgaacgc 240
agtaatattc tgctgaaaat tgcagatcgc attgaagcaa atctggaaaa actggcagtg 300
gccgaaacct gggataatgg taaagccgtt cgtgaaaccc tgaatgccga tgtgccgctg 360
gccgcagatc atctgcgcta ttttgcaggt tgcattcgtg cacaggaagg tcacatgagt 420
gaaattgatc ataataccgt tgcctatcat tttcatgaac cgctgggcgt tgtgggccag 480
attattccgt ggaatttccc gctgctgatg gccgcatgga aactgggtcc gtgcctggcc 540
agtggcaatt gtaccgtgct gaaaccggca gaacagaccc cggccagtat tctggttctg 600
atggatatta ttggcgatct gctgccgccg ggcgtgatta atattgtgaa tggctatggt 660
attgaggcag gccaggccct ggccaccagc aaacgcattg caaaaattgc attcactggt 720
agcaccccgg ttggcagcca tattctgaaa tgcgcagccg aaaatattat tccgagtacc 780
gtggaactgg gtggtaaaag tccgaatatc tattttagtg atgtgatgaa agccgaaccg 840
gaatttgtgg ataaatgtgt tgaaggtctg gtgctggcct ttttcaatca gggtgaaatt 900
tgcacctgcc cgagccgtgc cctggttcag gaagatatgt ttgaagagtt tatgcagaaa 960
gtggtggaac gtaccaaaag cattaagcgc ggtaatccgc tggataccga tgtgcaggtg 1020
ggcgcacagg caagcaaaga acagtttgat aaaattatga gctacatgga aatcggtcgc 1080
caggaaggtg ccgttgttct gaccggtggc gatcgcgaac atctggaagg cgagtttaat 1140
aatggctttt atattcagcc gaccctgttt aaaggcgata ataagatgcg tgtttttcag 1200
gaagaaattt ttggtccggt ggttggtgtt accaccttta aaaccgaaga agaagccctg 1260
gcaattgcaa atgataccga atttggcctg ggcgccggtg tgtggacccg tgataccaat 1320
ctggcatatc gtatgggtcg taatattcag gcaggtcgcg tgtggatgaa ttgctatcat 1380
gcatatccgg cccatgcagc atttggtggc tataaaaaat caggtattgg ccgtgaaaat 1440
cataaaatgg ccctggaaca ttatcagcag accaaatgca tgttaaccag ctatgatacc 1500
aatccgctgg gtttcttt 1518

<210> SEQ ID NO 8
<211> LENGTH: 618
<212> TYPE: PRT
<213> ORGANISM: Oryza sativa

<400> SEQUENCE: 8

```
Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415
```

```
Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 9
<211> LENGTH: 510
<212> TYPE: PRT
<213> ORGANISM: Vibrio harveyi

<400> SEQUENCE: 9

Met Asn Pro Gln Thr Asp Asn Val Phe Tyr Ala Thr Asn Ala Phe Thr
1               5                   10                  15

Gly Glu Ala Leu Pro Leu Ala Phe Pro Val His Thr Glu Val Glu Val
            20                  25                  30

Asn Gln Ala Ala Thr Ala Ala Ala Lys Val Ala Arg Asp Phe Arg Arg
        35                  40                  45

Leu Asn Asn Ser Lys Arg Ala Ser Leu Leu Arg Thr Ile Ala Ser Glu
    50                  55                  60

Leu Glu Ala Arg Ser Asp Asp Ile Ile Ala Arg Ala His Leu Glu Thr
65                  70                  75                  80

Ala Leu Pro Glu Val Arg Leu Thr Gly Glu Ile Ala Arg Thr Ala Asn
                85                  90                  95

Gln Leu Arg Leu Phe Ala Asp Val Val Asn Ser Gly Ser Tyr His Gln
            100                 105                 110

Ala Ile Leu Asp Thr Pro Asn Pro Thr Arg Ala Pro Leu Pro Lys Pro
        115                 120                 125

Asp Ile Arg Arg Gln Gln Ile Ala Leu Gly Pro Val Ala Val Phe Gly
    130                 135                 140

Ala Ser Asn Phe Pro Leu Ala Phe Ser Ala Ala Gly Gly Asp Thr Ala
145                 150                 155                 160
```

```
Ser Ala Leu Ala Ala Gly Cys Pro Val Ile Val Lys Gly His Thr Ala
                165                 170                 175

His Pro Gly Thr Ser Gln Ile Val Ala Glu Cys Ile Glu Gln Ala Leu
            180                 185                 190

Lys Gln Glu Gln Leu Pro Gln Ala Ile Phe Thr Leu Leu Gln Gly Asn
        195                 200                 205

Gln Arg Ala Leu Gly Gln Ala Leu Val Ser His Pro Glu Ile Lys Ala
    210                 215                 220

Val Gly Phe Thr Gly Ser Val Gly Gly Gly Arg Ala Leu Phe Asn Leu
225                 230                 235                 240

Ala His Glu Arg Pro Glu Pro Ile Pro Phe Tyr Gly Glu Leu Gly Ala
                245                 250                 255

Ile Asn Pro Thr Phe Ile Phe Pro Ser Ala Met Arg Ala Lys Ala Asp
            260                 265                 270

Leu Ala Asp Gln Phe Val Ala Ser Met Thr Met Gly Cys Gly Gln Phe
        275                 280                 285

Cys Thr Lys Pro Gly Val Val Phe Ala Leu Asn Thr Pro Glu Thr Gln
    290                 295                 300

Ala Phe Ile Glu Thr Ala Gln Ser Leu Ile Arg Gln Gln Ser Pro Ser
305                 310                 315                 320

Thr Leu Leu Thr Pro Gly Ile Arg Asp Ser Tyr Gln Ser Gln Val Val
                325                 330                 335

Ser Arg Gly Ser Asp Asp Gly Ile Asp Val Thr Phe Ser Gln Ala Glu
            340                 345                 350

Ser Pro Cys Val Ala Ser Ala Leu Phe Val Thr Ser Ser Glu Asn Trp
        355                 360                 365

Arg Lys His Pro Ala Trp Glu Glu Glu Ile Phe Gly Pro Gln Ser Leu
    370                 375                 380

Ile Val Val Cys Glu Asn Val Ala Asp Met Leu Ser Leu Ser Glu Met
385                 390                 395                 400

Leu Ala Gly Ser Leu Thr Ala Thr Ile His Ala Thr Glu Glu Asp Tyr
                405                 410                 415

Pro Gln Val Ser Gln Leu Ile Pro Arg Leu Glu Glu Ile Ala Gly Arg
            420                 425                 430

Leu Val Phe Asn Gly Trp Pro Thr Gly Val Glu Val Gly Tyr Ala Met
        435                 440                 445

Val His Gly Gly Pro Tyr Pro Ala Ser Thr His Ser Ala Ser Thr Ser
    450                 455                 460

Val Gly Ala Glu Ala Ile His Arg Trp Leu Arg Pro Val Ala Tyr Gln
465                 470                 475                 480

Ala Leu Pro Glu Ser Leu Leu Pro Asp Ser Leu Lys Ala Glu Asn Pro
                485                 490                 495

Leu Glu Ile Ala Arg Ala Val Asp Gly Lys Ala Ala His Ser
            500                 505                 510
```

<210> SEQ ID NO 10
<211> LENGTH: 510
<212> TYPE: PRT
<213> ORGANISM: Vibrio harveyi

<400> SEQUENCE: 10

```
Met Asn Pro Gln Thr Asp Asn Val Phe Tyr Ala Thr Asn Ala Phe Thr
1               5                   10                  15
```

```
Gly Glu Ala Leu Pro Leu Ala Phe Pro Val His Thr Glu Val Glu Val
            20                  25                  30

Asn Gln Ala Ala Thr Ala Ala Ala Lys Val Ala Arg Asp Phe Arg Arg
        35                  40                  45

Leu Asn Asn Ser Lys Arg Ala Ser Leu Leu Arg Thr Ile Ala Ser Glu
    50                  55                  60

Leu Glu Ala Arg Ser Asp Asp Ile Ile Ala Arg Ala His Leu Glu Thr
65                  70                  75                  80

Ala Leu Pro Glu Val Arg Leu Thr Gly Glu Ile Ala Arg Thr Ala Asn
                85                  90                  95

Gln Leu Arg Leu Phe Ala Asp Val Val Asn Ser Gly Ser Tyr His Gln
            100                 105                 110

Ala Ile Leu Asp Thr Pro Asn Pro Thr Arg Ala Pro Leu Pro Lys Pro
        115                 120                 125

Asp Ile Arg Arg Gln Gln Ile Ala Leu Gly Pro Val Ala Val Phe Gly
    130                 135                 140

Ala Ser Asn Phe Pro Leu Ala Phe Ser Ala Ala Gly Gly Asp Thr Ala
145                 150                 155                 160

Ser Ala Leu Ala Ala Gly Cys Pro Val Ile Val Lys Gly His Gln Ala
                165                 170                 175

His Pro Gly Thr Ser Gln Ile Val Ala Glu Cys Ile Glu Gln Ala Leu
            180                 185                 190

Lys Gln Glu Gln Leu Pro Gln Ala Ile Phe Thr Leu Leu Gln Gly Asn
        195                 200                 205

Gln Arg Ala Leu Gly Gln Ala Leu Val Ser His Pro Glu Ile Lys Ala
    210                 215                 220

Val Gly Phe Thr Gly Ser Val Gly Gly Gly Arg Ala Leu Phe Asn Leu
225                 230                 235                 240

Ala His Glu Arg Pro Glu Pro Ile Pro Phe Tyr Gly Glu Leu Gly Ala
                245                 250                 255

Ile Asn Pro Thr Phe Ile Phe Pro Ser Ala Met Arg Ala Lys Ala Asp
            260                 265                 270

Leu Ala Asp Gln Phe Val Ala Ser Met Thr Met Gly Cys Gly Gln Phe
        275                 280                 285

Cys Thr Lys Pro Gly Val Val Phe Ala Leu Asn Thr Pro Glu Thr Gln
    290                 295                 300

Ala Phe Ile Glu Thr Ala Gln Ser Leu Ile Arg Gln Gln Ser Pro Ser
305                 310                 315                 320

Thr Leu Leu Thr Pro Gly Ile Arg Asp Ser Tyr Gln Ser Gln Val Val
                325                 330                 335

Ser Arg Gly Ser Asp Asp Gly Ile Asp Val Thr Phe Ser Gln Ala Glu
            340                 345                 350

Ser Pro Cys Val Ala Ser Ala Leu Phe Val Thr Ser Ser Glu Asn Trp
        355                 360                 365

Arg Lys His Pro Ala Trp Glu Glu Glu Ile Phe Gly Pro Gln Ser Leu
    370                 375                 380

Ile Val Val Cys Glu Asn Val Ala Asp Met Leu Ser Leu Ser Glu Met
385                 390                 395                 400

Leu Ala Gly Ser Leu Thr Ala Thr Ile His Ala Thr Glu Glu Asp Tyr
                405                 410                 415

Pro Gln Val Ser Gln Leu Ile Pro Arg Leu Glu Glu Ile Ala Gly Arg
            420                 425                 430
```

Leu Val Phe Asn Gly Trp Pro Thr Gly Val Glu Val Gly Tyr Ala Met
435 440 445

Val His Gly Gly Pro Tyr Pro Ala Ser Thr His Ser Ala Ser Thr Ser
450 455 460

Val Gly Ala Glu Ala Ile His Arg Trp Leu Arg Pro Val Ala Tyr Gln
465 470 475 480

Ala Leu Pro Glu Ser Leu Leu Pro Asp Ser Leu Lys Ala Glu Asn Pro
485 490 495

Leu Glu Ile Ala Arg Ala Val Asp Gly Lys Ala Ala His Ser
500 505 510

<210> SEQ ID NO 11
<211> LENGTH: 452
<212> TYPE: PRT
<213> ORGANISM: Lactobacillus sanfrancisco

<400> SEQUENCE: 11

Met Lys Val Ile Val Val Gly Cys Thr His Ala Gly Thr Phe Ala Val
1 5 10 15

Lys Gln Thr Ile Ala Asp His Pro Asp Ala Asp Val Thr Val Tyr Glu
20 25 30

Met Asn Asp Asn Ile Ser Phe Leu Ser Cys Gly Ile Ala Leu Tyr Leu
35 40 45

Gly Lys Glu Ile Lys Asn Asn Asp Pro Arg Gly Leu Phe Tyr Ser Ser
50 55 60

Pro Glu Glu Leu Ser Asn Leu Gly Ala Asn Val Gln Met Arg His Gln
65 70 75 80

Val Thr Asn Val Asp Pro Glu Thr Lys Thr Ile Lys Val Lys Asp Leu
85 90 95

Ile Thr Asn Glu Glu Lys Thr Glu Ala Tyr Asp Lys Leu Ile Met Thr
100 105 110

Thr Gly Ser Lys Pro Thr Val Pro Pro Ile Pro Gly Ile Asp Ser Ser
115 120 125

Arg Val Tyr Leu Cys Lys Asn Tyr Asn Asp Ala Lys Lys Leu Phe Glu
130 135 140

Glu Ala Pro Lys Ala Lys Thr Ile Thr Ile Ile Gly Ser Gly Tyr Ile
145 150 155 160

Gly Ala Glu Leu Ala Glu Ala Tyr Ser Asn Gln Asn Tyr Asn Val Asn
165 170 175

Leu Ile Asp Gly His Glu Arg Val Leu Tyr Lys Tyr Phe Asp Lys Glu
180 185 190

Phe Thr Asp Ile Leu Ala Lys Asp Tyr Glu Ala His Gly Val Asn Leu
195 200 205

Val Leu Gly Ser Lys Val Ala Ala Phe Glu Glu Val Asp Asp Glu Ile
210 215 220

Ile Thr Lys Thr Leu Asp Gly Lys Glu Ile Lys Ser Asp Ile Ala Ile
225 230 235 240

Leu Cys Ile Gly Phe Arg Pro Asn Thr Glu Leu Leu Lys Gly Lys Val
245 250 255

Ala Met Leu Asp Asn Gly Ala Ile Ile Thr Asp Glu Tyr Met His Ser
260 265 270

Ser Asn Arg Asp Ile Phe Ala Ala Gly Asp Ser Ala Ala Val His Tyr
275 280 285

Asn Pro Thr Asn Ser Asn Ala Tyr Ile Pro Leu Ala Thr Asn Ala Val
290 295 300

```
Arg Gln Gly Arg Leu Val Gly Leu Asn Leu Thr Glu Asp Lys Val Lys
305                 310                 315                 320

Asp Met Gly Thr Gln Ser Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
            340                 345                 350

Lys Val Ser Glu Val Ile Ile Ala Asp Asn Tyr Arg Pro Glu Phe Met
        355                 360                 365

Leu Ser Thr Asp Glu Val Leu Met Ser Leu Val Tyr Asp Pro Lys Thr
    370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
        435                 440                 445

Lys Ala His Lys
    450


<210> SEQ ID NO 12
<211> LENGTH: 507
<212> TYPE: PRT
<213> ORGANISM: Rhodococcus erythropolis

<400> SEQUENCE: 12

Met Thr Val Tyr Ala Arg Pro Gly Thr Ala Asp Ala Ile Met Ser Phe
1               5                   10                  15

Gln Ser Arg Tyr Asp Asn Trp Ile Gly Asn Glu Trp Val Ala Pro Val
            20                  25                  30

Lys Gly Gln Tyr Phe Glu Asn Pro Thr Pro Val Thr Gly Gln Asn Phe
        35                  40                  45

Cys Asp Val Ala Arg Ser Thr Ala Glu Asp Ile Glu Leu Ala Leu Asp
    50                  55                  60

Ala Ala His Ala Ala Ala Pro Ala Trp Gly Lys Thr Ser Val Ala Glu
65                  70                  75                  80

Arg Ala Ile Ile Leu Asn Lys Ile Ala Asp Arg Met Glu Glu Asn Leu
                85                  90                  95

Glu Ser Ile Ala Leu Ala Glu Ser Trp Asp Asn Gly Lys Pro Ile Arg
            100                 105                 110

Glu Thr Leu Asn Ala Asp Ile Pro Leu Ala Ile Asp His Phe Arg Tyr
        115                 120                 125

Phe Ala Gly Ala Ile Arg Ala Gln Glu Gly Ser Leu Ser Glu Ile Asn
    130                 135                 140

Ser Asp Thr Val Ala Tyr His Phe His Glu Pro Leu Gly Val Val Gly
145                 150                 155                 160

Gln Ile Ile Pro Trp Asn Phe Pro Ile Leu Met Ala Val Trp Lys Leu
                165                 170                 175

Ala Pro Ala Leu Ala Ala Gly Asn Ala Ile Val Leu Lys Pro Ala Glu
            180                 185                 190

Gln Thr Pro Val Ser Ile Leu His Leu Ile Gly Ile Ile Gly Asp Leu
        195                 200                 205
```

-continued

Leu Pro Ala Gly Val Leu Asn Ile Val Asn Gly Phe Gly Val Glu Ala
    210                 215                 220

Gly Lys Pro Leu Ala Ser Ser Pro Arg Ile Lys Lys Ile Ala Phe Thr
225                 230                 235                 240

Gly Glu Thr Thr Thr Gly Arg Leu Ile Met Gln Tyr Ala Ser Gln Asn
                245                 250                 255

Leu Ile Pro Val Thr Leu Glu Leu Gly Gly Lys Ser Pro Asn Ile Phe
            260                 265                 270

Phe Ser Asp Val Leu Ala Ser Asn Asp Asp Tyr Gln Asp Lys Ala Leu
        275                 280                 285

Glu Gly Phe Thr Met Phe Ala Leu Asn Gln Gly Glu Val Cys Thr Cys
    290                 295                 300

Pro Ser Arg Ser Leu Ile Gln Glu Asp Ile Phe Asp Glu Phe Leu Ala
305                 310                 315                 320

Met Ala Ala Ile Arg Thr Lys Ala Val Arg Gln Gly Asp Pro Leu Asp
                325                 330                 335

Thr Asp Thr Met Ile Gly Ala Gln Ala Ser Asn Asp Gln Leu Glu Lys
            340                 345                 350

Ile Leu Ser Tyr Ile Glu Ile Gly Lys Ala Glu Gly Ala Lys Val Ile
        355                 360                 365

Thr Gly Gly Glu Arg Ala Glu Leu Gly Gly Asp Leu Ser Gly Gly Tyr
    370                 375                 380

Tyr Val Gln Pro Thr Val Phe Thr Gly Asn Asn Lys Met Arg Ile Phe
385                 390                 395                 400

Gln Glu Glu Ile Phe Gly Pro Val Val Ser Val Thr Ser Phe Lys Asp
                405                 410                 415

Tyr Asp Glu Ala Ile Glu Ile Ala Asn Asp Thr Leu Tyr Gly Leu Gly
            420                 425                 430

Ala Gly Val Trp Ser Arg Asp Gly Gly Val Ala Tyr Arg Ala Gly Arg
        435                 440                 445

Asp Ile Gln Ala Gly Arg Val Trp Thr Asn Thr Tyr His Gln Tyr Pro
    450                 455                 460

Ala His Ala Ala Phe Gly Gly Tyr Lys Gln Ser Gly Ile Gly Arg Glu
465                 470                 475                 480

Asn His Leu Met Met Leu Ser His Tyr Gln Gln Thr Lys Asn Leu Leu
                485                 490                 495

Val Ser Tyr Ala Gln Lys Ala Gln Gly Phe Phe
            500                 505

<210> SEQ ID NO 13
<211> LENGTH: 506
<212> TYPE: PRT
<213> ORGANISM: Geobacillus thermodenitrificans

<400> SEQUENCE: 13

Met Ile Tyr Ala Gln Pro Gly Gln Pro Gly Ala Leu Val Thr Phe Lys
1               5                   10                  15

Lys Arg Tyr Glu Asn Phe Ile Gly Gly Lys Trp Val Pro Pro Val Asp
            20                  25                  30

Gly Glu Tyr Phe Glu Asn Ile Thr Pro Ile Thr Gly Lys Pro Tyr Cys
        35                  40                  45

Glu Val Pro Arg Ser Lys Ala Ala Asp Ile Glu Leu Ala Leu Asp Ala
    50                  55                  60

```
Ala His Ala Ala Lys Asp Glu Trp Gly Arg Thr Ser Pro Ala Lys Arg
65                  70                  75                  80

Ala Arg Leu Leu Asn Lys Ile Ala Asp Arg Met Glu Glu Asn Leu Glu
                85                  90                  95

Leu Leu Ala Val Ala Glu Thr Trp Glu Asn Gly Lys Pro Ile Arg Glu
            100                 105                 110

Thr Leu Ala Ala Asp Ile Pro Leu Ala Ile Asp His Phe Arg Tyr Phe
        115                 120                 125

Ala Ser Cys Ile Arg Ala Gln Glu Gly Thr Ile Ser Glu Ile Asp His
    130                 135                 140

Asp Thr Val Ala Tyr His Phe Lys Glu Pro Leu Gly Val Val Gly Gln
145                 150                 155                 160

Ile Ile Pro Trp Asn Phe Pro Ile Leu Met Ala Ala Trp Lys Leu Ala
                165                 170                 175

Pro Ala Leu Ala Ala Gly Asn Cys Val Val Leu Lys Pro Ala Glu Gln
            180                 185                 190

Thr Pro Thr Ser Ile Leu Val Leu Ile Glu Leu Ile Glu Asp Leu Leu
        195                 200                 205

Pro Pro Gly Val Val Asn Ile Val Asn Gly Phe Gly Leu Glu Ala Gly
    210                 215                 220

Lys Pro Leu Ala Ser Asn Pro Arg Val Ala Lys Val Ala Phe Thr Gly
225                 230                 235                 240

Glu Thr Thr Thr Gly Arg Leu Ile Met Gln Tyr Ala Ser Gln Asn Ile
                245                 250                 255

Val Pro Val Thr Leu Glu Leu Gly Gly Lys Ser Pro Asn Ile Phe Phe
            260                 265                 270

Ala Asp Val Met Asp Lys Asp Asp Glu Phe Phe Asp Lys Ala Leu Glu
        275                 280                 285

Gly Phe Thr Met Phe Ala Leu Asn Gln Gly Glu Val Cys Thr Cys Pro
    290                 295                 300

Ser Arg Ala Leu Ile His Glu Ser Ile Tyr Asp Ala Phe Met Glu Arg
305                 310                 315                 320

Ala Leu Glu Arg Val Lys Gln Ile Lys Gln Gly Asn Pro Leu Asp Thr
                325                 330                 335

Glu Thr Met Ile Gly Ala Gln Ala Ser Ser Glu Gln Leu Glu Lys Ile
            340                 345                 350

Leu Ser Tyr Ile Asp Ile Gly Lys Gln Glu Gly Ala Glu Leu Leu Ile
        355                 360                 365

Gly Gly Glu Arg Asn Met Leu Glu Gly Glu Leu Ala Gly Gly Tyr Tyr
    370                 375                 380

Val Lys Pro Thr Ile Phe Lys Gly His Asn Lys Met Arg Ile Phe Gln
385                 390                 395                 400

Glu Glu Ile Phe Gly Pro Val Leu Ala Val Thr Thr Phe Lys Asp Glu
                405                 410                 415

Asp Glu Ala Leu Ala Ile Ala Asn Glu Thr Leu Tyr Gly Leu Gly Ala
            420                 425                 430

Gly Val Trp Thr Arg Asn Ile Asn Thr Ala Tyr Arg Phe Gly Arg Gly
        435                 440                 445

Ile Gln Ala Gly Arg Val Trp Thr Asn Cys Tyr His Val Tyr Pro Ala
    450                 455                 460

His Ala Ala Phe Gly Gly Tyr Lys Met Ser Gly Ile Gly Arg Glu Thr
465                 470                 475                 480
```

His Lys Met Met Leu Asp His Tyr Gln Gln Thr Lys Asn Met Leu Val
485 490 495

Ser Tyr Ser Pro Lys Lys Leu Gly Leu Phe
500 505

<210> SEQ ID NO 14
<211> LENGTH: 506
<212> TYPE: PRT
<213> ORGANISM: Marinobacter aquaeolei

<400> SEQUENCE: 14

Met Ile Tyr Ala Gln Pro Gly Gln Glu Gly Ser Val Val Ser Phe Lys
1 5 10 15

Ser Arg Tyr Glu Asn Tyr Ile Gly Gly Glu Trp Val Ala Pro Val Lys
20 25 30

Gly Gln Tyr Phe Asp Asn Ile Thr Pro Val Thr Gly Ala Val Phe Cys
35 40 45

Glu Val Pro Arg Ser Thr Ala Glu Asp Ile Asp Leu Ala Leu Asp Ala
50 55 60

Ala His Lys Ala Ala Pro Ala Trp Gly Lys Thr Ser Pro Thr Glu Arg
65 70 75 80

Ser Asn Ile Leu Leu Lys Ile Ala Asp Arg Ile Glu Ala Asn Leu Glu
85 90 95

Lys Leu Ala Val Ala Glu Thr Trp Asp Asn Gly Lys Ala Val Arg Glu
100 105 110

Thr Leu Asn Ala Asp Val Pro Leu Ala Ala Asp His Leu Arg Tyr Phe
115 120 125

Ala Gly Cys Ile Arg Ala Gln Glu Gly His Met Ser Glu Ile Asp His
130 135 140

Asn Thr Val Ala Tyr His Phe His Glu Pro Leu Gly Val Val Gly Gln
145 150 155 160

Ile Ile Pro Trp Asn Phe Pro Leu Leu Met Ala Ala Trp Lys Leu Gly
165 170 175

Pro Cys Leu Ala Ser Gly Asn Cys Thr Val Leu Lys Pro Ala Glu Gln
180 185 190

Thr Pro Ala Ser Ile Leu Val Leu Met Asp Ile Ile Gly Asp Leu Leu
195 200 205

Pro Pro Gly Val Ile Asn Ile Val Asn Gly Tyr Gly Ile Glu Ala Gly
210 215 220

Gln Ala Leu Ala Thr Ser Lys Arg Ile Ala Lys Ile Ala Phe Thr Gly
225 230 235 240

Ser Thr Pro Val Gly Ser His Ile Leu Lys Cys Ala Ala Glu Asn Ile
245 250 255

Ile Pro Ser Thr Val Glu Leu Gly Gly Lys Ser Pro Asn Ile Tyr Phe
260 265 270

Ser Asp Val Met Lys Ala Glu Pro Glu Phe Val Asp Lys Cys Val Glu
275 280 285

Gly Leu Val Leu Ala Phe Phe Asn Gln Gly Glu Ile Cys Thr Cys Pro
290 295 300

Ser Arg Ala Leu Val Gln Glu Asp Met Phe Glu Glu Phe Met Gln Lys
305 310 315 320

Val Val Glu Arg Thr Lys Ser Ile Lys Arg Gly Asn Pro Leu Asp Thr
325 330 335

Asp Val Gln Val Gly Ala Gln Ala Ser Lys Glu Gln Phe Asp Lys Ile
340 345 350

```
Met Ser Tyr Met Glu Ile Gly Arg Gln Glu Gly Ala Val Val Leu Thr
        355                 360                 365

Gly Gly Asp Arg Glu His Leu Glu Gly Glu Phe Asn Asn Gly Phe Tyr
    370                 375                 380

Ile Gln Pro Thr Leu Phe Lys Gly Asp Asn Lys Met Arg Val Phe Gln
385                 390                 395                 400

Glu Glu Ile Phe Gly Pro Val Val Gly Val Thr Thr Phe Lys Thr Glu
                405                 410                 415

Glu Glu Ala Leu Ala Ile Ala Asn Asp Thr Glu Phe Gly Leu Gly Ala
            420                 425                 430

Gly Val Trp Thr Arg Asp Thr Asn Leu Ala Tyr Arg Met Gly Arg Asn
        435                 440                 445

Ile Gln Ala Gly Arg Val Trp Met Asn Cys Tyr His Ala Tyr Pro Ala
    450                 455                 460

His Ala Ala Phe Gly Gly Tyr Lys Lys Ser Gly Ile Gly Arg Glu Asn
465                 470                 475                 480

His Lys Met Ala Leu Glu His Tyr Gln Gln Thr Lys Cys Met Leu Thr
                485                 490                 495

Ser Tyr Asp Thr Asn Pro Leu Gly Phe Phe
            500                 505


<210> SEQ ID NO 15
<211> LENGTH: 24
<212> TYPE: DNA
<213> ORGANISM: Artificial Sequence
<220> FEATURE:
<223> OTHER INFORMATION: Forward Primer

<400> SEQUENCE: 15

taaaggtcat caggcacatc cggg                                              24


<210> SEQ ID NO 16
<211> LENGTH: 19
<212> TYPE: DNA
<213> ORGANISM: Artificial Sequence
<220> FEATURE:
<223> OTHER INFORMATION: Reverse Primer

<400> SEQUENCE: 16

acaataaccg gacaacctg                                                    19


<210> SEQ ID NO 17
<211> LENGTH: 1896
<212> TYPE: DNA
<213> ORGANISM: Arabidopsis thaliana

<400> SEQUENCE: 17

atgggcttta gcccgagcag cagctggttt ctgcatccgc agctgcatca tgtggtgagc      60

aaaatgagct attttgatgc gtttctgttt tatattgtgc atctggtgga taaactgggc     120

ctgtggcatc gctttccggt gctgctgggc gtggcgtatc tgggcctgcg ccgccatctg     180

catcagcgct ataacctggt gcatgtgggc ccgattaacg gccagggcta tgataccgat     240

gaattttgct atcgcaccgc ggatggcaaa tgcaaccatc cgagcgataa caccattggc     300

agccagggca gctttattgg ccgcaacatg ccgccgagca ccagccagta tggcattctg     360

gatccgcatc cgagcgtggt ggcgaccaaa ctgctggcgc gcaaacgctt tattgataac     420

ggcgatcagt ttaacgtgat tgcgtgcagc tggattcagt ttatgattca tgattgggtg     480
```

-continued gatcatctgg aagataccca tcagattgaa ctggaagcgc cggaagaagt ggcgagcggc 540
tgcccgctga aaagctttaa atttctgcgc accaaaaaag tgccgaccga tgatcatcat 600
aaaagcggcg cggtgaacac ccgcaccccg tggtgggatg gcagcgtgat ttatggcaac 660
gatgaaaccg gcatgcgccg cgtgcgcgtg tttaaagatg gcaaactgaa aattagcggc 720
gatggcctgc tggaacgcga tgaacgcggc gtgccgatta gcggcgatat tcgcaacagc 780
tggagcggct ttagcctgct gcaggcgctg tttgtgaaag aacataacag cgtgtgcgat 840
atgctgaaag aacgctatcc ggattttgat gatgaaaaac tgtatcgcac cgcgcgcctg 900
gtgaccgcgg cggtgattgc gaaagtgcat accattgatt ggaccattga actgctgaaa 960
accgataccc tgaccgcggg catgcgcatt aactggtatg gctttttggg caaaaaagtg 1020
aaagatatgg tgggcgcgcg ctttggcccg ctgtttagcg gcctggtggg cctgaaaaaa 1080
ccgaacgatc atggcgtgcc gtatagcctg accgaagaat ttgtgagcgt gtatcgcatg 1140
cattgcctgc tgccggaaac cctgattctg cgcgatatga acagcgaaaa cgtggataaa 1200
gaaaacccgg cgattgaacg cgaaattccg atgaccgaac tgattggcaa aaaagcgggc 1260
gaaaaagcga gcaaactggg ctttgaacag ctgctggtga gcatgggcca tcagagctgc 1320
ggcgcgctga ccctgtggaa ctatccgaac tggatgcgca acctggtggc gcaggatatt 1380
gatggcgaag atcgcccgca tctgattgat atggcggcgc tggaaattta tcgcgatcgc 1440
gaacgcggcg tgccgcgcta taacgaattt cgcaaaaacc tgctgatgag cccgattagc 1500
aaatgggaag aactgaccga tgatgaagaa gcgattaaag tgctgcgcga agtgtatgaa 1560
gatgatattg aaaaactgga tctgaacgtg ggcctgcatg cggaaaaaaa aattaaaggc 1620
tttgcgatta gcgaaaccgc gtttttttatt tttctgctgg tggcgagccg ccgcctggaa 1680
gcggatcgct tttttaccac caactttaac gaaaaaacct ataccaaaga aggcctggaa 1740
tgggtgaaca ccaccgaaac cctgaaagat gtgattgatc gccattttcc gcgcctgacc 1800
gatcagtgga tgcgctgcag cagcgcgttt agcgtgtggg gcagcgatcc gaacccgaaa 1860
aactgggtgc cgctgtatct gcgcagcgcg ccgtaa 1896

<210> SEQ ID NO 18
<211> LENGTH: 1920
<212> TYPE: DNA
<213> ORGANISM: Arabidopsis thaliana

<400> SEQUENCE: 18
atgaaagtga ttaccagcct gattagcagc attctgctga aatttattca taaagatttt 60
catgaaattt atgcgcgcat gagcctgctg gatcgctttc tgctgctgat tgtgcatggc 120
gtggataaaa tggtgccgtg gcataaactg ccggtgtttc tgggcctgac ctatctggaa 180
gtgcgccgcc atctgcatca gcagtataac ctgctgaacg tgggccagac cccgaccggc 240
attcgctttg atccggcgaa ctatccgtat cgcaccgcgg atggcaaatt taacgatccg 300
tttaacgaag gcgtgggcag ccagaacagc ttttttggcc gcaactgccc gccggtggat 360
cagaaaagca aactgcgccg cccggatccg atggtggtgg cgaccaaact gctgggccgc 420
aaaaaattta ttgataccgg caaacagttt aacatgattg cggcgagctg gattcagttt 480
atgattcatg attggattga tcatctggaa gatacccatc agattgaact ggtggcgccg 540
aaagaagtgg cgagcaaatg cccgctgagc agctttcgct ttctgaaaac caaagaagtg 600
ccgaccggct tttttgaaat taaaaccggc agccagaaca ttcgcacccc gtggtgggat 660
agcagcgtga tttatggcag caacagcaaa accctggatc gcgtgcgcac ctataaagat 720

```
ggcaaactga aaattagcga agaaaccggc ctgctgctgc atgatgaaga tggcctggcg    780
attagcggcg atattcgcaa cagctgggcg ggcgtgagcg cgctgcaggc gctgtttatt    840
aaagaacata acgcggtgtg cgatgcgctg aaagatgaag atgatgatct ggaagatgaa    900
gatctgtatc gctatgcgcg cctggtgacc agcgcggtgg tggcgaaaat tcataccatt    960
gattggaccg tgcagctgct gaaaaccgat accctgctgg cgggcatgcg cgcgaactgg   1020
tatggcctgc tgggcaaaaa atttaaagat agctttggcc atgcgggcag cagcattctg   1080
ggcggcgtgg tgggcatgaa aaaaccgcag aaccatggcg tgccgtatag cctgaccgaa   1140
gattttacca gcgtgtatcg catgcatagc ctgctgccgg atcagctgca tattctggat   1200
attgatgatg tgccgggcac caacaaaagc ctgccgctga ttcaggaaat tagcatgcgc   1260
gatctgattg gccgcaaagg cgaagaaacc atgagccata ttggctttac caaactgatg   1320
gtgagcatgg gccatcaggc gagcggcgcg ctggaactga tgaactatcc gatgtggctg   1380
cgcgatattg tgccgcatga tccgaacggc caggcgcgcc cggatcatgt ggatctggcg   1440
gcgctggaaa tttatcgcga tcgcgaacgc agcgtgccgc gctataacga atttcgccgc   1500
agcatgttta tgattccgat taccaaatgg gaagatctga ccgaagatga agaagcgatt   1560
gaagtgctgg atgatgtgta tgatggcgat gtggaagaac tggatctgct ggtgggcctg   1620
atggcggaaa aaaaaattaa aggctttgcg attagcgaaa ccgcgtttta tatttttctg   1680
attatggcga cccgccgcct ggaagcggat cgcttttttta ccagcgattt taacgaaacc   1740
atttatacca aaaaaggcct ggaatgggtg aacaccaccg aaagcctgaa agatgtgatt   1800
gatcgccatt atccggatat gaccgataaa tggatgaaca gcgaaagcgc gtttagcgtg   1860
tgggatagcc cgccgctgac caaaaacccg attccgctgt atctgcgcat tccgagctaa   1920
```

<210> SEQ ID NO 19
<211> LENGTH: 1932
<212> TYPE: DNA
<213> ORGANISM: Capsicum annuum

<400> SEQUENCE: 19

```
atgagcttta ttatgagcag cctgcgcaac ctgtttctga gcccgctgcg cagctttatt     60
cagaaagatt ttcatgatgc gtttgatagc atgaccctgc tggataaact gctgtttatg    120
atggtgcatt ttgtggataa actgattctg tggcatcgcc tgccggtgtt tctgggcctg    180
gcgtatctgg cggcgcgccg ccatctgcat caggaatata acctgattaa cgtgggccgc    240
accccgaccg gcgtgcgcag caacccggaa gattatccgt atcgcaccgc ggatggcaaa    300
tataacgatc cgtttaacga aggcgcgggc agccagttta gctttttttgg ccgcaacgtg    360
atgccggtgg atcagcatga taaactgaaa aaaccggatc cgatggtggt ggcgaccaaa    420
ctgctggcgc gcaaaaactt tatggatacc ggcaaacagt ttaacatgat tgcggcgagc    480
tggattcagt ttatgattca tgattggatt gatcatctgg aagataccca tcagattgaa    540
ctgcgcgcgc cggaagaagt ggcgagcgaa tgcccgctga aaagctttaa attttataaa    600
agcaaaaaaa ccccgaccgg cttttatgaa attaaaaccg gctatctgaa ccgccgcacc    660
ccgtggtggg atggcagcgc gatttatggc agcaacaccg aagcgctgaa aaaagtgcgc    720
acctttgaag atggcaaact gaaactgagc gcggatggcc tgctggaaca ggatgaaaac    780
ggcaacatta ttagcggcga tgtgcgcaac ccgtgggcgg gcctgctggc gctgcaggcg    840
ctgtttattc aggaacataa cctggtgtgc gataccctga aaaaagaata tccgaaactg    900
```

gaagatgaag atctgtatcg ccatgcgcgc ctggtgacca gcgcggtgat tgcgaaagtg 960
cataccattg attggaccgt ggaactgctg aaaaccgata ccctgctgag cggcatgcgc 1020
gcgaactggt atggcctgct gggcaaaaaa tttaaagata cctttggcca tgtgggcggc 1080
agcagcctgg gcggctttgt gggcatgaaa aaaccggaaa accatggcgt gccgtatagc 1140
ctgaccgaag aatttgtgag cgtgtatcgc atgcatcagc tgctgccgga taccctgcag 1200
ctgcgcaaca ttgatgcgac cccgggcccg aacaaaagcc tgccgctgac caacgaaatt 1260
ccgatggaag atctgattgg cggcaaaggc gaagaaaacc tgagccgcat tggctatacc 1320
aaacagatgg tgagcatggg ccatcaggcg tgcggcgcgc tggaactgat gaactatccg 1380
atttggatgc gcgatctgat tccgcaggat gtggatggca acgatcgccc ggatcatatt 1440
gatctggcgg cgctggaaat ttatcgcgat cgcgaacgca gcgtggcgcg ctataacgaa 1500
tttcgccgcc gcatgctgca gattccgatt agcaaatggg aagatctgac cgatgatgaa 1560
gaagcgatta aaatgctgcg cgaagtgtat ggcgatgatg tggaagaact ggaatttgtg 1620
agcggcaacg tgtgcggcga aaaagataaa ggctttgcga ttagcgaaac cgcgtttttt 1680
atttttctga ttatggcgag ccgccgcctg gaagcggata aatttttac cagcaactat 1740 aacgaagaaa cctataccaa aaaaggcctg gaatgggtga acaccaccga aagcctgaaa 1800
gatgtgctgg atcgccatta tccggaaatg accggcaaat ggatgaacag caacagcgcg 1860
tttagcgtgt gggatagcag cccggaaccg cataacccga ttccgattta ttttcgcgtg 1920
ccgcagcagt aa 1932

<210> SEQ ID NO 20
<211> LENGTH: 1956
<212> TYPE: DNA
<213> ORGANISM: Cercospora beticola

<400> SEQUENCE: 20
atggcggcgc atccgagcca gctgtgcatt gatcgcgcgg tgggcccgct gccgcatctg 60
gcgagctatc cgccgtgccc gctggcgatt accatggtgt atacctttgg ccagcgcgtg 120
ctggtggcgc tgtttaaagc ggtgaacgcg attattgcgt ggcataaact gccgccgctg 180
attggcgcgc tgaacctgct ggcgctgcgc gatgaactgc gcgaaaaaaa cctgtatgat 240
acctatccga ccgaagattt tcagggcacc accaaaagcg atccgattgt ggataccaaa 300
tttatttgcg cgcgcaacag cgatggcctg cataacgatc tggaacgccc gaaaatgggc 360
tgcgcggcga tgcgctttgg ccgcaacgtg ccgcgccagt ataccgcgcc gccgagcgat 420
catgatctga tgaccccgga tccgcgcctg gtgagcgcga aactgctgca gcgcaccgaa 480
tttaaaccgg cgaccattgt gaacctgctg gcggcggcgt ggattcagtt tcaggtgcat 540
gattgggcgc agcataccaa cagcaaaacc aaatttcatc atattccgct gaaagcggat 600
gatccgtggc cggaaaaccc gatgaaagtg gcgaaaaccg tgcaggatga accgctggat 660
gaagaagatc agaaatatcc ggcgtataaa aacgaaaaca cccattggtg ggatgcgagc 720
cagatttatg gcagcaccga agaagcgacc cgcaaactgc gcggcaaaca tcaggatggc 780
accctggatg tggatcgcat tgaaggcgaa cattttctgc cgcgcggcca tgatggcatt 840
ccgaaaaccg gctttaaaga aaactggtgg ctgggcctgg aactgctgca taccctgttt 900
gcgctggaac ataacgcgat ttgcagcatg ctgaaaacca aaaacccgag ctggagcggc 960
gatgaaattt ttgatgtggc gcgcctgatt aactgcgcgc tgatggcgaa aattcatacc 1020
attgaatgga ccccggcgat tctgccgcat ccgaccctgg atattggcat gaacgcgaac 1080

```
tggagcggcc tgctgggccc gagctggagc aaactgttta gcaactttgg caaaagcgaa   1140
gcgtttaccg gcattccgga aagcggcgcg gatagcggca aaaccccgta ttgcctgacc   1200
gaagaatttg tgagcgtgta tcgcctgcat agcctgattc cggatgatgt ggcgtttttt   1260
aaactgcgca ccggcgaaca taccagcaac attccgattc aggatattgc gtttgaaaac   1320
gcgcgcagcg tgtttgaagg cccgcagaac ctgaactttg cggatgcgtt ttatagcttt   1380
ggcattaact ttccgggcgc gattaccgcg cataacatgc cgagctttct gcgcgatctg   1440
aaaaaaccgg atggcgaaca tctggatatg ggctgcgtgg atgtgctgcg cgatcgcgaa   1500
cgcggcgtgc cgcgctattg ccagtttcgc cgcctgtttc atatgccggt gccgaaaagc   1560
tttagcgcgc tgaccggcgg caacgcgacc ctggcgaccg aactgagcca ggtgtatgat   1620
ggcgatattg aaaaagtgga tctgctgatt ggctgcctgt gcgaaccgct gccgaaaggc   1680
tttggcttta gcgataccgc gtttcgcgtg tttattctga tggcgagccg ccgcctgaaa   1740
agcgatcgct ttattgcgag cgattttaaa catgaaattt ataccaaaga aggcattgat   1800
tgggtgcagg ataacgatat gcgcgatgtg ctggtgcgcc attttccgga tctgcgcgcg   1860
ccgctgaaag atgtgaaaaa cgcgtttgcg ccgtggggca aagtgggccg caccgaagaa   1920
tatcgcggcg tgcagattac cgcgccggaa aaataa                             1956
```

<210> SEQ ID NO 21
<211> LENGTH: 1899
<212> TYPE: DNA
<213> ORGANISM: Cucumis sativus

<400> SEQUENCE: 21

```
atgggctttg cgctgtttag cagcccgttt gtgcatccgc agctgcagca gattgtggcg     60
aaaatgaccc tgctggatac cctgctgttt tatgtggtgc attttgtgga taaactgggc    120
ctgtggcatc gcctgccggt gctgctgggc ctggcgtatc tgggcatgcg ccgccatctg    180
catcagcgct ataacctgct gcatgtgggc agcatgtatg gccagaaata tgatcatcag    240
cagttttgct atcgcaccgc ggatggcagc tgcaaccatc cgtttgatag cctggtgggc    300
agccagggca cctttttgg ccgcaacatg ccgccgagca acagcccgta tggcgtgctg     360
gatccgcatc cgaccgtggt ggcgaccaaa ctgctggaac gcaaaaaata tattgataac    420
ggcaaacagt ttaacatgat tgcgtgcagc tggattcagt ttatgattca tgattggatt    480
gatcatctgg aagataccaa acaggtggaa ctgaccgcgc cggaagaagt ggcgaacggc    540
tgcccgctga aaagctttaa attttttggc accaaagtgg tgagcaccga tagcccgtat    600
ctgaaaaccg gcaccctgaa cacccgcacc ccgtggtggg atggcagcgt gatttatggc    660
aacaacgaag aaggcatgcg ccgcgtgcgc gcgtttcagg atggcaaaat gaaaattgcg    720
ggcgatggcc tgctggaaca tgatgaaaaa ggcattccga ttagcggcga tgtgcgcaac    780
tgctgggcgg gctttagcct gctgcaggcg ctgtttgtga aagaacataa cgcggtgtgc    840
gatatgctga aagaacgcta tccggatctg gatgatgaac agctgtatcg ccatgcgcgc    900
ctggtgacca gcgcggtgat tgcgaaaatt cataccattg attggaccgt ggaactgctg    960
aaaaccgaaa ccctgctggc gggcatgcgc attaactggt atggctttct gggcaaaaaa   1020
tttaaagata cctttggcca tatttgcggc ccgattctga gcggcctggt gggcctgaaa   1080
aaaccgcgcg atcatggcat tccgtatagc ctgaccgaag aatttgtgag cgtgtatcgc   1140
atgcattgcc tgctgccgga taccctggtg attcgcgatc tgaacagcac caacagcgat   1200
```

tatagcgatc cgccgattat tgaagaagtg ccgatggaac agctggtggg caaagatggc 1260
gaaaaacgca gcgcgaaact gggcatggaa cagatgctgg tgagcatggg ccatcaggcg 1320
tgcggcgcgc tgagcctgtg gaactatccg agctggatgc gcaaactgat tgcgcatgat 1380
gtggatggcg atgatcgccc ggatccggtg gatatggcgg cgatggaaat ttatcgcgat 1440
cgcgaacgcg gcgtggcgcg ctataacgaa tttcgccgca acctgctgat gagcccgatt 1500
agcaaatggg aagatctgac cgatgataac gaagtggtga gcgcgctgga agaagtgtat 1560
ggcaacgatg tggaaaaact ggatctgctg gtgggcctgc atgcggaaaa aaaaattaaa 1620
ggctttgcga ttagcgaaac cagctttttt atttttctgc tgattgcgag ccgccgcctg 1680
gaagcggatc gctttttttac caccaactat aacagcaaaa cctataccga agaaggcctg 1740
gaatgggtga acaaaaccga aaccctgaaa gatgtgattg atcgccattt tccggatatg 1800
accaaacgct ggatgcgctg cagcagcgcg tttagcgtgt gggatagcct gccgaacccg 1860
accaactata ttccgctgta tctgcgcccg gcgacctaa 1899

<210> SEQ ID NO 22
<211> LENGTH: 1932
<212> TYPE: DNA
<213> ORGANISM: Cucumis sativus

<400> SEQUENCE: 22
atgctgagcc agctgctgaa accgattaaa attgtgctgc gcggcgaact gcagaaattt 60
gtgcataaag attttcatga agtggtgcag cgcatgaccg tgattgatac ctttctgttt 120
ctgattgtgc attttgtgga taaactgggc atttggcata aactgccggt gattctgggc 180
ctgctgtatc tggcggtgcg ccgccatctg catcaggaat ataacctgtt taacgtgggc 240
cgcaccccgg tgggcgtgcg ctttaacccg gtggattttc cgtatcgcac cgcggatggc 300
aaatataacg atccgtttaa cgaaggcgcg ggcgcgcagg gcagcttttt tggccgcaac 360
attcatccgg tggatcagag caaaaccctg ctgaaaccgg atccgatggt ggtggcgacc 420
aaactgctgg cgcgccgcaa actgattgat accggcaaac agtttaacat gattgcggcg 480
agctggattc agtttatgat tcatgattgg attgatcatc tggaagatac caaacaggtg 540
gaactggtgg cgccgcgcga agtggcgagc gaatgcccgc tgaaaagctt taaatttttt 600
aaaaccaaac aggtgagcac cggctttttt gataacaaaa ccggcagcat taacgtgcgc 660
accccgtggt gggatggcag cgtgctgtat ggcagcaacg cggaaaaact gggcaaagtg 720
cgcacctata aagatggcaa actgaaaatt gcggatgatg atctgctgct gcatgataac 780
gatggcgtgg cgattagcgg cgatgtgcgc aacagctggg cgggcgtgag caccctgcag 840
gcgctgttta ttcgcgaaca taacgcggtg tgcgatgcgc tgaaaaaaga agatgaagat 900
ctggaagatg aagatctgta tcgctatgcg cgcctggtga ccagcgcggt gattgcgaaa 960
gtgcatacca ttgattggac cgtggaactg ctgaaaatgg ataccctgct ggcgggcatg 1020
cgcggcaact ggtatggcct gctgggcaaa aaatttaaag atacctttgg ccatgtgggc 1080
ggcgcgattc tgggcggcct ggtgggcctg aaaaaaccgg ataaccatgg cgtgccgtat 1140
agcctgaccg aagaatttgc gagcgtgtat cgcatgcata gcctgctgcc ggatgatttt 1200
catctgcgcg atattagcgt ggatccggat cataacaaaa gcccgccgct ggtggaaaaa 1260
gtgccgatgg cgaacatgat tggccataaa ggcgaagaaa ccagcaaaaa aatgggcttt 1320
accgcgctgc tggtgagcat gggccatcag agcagcggcg cgctggaact gtggaactat 1380
ccgcagtggc tgcgcgatct gattccgcat gatatggatg gcaaagatcg cgcggatcat 1440
attgatctgg cggcgctgga agtgtatcgc gatcgcgaac gccgcgtggc gcgctataac 1500
gattttcgcc gcggcctgtt tctgattccg attagcaaat gggaagatct gaccgatgat 1560
gaaggcgcga ttgaagtgct gcgcgaagtg tatggcgatg atgtggaaga actggatatt 1620
ctggtgggcc tgatggcgga aaaaaaaatt aaaggctttg cgattagcga aaccgcgttt 1680
gtgatttttc tgattatggc gagccgccgc ctggaagcgg atcgcttttt taccagccat 1740
tttaacgaag aaacctatac caaaaaaggc ctggaatggg tgaacaccac cgaaagcctg 1800
aaagatgtga ttgaacgcca ttatccggaa attagcaaca aatggatgaa cagcagcagc 1860
gcgtttagcg tgtgggatag cccgccgaac aaaccgaacc cgattccgat ttattttcgc 1920
ctgccgcatt aa 1932

<210> SEQ ID NO 23
<211> LENGTH: 1938
<212> TYPE: DNA
<213> ORGANISM: Cucumis sativus

<400> SEQUENCE: 23
atgctgagcg tgctgctgaa accgattaaa gcgattctgc tgctgctggt gcgcctgttt 60
gtgcatcgcg attttcatga actggcgcgc cgcatgaccg tgctggatat ttatcgcttt 120
ctgattattc atagcattga taaaatgggc atttggccga aactgccggt gctgctgggc 180
ctgctgtatc tggcggcgcg ccgccatctg catcagcgct atagcctgta taaagtgggc 240
aaaaacaccc cggtgggcgt gcgcagccat ccggaagatt gcccgtatcg caccccggat 300
ggccgctata ccgatccgtt tgatgatgat gcgggcagcc agggcacctt ttttggccgc 360
aacgtgcatc cggtggatca gagcgaacgc ctgctgaaac cggatccgat ggtggtggcg 420
accaaactgc tggcgcgcaa aaaactgatt gataccggca aacagtttaa cgtgattgcg 480
gcgagctgga ttcagtttat ggtgcatgat tggatggatc atctggaaga taccaaacag 540
gtggaactgg tggcgccgag cgatgtggcg aaaagctgcc cgctgaaaag ctttaaattt 600
tttaaaacca aagaagaaag caccgatctg tttgatattc gcaccggcag cattaacatt 660
cgcaccccgt ggtgggatgg cagcgtgctg tatggcagca acgaacagat gctgaacaaa 720
gtgcgcacct atgaagatgg caaactgaaa attgcggatg atggcctgct gccgcatgat 780
aaagatggca ttgcgattag cggcgatgtg cgcaacagct gggcgggcgt gagcaccctg 840
caggcgctgt ttattaaaga acataacgcg gtgtgcgatg tgctgaaaaa agaatatggc 900
aacatggaag atgaagaact gtatcgccgc gcgcgcctgg tgaccagcgc ggtgattgcg 960
aaagtgcata ccattgattg gaccgtggaa ctgctgaaaa ccgataccct gctggcgggc 1020
atgcgcggca actggtatgg cctgctgggc aaaaaattta aagatacctt tggccatgtg 1080
ggcggcagca ttctgggcgg cctggtgggc ctgaaaaaac cgaacaacca tggcgtgacc 1140
tatagcctga ccgaagaatt taccagcgtg tatcgcatgc atcagctgct gccggatagc 1200
ttttatctgc gcgatgtgac cgtggatccg gatcagcata acaaaagccc gccgctgatt 1260
gaatatgtgc cgatggcgaa catgattggc cataaaggcg aagaaaccag caaaaaaatg 1320
ggctttaccg cgctgctggt gagcatgggc catcaggcga gcggcgcgct ggaactgttt 1380
aactatccgc tgtggctgcg cgatctgatt gcgcatgata tggataacaa agatcgcccg 1440
gatcatattg atctggcggc gctggaagtg tatcgcgatc gcgaacgccg cgtggcgcgc 1500
tataacgatt ttcgccgcgg cctgtttctg attccgatta gcaaatggga agatctgacc 1560

```
gatgataaag ataccattaa agtgctgcgc gaagtgtatg atgatgatgt ggaacagctg   1620

gatattctgg tgggcctgat ggcggaaaaa aaaattaaag gctttgcgat tagcgaaacc   1680

gcgtttgtga tttttctgat tatggcgagc cgccgcctgg aagcggatag ctttttttacc  1740

tgctattata acgaagaaac ctataccaaa aaaggcctgg aatgggtgaa aaccaccgaa   1800

agcctgaaag atgtgattga acgccatcat ccggaaatta gcaaaaaatg gattaacagc   1860

agcagcgcgt ttagcgtgtg ggatagcccg ccgaacaaac cgaaccatgt gccgctgtat   1920

ctgcgcattc cgaactaa                                                 1938
```

<210> SEQ ID NO 24
<211> LENGTH: 1920
<212> TYPE: DNA
<213> ORGANISM: Solanum lycopersicum

<400> SEQUENCE: 24

```
atgagctttg tgatgctgaa aaacctgctg ctgagcagcc tgcgcaaatt tattcataaa     60

gattttcatg aaatttttga taaaatgacc ctgattgata aactgttttt tctgattgtg    120

cattttattg ataaacataa cttttggcat cgcctgccgg tgtttttttgg cctgctgtat   180

ctgggcgcgc gccgcagcct gcatcagcag tataacctga ttaacgtggg ccgcaccccg    240

accggcgtgc gcagcaaccc ggcggattat ccgtatcgca ccgcggatgg caaatttaac    300

gatccgttta acgaaggcac cggcagccag tttagctttt ttggccgcaa catgatgccg    360

ctgcatcaga acaacaaact gaaaaaaccg gatccgatgg tggtggcgac caaactgctg    420

gcgcgccgca aatttattga taccggcaaa cagtttaaca tgattgcggc gagctggatt    480

cagtttatgg tgcatgattg gattgatcat ctggaagata cccagcaggt ggaactgcgc    540

gcgccgaaag aagtggcgaa cgaatgcccg ctgaaaagct ttcgctttaa caaaagcaaa    600

gaaaccccga ccgattttta tgaaattaaa accggccatc tgaacagccg caccccgtgg    660

tgggatggca gcgtgattta tggcagcaac gaagatgtgc tgaaaaaagt gcgcaccttt    720

cgcgatggca aactgaaact gggcgaaaac ggcctgattc agcaggatga aaacggcaaa    780

attattagcg gcgatgtgcg caacacctgg gcgggcctgc tgaccctgca ggcgctgttt    840

gtgcaggaac ataacgcggt gtgcgatacc ctgaaaaaag aatatccgga actggaagat    900

gaagaactgt atcgccatgc gcgcctggtg accagcgcgg tgattgcgaa agtgcatacc    960

attgattgga ccgtgcagct gctgaaaacc gataccatgc tggcgggcat gcgcgcgaac   1020

tggtatggcc tgctgggcaa aaaatttaaa gatacctttg gccatgtggg cagcattctg   1080

agcggcgtgg tgggcatgaa aaaaccggaa aaccatggcg tgccgtatag cctgaccgaa   1140

gaatttacca gcgtgtatcg catgcatcag ctgctgccgg ataccctgca gctgcgcaac   1200

attgatgcga ccccgggccc gaacaaaagc ctgccgctga ccaacgaaat tccgatggaa   1260

gaagtggtgg gcagcaaagg caaagaaaac ctgagccgca ttggctttac caaacagatg   1320

gtgagcatgg gccatcaggc gagcggcgcg ctggaactgt ggaactatcc ggtgtggatg   1380

cgcgatctga ttgcgcagga tgtggatggc accgatcgcc cggatccgat tgatctggcg   1440

gcgctggaaa tttatcgcga tcgcgaacgc agcgtgccgc gctataacga ttttcgccgc   1500

ggcatgctgc agattccgat tagcaaatgg gaagatctga ccgatgatga agaagcgatt   1560

aaaaccctgg gcgaagtgta tgatgatgat attcaggaac tggatctgct ggtgggcctg   1620

atggcggaaa aaaaaattaa aggctttgcg attagcgaaa ccgcgtttaa catttttctg   1680

ctgatggcga ttcgccgcct ggaagcggat cgctttttta ccagcaacta taacgatgaa   1740
```

acctatacca aaaaaggcct ggaatgggtg aacaccaccg aaagcctgaa agatgtgctg 1800
gatcgccatt atccggaaat gaccgataaa tggatgaaca gcaacagcgc gtttagcgtg 1860
tgggatagca gcccgcagcc gcataacccg attccgctgt attttcgcgt gccgcagtaa 1920

<210> SEQ ID NO 25
<211> LENGTH: 1899
<212> TYPE: DNA
<213> ORGANISM: Solanum lycopersicum

<400> SEQUENCE: 25
atggcgttta gcattagcct gccggatttt gtgcatccgc agctgcgcca tgtggtggcg 60
aaaatgagct tttttgatac cattctgttt tatgtggtgc atctggtgga taaatttgat 120
ctgtggcatc gcctgccggt gctgctgggc gcggcgtatc tgggcattcg ccgccatctg 180
catcagcgct ataacctgct gcatgtgggc aaagtgaacg gcaaaaaata tgataccgaa 240
gaatttacct atcgcaccgc ggatggcagc tgcaaccatc cggtggatca tctggtgggc 300
agccagggca ccttttttgg ccgcaacatg ctgccgagca ccagcagcta tgcgctgctg 360
gaaccgcatc cggtgaccgt ggcgagcaaa ctgctggaac gccgcaaata taccgattgc 420
ggcggccagt ttaacatgat tgcgtgcgcg tggctgcagt ttatgattca tgattggaac 480
gatcatatgg aagataccga acaggtggaa ctgcgcgcgc cgcaggatgt ggcggcgggc 540
tgcccgctga aaagctttaa atttctgaaa accaaaaaac tgccgaccgg cagcccggat 600
ctgaaatttg gccatctgaa cagccgcacc ccgtggtggg atggcagcgt gatttatggc 660
aacaacgaag aaggcatgat tcgcgtgcgc cgctttaaag atggcaaact gcgcctgagc 720
ggcgatggcc tgctggaaca tgatgataaa ggcattccga ttagcggcga tgtgcgcaac 780
tattgggcgg gctatagcct gctgcaggcg ctgtttgtga aagaacataa cgcgatttgc 840
gatatgctga aagaacatta tccggaattt gatgatgaaa aagtgtatcg ccatgcgcgc 900
ctgattacca gcgcggtgat tgcgaaaatt cataccattg attggaccct ggaaattgtg 960
aaaaccgata ccctgatggc gggcatgcgc attaactggt atggcctgct gggcaaacgc 1020
gtgaaagatc tgctgggccc gaaatttggc ccggtgctga gcggcctggt gggcctgaaa 1080
aaaccgcgcg atcatggcac cccgtatagc ctgaccgaag aatttgtgag cgtgtatcgc 1140
atgcatagcc tgctgccgga taccattgtg ctgcgcgatc tgaaaagcac caccagcgaa 1200
gataaaagcc tgccgattca ggatgaaatt ccgatgcgcg aaatgattgg caaagaaggc 1260
gaaaaaaacc tgagcaaaat tggcatggaa cagatgctgg tgagcatggg ccatcagagc 1320
agcggcgcgg gcaccctgtg gaactttccg agctggatgc gcaacctggt gccgcatgat 1380
attgatggcg atgatcgccc ggatagcatt gatatggcgg cgctggatat ttatcgcgat 1440
cgcgaacgcg gcgtgccgcg ctataacgaa tttcgccgca acctgctgat ggtgccgatt 1500
agcaaatggg aagatctgac caacgatgaa gaagtgattg aagcgctgca ggaagtgtat 1560
ggcgatgata ttgaaaaact ggatctgcag attggcctgc atgcggaaaa aaaaattaaa 1620
ggctttgcga ttagcgaaac cgcgtttttt atttttctgc tgattgcgag ccgccgcctg 1680
gaagcggatc gctttttttac caccgatttt aacagccgca cctataccga aaaaggcttt 1740
gaatgggtga acaaaaccga aaccctgaaa gatgtgattg atcgctattt tccggaaatg 1800
accgaaaaat atatgcgctg caccagcgcg tttagcgtgt ggagcagcga tccggatccg 1860
aaacattatc tgccgctgta tctgcgcccg gcgacctaa 1899

<210> SEQ ID NO 26
<211> LENGTH: 1899
<212> TYPE: DNA
<213> ORGANISM: Nicotiana attenuata

<400> SEQUENCE: 26
atggttttct cgttctcgtt aacatcattc gtccaccctc aattacgtca cgttgtcggt 60
aagatgtcgt tattcgacac aatcttattc tacgttgttc acttactcga caagttcgac 120
ttatggcacc gtttaccagt tctcttaggg ttagcttact tgggtttgcg tcgtcactta 180
caccaacgtt accacttact ccacgtaggt aaggtaaatg gtaagaagta cgacacggaa 240
gagttcagtt accgtactgc cgacggtacg tgtaatcacc ccgtagacca cctcgttgga 300
tcacacggta cattcttcgg gcgtaatatg ccgccttcta cttctacgta cggtcttctt 360
gagccccacc ccgctacggt agccacgaag ttgcttgagc gtcgtaagtg tactgactgt 420
gggtctcaac tcaatatgat cgggtgtgct tgggtccaat tcatgatcca cgactggaat 480
gaccacatgg aagacactga gcaagttgag ttacgtgctc cagaggacgt agcagccggt 540
tgtcctttga agtccttcaa gttcttcaag acacgtaagg ttcctacgga ctcgccagac 600
ccaaagttcg gtcacttgaa ttctcgtacg ccctggtggg acggttctgt aatctacggg 660
aataataagg aaggtatgat ccgtgtccgt acgttcaagg acggtaagtt gcgtgtttcg 720
ggtgacggtc ttttggagca cgacaataat ggtatcccca tctcgggtga cgttcgtaat 780
aattgggcag gtttctcatt actccaagcc ttattcatga aggagcacaa tgcaatctgt 840
gacatgttga aggagcacta ccctgagttc gacgacgaga agctttaccg tcacgcccgt 900
cttacaacga gtgccgttat cgccaagatc cacactttgg acttgtctat cgagttagcc 960
aagacggaca cggttgttgc cggtacgcgt atcaattggt acgggttctt gggaaagaag 1020
atcaaggatc tcctcggtct caagttcggt cccatcctta gtggtcttgt tggtttaaag 1080
cgtccacgtg accacggtac gccttacagt ctcacggaag agttcgtctc ggtataccgt 1140
atgcacagtt tactcccaga caagatcatc ttgcgtgact tgaagtccac gacatccgag 1200
gacaagtcac ttcctatcca agaggagatc cctatgacag agatgatcgg taaagaggga 1260
gagaagtccc tctcgaagat cggtatcgag caaatgcttg tctctatggg gcaccaatca 1320
tgtggggccg ccacgttgtg gaattaccct acgtggatgc gtaatcttgt tccccacgac 1380
gtagacggag aggagcgtcc tgacttagtt gacatggccg cccttgagat ctaccgtgac 1440
cgtgagcgtg gtgtccctcg ttacaatgag ttccgtcgta atctcttgat gatccctatc 1500
tcgaagtggg aagaccttac tgacgacgag gaagtaatcg aggccttaca agaggtctac 1560
ggggacgacg tagagaagtt ggacttgcaa gtcggtctcc acgcagagaa gaagatcaag 1620
ggattcgcca tctctgagac agcattcaat atcttcttac ttatcgcatc tcgtcgtctc 1680
gaggcagacc gtttcttcac gactaatttc aatgcacgta cttacacaga gaagggtttc 1740
gagtgggtca ataagacaga gacattgaag gacgtaatcg accgtcactt ccctgagatg 1800
actgagaagt acatgcgttg tacgtcagct ttcgcagtat ggaattcgga cccaaatcct 1860
cgtcgttact tacctcttta tctccgtcca gccacgtaa 1899

<210> SEQ ID NO 27
<211> LENGTH: 1932
<212> TYPE: DNA
<213> ORGANISM: Nicotiana attenuata

<400> SEQUENCE: 27
atgagcctgg tgatggcgag cctgaaaaac ctgctgctga gcccgctgcg cggctttatt 60
cataaagatt ttcatgatat ttttgaacgc atgaccctgc tggataaact gttttttctg 120
attgtgcatt ttgtggataa actgaacctg tggcatcgcc tgccggtgtt tctgggcctg 180
ctgtatctgg gcgcgcgccg ccatctgcat caggaatata acctgattaa cgtgggcaaa 240
accccggtgg gcgtgcgcag caacccggcg gatcatccgt atcgcaccgc ggatggcaaa 300
tataacgatc cgtttaacga aggcgcgggc agcgaactga gctttttggg ccgcaacatg 360
ctgccggtgg atcagcataa ccagctgaaa aaaccggatc cgatggtggt ggcgaccaaa 420
ctgctggcgc gccgcaacgt ggtggatacc ggcaaacagt ttaacatgat tgcggcgagc 480
tggattcagt ttatgattca tgattggatt gatcatctgg aagataccaa acagattgaa 540
ctgcgcgcgc cggaagaagt ggcgagccag tgcccgctga aaagctttaa attttttaaa 600
accaaagaaa ttccgaccgg cttttatgaa attaaaaccg gccatctgaa ccgccgcacc 660
ccgtggtggg atggcagcgc gatttatggc agcaacgcgg aagtgctgaa aaaagtgcgc 720
acctttaaat atggcaaact gaaactgagc gcggatggcc tgctggaaat tgatgaaaac 780
ggcaaaatta ttagcggcga tgtgcgcaac acctgggcgg gcctgagcgc gctgcaggcg 840
ctgtttgtgc aggaacataa cagcgtgtgc gatgtgctga aaaaagaata tccggaactg 900
gaagatgaag atctgtatcg ccatgcgcgc ctggtgacca gcgcggtgat tgcgaaagtg 960
cataccattg attggaccgt ggaactgctg aaaaccgata ccctgctggc gggcatgcgc 1020
gcgaactggt atggcctgct gggcaaaaaa tttaaagata cctttggcca tgtgggcggc 1080
agcattctgg gcggctttgt gggcatgaaa aaaccggaaa actatggcgt gccgtatagc 1140
ctgaccgaag aatttaccag cgtgtatcgc atgcatcagc tgctgccgga taacctgcag 1200
ctgcgcaaca ttgatgcgac cccgggcccg aacaaaagcc tgccgctgac caacgaaatt 1260
ccgatggaag atctgattgg cagcaaaggc gaagaaaacc tggcgcgcat tggctttacc 1320
aaacagatgg tgagcatggg ccatcaggcg tgcggcgcgc tggaactgtg gaactatccg 1380
atgtggatgc gcgatctgat tccgcaggat gtggatggca ccgatcgccc ggatcatgtg 1440
gatctggcgg cgctggaaat ttatcgcgat cgcgaacgca gcgtggcgcg ctataacgaa 1500
tttcgccgcg gcatgctgca gattccgatt agcaaatggg aagatctgac cgatgatgaa 1560
gaagtgatta acaccctgcg cgaagtgtat ggcgatgatg tggaagaact ggatctgatg 1620
gtgggcatgg cggcggaaaa aaaaattaaa ggctttgcga ttagcgaaac cgcgtttttt 1680
atttttctga ttatggcgag ccgccgcctg gaagcggatc gctttttttac cagcaactat 1740 aacgaagaaa cctataccaa aaaaggcctg gaatgggtga acaccaccga aagcctgaaa 1800
gatgtgctgg atcgccatta tccggaaatg accgaaaaat ggatgaacag cagcagcgcg 1860
tttagcgtgt gggatagcag cccggaaccg cataacccga ttccgctgta ttttcgcgtg 1920
ccgccgcagt aa 1932

<210> SEQ ID NO 28
<211> LENGTH: 1932
<212> TYPE: DNA
<213> ORGANISM: Nicotiana tabacum

<400> SEQUENCE: 28
atgagcctgg tgatggatag cctgaaaaac ctgctgctga gcccgctgcg cggctttatt 60
cataaagatc tgcatgatat ttttgaacgc atgaccctgc tgagcaaact gctgtttctg 120
attgtgcatc tggtggataa actgaacctg tggcatcgcc tgccggtgct gctgggcctg 180
ctgtatctgg gcgcgcgccg ccatctgcat caggaatata acctgattaa cgtgggcaaa 240
accccgattg gcgtgcgcag caacccggcg gatcatccgt atcgcaccgc ggatggcaaa 300
tataacgatc cgtttaacga aggcgcgggc agcgaactga gctttttggg ccgcaacatg 360
ctgccggtgg atcagcataa ccagctgaaa aaaccggatc cgatggtggt ggcgaccaaa 420
ctgctggcgc gccgcaactt tgtggatacc ggcaaacagt ttaacatgat tgcggcgagc 480
tggattcagt ttatgattca tgattggatt gatcatctgg aagataccaa acagattgaa 540
ctgaaagcgg cggaagaagt ggcgagccag tgcccgctga aaagctttcg ctttttttaaa 600
accaaagaaa ttccgaccgg cttttatgaa attaaaaccg gccatctgaa cacccgcacc 660
ccgtggtggg atggcagcgc gatttatggc agcaacgcgg aagtgctgaa aaaagtgcgc 720
acctttaaag atggcaaact gaaactgagc gcggatggcc tgctggaaat tgataaaaac 780
ggcaaaatta ttagcggcga tgtgcgcaac acctgggcgg gcctgagcgc gctgcaggcg 840
ctgtttgtgc aggaacataa cagcgtgtgc gatgcgctga aaaaagaata tccggaactg 900
gaagaagaag atctgtatcg ccatgcgcgc ctggtgacca gcgcggtgat tgcgaaagtg 960
cataccattg attggaccgt ggaactgctg aaaaccgata ccctgctggc gggcatgcgc 1020
gcgaactggt atggcctgct gggcaaaaaa tttaaagata cctttggcca tgtgggcggc 1080
agcattctgg gcggctttgt gggcatgaaa aaaccggaaa actatggcgt gccgtatagc 1140
ctgaccgaag aatttaccag cgtgtatcgc atgcatcagc tgctgccgga taaactgcag 1200
ctgcgcaaca ttgatgcgac cccgggcccg aacaaaagcc tgccgctgac caacgaaatt 1260
ccgctggaag atctgattgg cggcaaaggc gaaaaaaacc tgagcaaaat tggctttacc 1320
aaacagatgg tgagcatggg ccatcaggcg tgcggcgcgc tggaactgtg gaactatccg 1380
gtgtggatgc gcgatctgat tccgcaggat gtggatggca ccgatcgccc ggatcatatt 1440
gatctggcgg cgctggaaat ttatcgcgat cgcgaacgca gcgtggcgcg ctataacgaa 1500
tttcgccgcg gcatgctgca gattccgatt agcaaatggg aagatctgac cgatgatgaa 1560
gaagtgatta acaccctggg cgaagtgtat ggcgatgatg tggaagaact ggatctgatg 1620
gtgggcatgg cggcggaaaa aaaaattaaa ggctttgcga ttagcgaaac cgcgtttttt 1680
atttttctgg tgatggcgag ccgccgcctg gaagcggatc gctttttttac cagcaactat 1740
aacgaagaaa cctataccaa aaaaggcctg gaatgggtga acaccaccga aagcctgaaa 1800
gatgtgctgg atcgccatta tccggaaatt accgaaaaat ggatgaacag cagcagcgcg 1860
tttagcgtgt gggatagcac cccgcagccg cataacccga ttccgctgta ttttcgcgtg 1920
ccgccgcagt aa 1932

<210> SEQ ID NO 29
<211> LENGTH: 1935
<212> TYPE: DNA
<213> ORGANISM: Physcomitrella patens

<400> SEQUENCE: 29

```
atgggacaag tgtttggagc tttgacttca tggatggtat tacccgactt gcgtccaaca     60
taccgtcaaa tgtcgttcgt tcacgagacg atgttcttgg tagtacactt ctccgaccgt    120
ttctggcgtt ggtacaatac gccagttgtt ttcggtttgt tgtacttaga gttgcgtcgt    180
acgatccaac aaaattacaa tctcatcgct gtcgggaatg caaaggaccg taatcttcaa    240
gttcccacgc cttcccgtat ggcagtcgtt aattacatcg accaacctgg gagttcgtcc    300
cacacaactt tcgacgagga agactacgca ggtttcttcg gtcgtaatat gggtcctcaa    360
aagtcggagt tagttaatcc acaccccagt gtagtcgcag ccaagttgct tagtcgtact    420
gagttgaagg actacggtaa gcaattcaat atgatcgccg cgtcctggat caatttcatg    480
atccacgact gggttgacca cttagaggag ctttctaagg aagtcgagat cacagctccc    540
ccatccgtca gtgcccaatg tcctttaaag aatttcatgt tctaccctac gaaggaagtc    600
ccagcaggta ataatgttac tggtcacatc aatacgcgta ctccctggtg ggacgcaagt    660
gttatctacg ggtcaacgaa ggaagccgag cgtaatgttc gtacattccg tgacggaaag    720
cttaaggtac gtcccgacgg gtggttaatg acggacgagg acaatttgcc cgtcacaggt    780
gacatccgta atctttgggt cggtgttgcc atgctccaat cgcttttcat cgccgagcac    840
aatatggtat gtgacacaat caagaaggca caccctgact tcaatgacga ggagctcttc    900
caacacgccc gtgtagtaac tgccgctgtc ctcgcaaaga tccacacgat cgactggacg    960
cctcaacttt tgaagaataa tgttttgctt gcagcaatgc gtgctaattg gtacggttta   1020
ttgggaaagc gtttcaagga cacgttcggt acgactccta tctcgttgtt gtctggattg   1080
gtaggtatga agaagcctgt tgaccacggt gtaccctact cattaaccga ggagttcacg   1140
gctgtatacc gtcttcaccc tctcttacca gagaagatcg acatcaagaa tatcacagcc   1200
acagcctcat catcgttgca cacgccgccc acggtcgacg agatcgccgt acctgagctt   1260
ctcggtaata agggaaatga caaggcctta aagttgggat tgaagacatt attaacttct   1320
ttaggacacc aaagtgccgg tgcattacaa ctcttcaatt accctcaatg gatgcgtgag   1380
gtaactagtc aaaatcgtga cggtacggac cgtcccgaca aggtagacat ggcttcgttg   1440
gagatctacc gtgaccgtga gcgttcggta gcccgttaca atcaattccg tcgtaatctc   1500
gttatgccca ctatcggtaa gtgggaagac cttactgagg acaagcaaac gttggctatc   1560
cttcgtgagt tatacggaaa taatgtagag agtcttgacc ttttagtcgg attgttggtc   1620
gagaagaagc cacctggatt cgccatcagt gagacggcct tcgttatctt cgttttgatg   1680
gcttcgcgtc gtttagaggc cgacccactt ttcacgtcac acttcaatga gaaggtttac   1740
actgaagagg ggttaaagtg ggtcaatacg acggaaggat taaaggacgt cttgcgtcgt   1800
caccaccccg agttggtcgg tgactggatg actgcctcgt cagccttcag tttgtggaat   1860
caaactcctg agaagccttc gtggatccct ctctaccttc gttggggtgc aaattcacct   1920
gccgctagta gttaa                                                    1935
```

<210> SEQ ID NO 30
<211> LENGTH: 1932
<212> TYPE: DNA
<213> ORGANISM: Pisum sativum

<400> SEQUENCE: 30
atgtggagca ttgtgaccga tccgattaaa gatctgatta gcaaagtggt gaaaaacagc 60
attcatccgg attttcatga tgcggtgagc aaaatgacca ttattgatgc gtttctgttt 120
tttattgtgc atagcattga taaactgggc atttggcatc gcctgccggt gtttttggc 180 ctgctgtatc tggcgattcg ccgccatctg catcaggaat ataacctgct gaacgtgggc 240
accaccccgg tgggcattcg cagcaacccg agcgattttc cgtatcgcac cgcggatggc 300
cgctataacg atccgtttaa cgatggcgcg ggcagccagg gcagcttttt tggccgcaac 360
attctgccgg tggatcagaa aaacaaactg ctgaaaccgg atccgatggt ggtggtgacc 420
aaactgctgg aacgcaaaac ctataaagat accggcaccc agtttaacgt gattgcggcg 480
agctggattc agtttatgat tcatgattgg attgatcata tggaagatac caaacaggtg 540
gaactgagcg cgccgagcga agtggcgagc cagtgccccgc tgaaaagctt taaatttttt 600
aaaaccaaag aaattccgac cggcttttat gatattaaaa ccggccatgc gaacgtgcgc 660
accccgtggt gggatggcag cgtggtgtat ggcagcaacg aacaggtgct gaacaaagtg 720
cgcaccttta aagatggcaa actgaaaatt agcaaagaag gccatctgct gcataacgaa 780
gatggcaccg cgattagcgg cgatattcgc aacagctggg cgggcgtgac caccctgcag 840
accctgtttg tgcaggaaca taacgcggtg tgcgatgcgc tgaaaaaaga aaacagcgat 900
ctggaagatg aagatctgta tcgccatgcg cgcctggtga ccagcgcggt gattgcgaaa 960
attcatacca ttgattggac cgtggaactg ctgaaaaccg ataccctgct ggcgggcatg 1020
cgcgcgaact ggtatggcct gctgggcaaa cagtttaaag atcgctttgg ccatgtgggc 1080
aacagcattc tgagcggctt tgtgggcatg aaacgcagcg aaaaccatgg cgtgccgtat 1140
agcctgaccg aagaatttgc gaccgtgtat cgcatgcatc cgctgctgcc ggatagcctg 1200
catctgcgcg atattagcgc gagcccgggc ccgaacaaaa gcccgccgct gattaaagaa 1260
attccgatga acgatctgat tggcctgcag ggcgaaaaaa ccctgctgga aattggcaac 1320
gcgaaaaaac tggtgagcat gggccatcag gcgtgcggcg cgctggaact gtggaactat 1380
ccgagctggc tgcgcaacct ggtgccgcat aacattgatg gcaccgaacg cagcgatcat 1440
gtggatctgg cggcgctgga agtgtatcgc gatcgcgaac gcaacgtggc gcgctataac 1500
cagtttcgcc gcggcctgct gctgattccg attagcaaat gggaagatct gaccgatgat 1560
gaagaagcga ttaaagtgct ggaagaagtg tatggcgatg atgtggaaga actggatgtg 1620
ctggtgggcc tgatggcgga aaaaaaaatt aaaggctttg cgattagcga aaccgcgttt 1680
gtgatttttc tgctgatggc gagccgccgc ctggaagcgg atcgcttttt taccagcaac 1740
tttaacgaag aaacctatac caaaaaaggc ctggaatggg tgaacaccac cgaaagcctg 1800
aaagatgtga ttgatcgcca tcatccggaa atgacccata aatggctgaa cagcagcagc 1860
gcgtttagcg tgtgggatac cagcccgaac aaacataacc atattccgat ttattttcgc 1920
gtgccgaact aa 1932

<210> SEQ ID NO 31
<211> LENGTH: 1899
<212> TYPE: DNA
<213> ORGANISM: Solanum lycopersicum

<400> SEQUENCE: 31
atggcgttta gcattagcct gccggatttt gtgcatccgc agctgcgcca tgtggtggcg 60
aaaatgagct tttttgatac cattctgttt tatgtggtgc atctggtgga taaatttgat 120
ctgtggcatc gcctgccggt gctgctgggc gcggcgtatc tgggcattcg ccgccatctg 180
catcagcgct ataacctgct gcatgtgggc aaagtgaacg gcaaaaaata tgataccgaa 240
gaatttacct atcgcaccgc ggatggcagc tgcaaccatc cggtggatca tctggtgggc 300
agccagggca cctttttgg ccgcaacatg ctgccgagca ccagcagcta tgcgctgctg 360
gaaccgcatc cggtgaccgt ggcgagcaaa ctgctggaac gccgcaaata taccgattgc 420
ggcggccagt ttaacatgat tgcgtgcgcg tggctgcagt ttatgattca tgattggaac 480
gatcatatgg aagataccga acaggtggaa ctgcgcgcgc cgcaggatgt ggcggcgggc 540
tgcccgctga aaagctttaa atttctgaaa accaaaaaac tgccgaccgg cagcccggat 600
ctgaaatttg gccatctgaa cagccgcacc ccgtggtggg atggcagcgt gatttatggc 660
aacaacgaag aaggcatgat tcgcgtgcgc cgctttaaag atggcaaact gcgcctgagc 720
ggcgatggcc tgctggaaca tgatgataaa ggcattccga ttagcggcga tgtgcgcaac 780
tattgggcgg gctatagcct gctgcaggcg ctgtttgtga aagaacataa cgcgatttgc 840
gatatgctga aagaacatta tccggaattt gatgatgaaa aagtgtatcg ccatgcgcgc 900
ctgattacca gcgcggtgat tgcgaaaatt cataccattg attggaccct ggaaattgtg 960
aaaaccgata ccctgatggc gggcatgcgc attaactggt atggcctgct gggcaaacgc 1020
gtgaaagatc tgctgggccc gaaatttggc ccggtgctga gcggcctggt gggcctgaaa 1080
aaaccgcgcg atcatggcac cccgtatagc ctgaccgaag aatttgtgag cgtgtatcgc 1140
atgcatagcc tgctgccgga taccattgtg ctgcgcgatc tgaaaagcac caccagcgaa 1200
gataaaagcc tgccgattca ggatgaaatt ccgatgcgcg aaatgattgg caaagaaggc 1260
gaaaaaaacc tgagcaaaat tggcatggaa cagatgctgg tgagcatggg ccatcagagc 1320
agcggcgcgg gcaccctgtg gaactttccg agctggatgc gcaacctggt gccgcatgat 1380
attgatggcg atgatcgccc ggatagcatt gatatggcgg cgctggatat ttatcgcgat 1440
cgcgaacgcg gcgtgccgcg ctataacgaa tttcgccgca acctgctgat ggtgccgatt 1500
agcaaatggg aagatctgac caacgatgaa gaagtgattg aagcgctgca ggaagtgtat 1560
ggcgatgata ttgaaaaact ggatctgcag attggcctgc atgcggaaaa aaaaattaaa 1620
ggctttgcga ttagcgaaac cgcgtttttt atttttctgc tgattgcgag ccgccgcctg 1680
gaagcggatc gctttttac caccgatttt aacagccgca cctataccga aaaaggcttt 1740
gaatgggtga acaaaaccga aaccctgaaa gatgtgattg atcgctattt tccggaaatg 1800
accgaaaaat atatgcgctg caccagcgcg tttagcgtgt ggagcagcga tccggatccg 1860
aaacattatc tgccgctgta tctgcgcccg gcgacctaa 1899

<210> SEQ ID NO 32
<211> LENGTH: 1920
<212> TYPE: DNA
<213> ORGANISM: Solanum tuberosum

<400> SEQUENCE: 32
atgtcgttcg ttatgttgaa gaatctttta ctctctcctt tgcgtaagtt catccacaag 60
gacttccacg agatcttcga gaagatgacg ttaatcgaca agttgttctt cttaatcgtc 120

```
cacttcatcg acaagtacaa tttctggcac cgtttgcctg ttttcttcgg gttgctttac    180
ttaggtgctc gtcgtacact tcaccaacaa tacaatctca tcaatgttgg tcgtactcca    240
acgggcgttc gttcgaatcc tgctgactac ccttaccgta cggcagacgg taagttcaat    300
gacccttca atgagggtgc agggtcgcaa ttctctttct tcggtcgtaa tatgatgcca     360
gtccaccaag acaataagtt aaagaagcca gaccccatgg tagtagcaac gaagctcctc    420
gcccgtaaga agttcatcga cactggtaag caattcaata tgatcgccgc atcttggatc    480
caattcatgg tccacgactg gatcgaccac ctcgaggaca ctcaacaagt tgagctccgt    540
gcacccaagg aagtcgccaa tgagtgtcct ttgaagtcgt tccgtttcaa taagtctaaa    600
gagacaccta cagacttcta cgagatcaag aagggtcact taaatatccg tacgccatgg    660
tgggacggta gtgtcatcta cggttcgaat gaggacgttc tcaagaaggt tcgtacattc    720
aaggacggga agctcaagtt atcggagaat ggtttgatcc aacaagacga gaatggaaag    780
atcatctctg gagacgttcg taatacgtgg gcaggtttat tgactttgca agccttattc    840
gttcaagagc acaatgctgt ctgtgacact ctcaagaagg agtacccaga gctcaaggac    900
gaggagcttt accgtcacgc ccgtttagta acgtccgcag ttatcgccaa ggtacacact    960
atcgactgga cagtccaatt gttgaagacg gacactttac ttgccggtat gcgtgctaat   1020
tggtacggtc tcttaggtaa gaagttcaag gacacgttcg gacacgtagg gtcgatctta   1080
tcaggagttg ttggaatgaa gaagccagag aatcacggtg ttccatacag tctcacagag   1140
gagttcgttt gtgtataccg tatgcaccaa ttgttaccag acactttaca attgcgtaat   1200
atcgacgcaa ctcccggtcc aaataagagt ctccccttga cgaatgagat ccccatggaa   1260
gaggtcgtag ggtctaaggg taaagagaat ctttcacgta tcggtttcac aaagcaaatg   1320
gtctcaatgg gacaccaagc cagtggtgca ttagagttgt ggaattaccc tgtatggatg   1380
cgtgacttga tcgcccaaga cgtagacggt actgaccgtc ctcaccacat cgacctcgcc   1440
gcattggaga tctaccgtga ccgtgagcgt tctgtcgccc gttacaatga cttccgtcgt   1500
ggtatgcttc aaatccctat ctctaagtgg gaagacttaa cggacgacga ggaagccatc   1560
aagacgctcc gtgaggttta cgacgacgac atcgaggagt tagacttact cgtcggtctt   1620
atggctgaga agaagatcaa gggtttcgct atcagtgaga cagccttcaa tatcttctta   1680
cttatggcca tccgtcgttt ggaagccgac cgtttcttca cgtcaaatta caatgaggag   1740
acgtacacta agaagggttt agagtgggtt aatacgactg agggacttaa ggacgtctta   1800
gaccgtcact accctgagat gactgagaag tggatgaatt ctaatagtgc cttctctgtt   1860
tgggactcgt cacccgagcc ccacaatcca atccctctct acttccgtgt cccccaataa   1920
```

<210> SEQ ID NO 33
<211> LENGTH: 1917
<212> TYPE: DNA
<213> ORGANISM: Solanum tuberosum

<400> SEQUENCE: 33

```
atgagctttc tggaaaacct gctgctgagc catctgctga actttattca tcgcgatttt     60
catgaagtgt ttgaagaaat gaccctgatt aacaaatttc tgtttctgat ggtgcatttt    120
gtggataaac tgaacttttg gcatcgcctg ccggtgtttc tgggcctggc gtatctgggc    180
gcgcgccgcc gcctgcatca gcagtataac ctgattaacg tgggcaccac ccataccggc    240
aacagcggcg attatccgta tcgcaccgcg gatggcaaat ataacgatcc gtttaacgaa    300
aacgcgggca gcgaatttag ctttttggc cgcaacatga tgccggtgca tcagctgaac     360
```

```
aaactgaaaa aaccggatcc gatggtggtg gcgaccaaac tgctggcgcg ccgcaaattt    420
attgataccg gcaaacagct gaacattatt gcggcgagct ggattcagtt tatgattcat    480
gattggattg atcatatgga agataccaac cagatgaaac tggatgcgcc gaaagatgtg    540
gcgagccagt gcccgctgaa aagctttaaa ttttataaaa gcaccgaaac cccgaccggc    600
ctggatgaaa ttaaaaccgg ccatctgaac cgccgcaccc cgtggtggga tggcagcgcg    660
atttatggca acaacgcgga tgatctgaaa aaagtgcgca cctttattga tggcaaactg    720
aaactgagcg aaaacggcct gattcagcag gatgaaaacg gcaaaattat tagcggcgat    780
gtgcgcaaca cctgggcggg cctgctgacc ctgtatgcgc tgtttgtgca ggaacataac    840
gcggtgtgcg atgcgctgaa aaaagaatat ccggaactga aagatgaaga tctgtatcgc    900
catgcgcgcc tggtgaccag cgcggtgatt gcgaaagtgc ataccattga ttggaccgtg    960
gaactgctga aaaccgatac cctgctggcg ggcatgcgca ttagctggta tggcctgctg   1020
ggcaaaaaat ttaaagatac ctttggccat attggcggcg atttttggct gagcggcttt   1080
gtgggcatga aaaaaccgcg caaccatggc gtgccgtata gcctgaccga agaatttagc   1140
agcgtgtatc gcctgcatca gctggtgccg gataccctgc agctgcgcaa cattgatgcg   1200
accccggcgc cgaacaaaag cctgccgctg attaacgaaa ttccgatgga agatctgatt   1260
ggcggcaaag gcgcggaaaa actgagcaaa attggctttc tgaaccagat ggtgagcatg   1320
ggccatcaga gctgcggcgc gctggaactg tggaactatc cggtgtggat gcgcgatctg   1380
gtggcgcagg atgtggatgg caccgatcgc ccggatcatg tggatctgcc ggcgctggaa   1440
atttatcgcg atcgcgaacg cagcgtggcg cgctataacg aatttcgccg ccgcattttt   1500
cagattccga ttaccaaatg ggaagatctg agcgatgata aagaagtgat tgaaaccctg   1560
gtggaagtgt atggcgataa caacgtggaa gaactggatc tgctggtggg cattatggcg   1620
gaaaaaaaaa ttaaaggctt tgtgattagc gaaaccgcgt tttttatttt tctgtttatg   1680
gcgggccgcc gcctggaagg cgatcgcttt tttaccagca actataacga agaaacctat   1740
accaaacgcg gcctggaatg ggtgaacacc accgaaagcc tgaaagatgt gctggatcgc   1800
cattatccga aaatgaccga aaaatggatg aacagcagca gcgcgtttag cgtgtgggat   1860
agcagcccgc agccgtataa cccgattccg ctgtatctgc gcctgccgca taaataa      1917
```

<210> SEQ ID NO 34
<211> LENGTH: 1902
<212> TYPE: DNA
<213> ORGANISM: Solanum tuberosum

<400> SEQUENCE: 34

```
atgagctttg tgaacctgct gctgtttccg ctgcgctgct ttattcataa agattttcat     60
gatgtggtgg atcgcatgag cctgctgaac aaactgctgt ttatgatggt gcatctggtg    120
gataaactga acctgtggca tcgcctgccg gtgtttctgg gcctgctgta tctggcggcg    180
cgccgccatc tgcatcagga atataacctg attaacgtgg gcgtgggccg caaaccgatt    240
gatgtgacca gcaaccgcgc ggtgggcaaa tataacgatc cgtttaacga aggcggcggc    300
agcgaatttc cgttttttgg ccgcaacatg atgccggtgg atcagcatga aaaactgaaa    360
aacccggatc cgatggtggt ggcgaccaaa ctgctggcgc gccgcaaatt tattgatacc    420
ggcaaacagt ttaacatgat tgcggcgagc tggattcagt ttatgattca tgattggatt    480
gatcatctgg aagataccca gcagattgaa ctgcgcgcgc cggaagaagt ggcgagcgaa    540
```

tgcccgctga aaagctttaa attttttaaa accaaacaga ccccgaccgg cctgtgcgat 600
attcagaccg gccatctgaa cattcgcacc ccgcagtggg atggcagcgc gatttatggc 660
aacaacgcgg aagtgagcaa aaaagtgcgc acctttaaag atggcaaact gaaactgagc 720
gaaaacggcc tgctggaaca ggatgaaaac ggcaaaatta ttagcggcga tgtgcgcaac 780
aactgggcgg gcctgctgag cctgcaggcg ctgtttgtgc aggaacataa cctggtgtgc 840
gataccctga aaaaagaata tccggaactg aaagatgaag atctgtatcg ccatgcgaaa 900
ctggtgacca gcgcggtgat tgcgaaaatt cataccattg attggaccgt ggaactgctg 960
aacaccgata ccctgctggc gggcatgcgc gcgaactggt atggcctgct gggcaaaaaa 1020
tttaaagata cctttggcca tgtgggcggc agcattctgg gcggctttgt gggcatgaaa 1080
aaaccggaag atcatggcgt gccgtatagc ctgaccgaag aatttaccag cgtgtatcgc 1140
atgcatcagc tgctgccgga taccctgcag ctgcgcaaca ttgatgcgac cccgggcctg 1200
aacaaaagcc tgccgctgac caacgaaatt ctgatggaag atctgattgg cggcaaaggc 1260
aaagaaaacc tgagccgcat tggctttacc aaacagatgg tgagcatggg ccatcaggcg 1320
agcggcgcgc tggaactgtg gaactatccg atttggatgc gcgatctgat tgcgcaggat 1380
gtggatggca ccgatcgccc gcatcatatt gatctggcgg cgctggaaat ttatcgcgat 1440
cgcgaacgca gcgtggcgcg ctataacgaa tttcgccgcc gcatgctgca gattccgatt 1500
agcaaatggg aagatctgac cgatgatgaa gaagtgatta aaaccctgca tgaagtgtat 1560
ggcgatgaag tggaacagct ggatctgctg gtgggcatga gcgcggaaaa aaaaattaaa 1620
ggctttgcga ttagcgaaac cgcgtttatt atttttctga ttatggcgag ccgccgcctg 1680
gaagcggata aatttttac cagctattat aacgatgaaa cctataccaa aaaaggcctg 1740
gaatgggtga acaccaccga aagcctgaaa gatgtgctgg atcgccatta tccggaaatg 1800
accgaaaaat ggatgaacag caacagcgcg tttagcgtgt gggatagcag cccggaaccg 1860
cataacccga ttccgctgta ttttcgcgtg ccgcgcacct aa 1902

<210> SEQ ID NO 35
<211> LENGTH: 1929
<212> TYPE: DNA
<213> ORGANISM: Solanum tuberosum

<400> SEQUENCE: 35
atgaccatga ttatgctgaa aaacctgctg tttagcccgc tgcgcggctt tattcataaa 60
gattttcatc agattctgga taaaatgaac ctgcgcgata aactgagctt tctgattgtg 120
catattgtgg ataaacataa cctgtggcat cgcgtgccgg tgtttctggg cctggtgtat 180
ctggcgctgc gccgccatct gaaccaggaa tataacctga ttaacgtggg ccgcaccccg 240
accggcgtgc gcagcaaccc gggcgatttt ccgtatcgca ccgcggatgg caaatataac 300
gatccgttta acgaaggcgc gggcagcgaa tttagctttt ttggccgcaa catgatgccg 360
gtggatcagc atgataaact gaaaaacccg gatccgatgg tggtggcgac caaactgctg 420
gcgcgccgca aatttattga taccggcaaa cagtttaaca tgattgcggc gagctggatt 480
cagtttatga ttcatgattg gattgatcat ctggaagata cccagcagat tgaagaactg 540
cgcgcgccgg aagaagtggc gagccagtgc ccgctgaaaa gctttaaatt ttataaaagc 600
aaagaaaccc cgaccggctt ttatgaaatt aaaaccggct atctgaaccg ccgcaccccg 660
tggtgggatg gcagcgcgat ttatggcagc gatgtggaaa ttctgaaaaa agtgcgcacc 720
tttaaagatg gcaaactgaa actgagcgaa aacggcctgc tggaacagga tgaaaacggc 780

```
aaaattatta gcggcgatgt gcgcaacacc tgggcgggcc tgctgagcct gcaggcgctg    840
tttgtgcagg aacataacct ggtgtgcgat gcgctgaaaa aagaatatcc ggaactggaa    900
gatgaagtgc tgtatcgcca tgcgcgcctg gtgaccagcg cggtgattgc gaaagtgcat    960
accattgatt ggaccgtgga actgctgaaa accgataccc tgctggcggc gatgcgcgcg   1020
aactggtatg gcctgctggg caaaaaattt aaagatacct ttggccatgt gggcggcgcg   1080
attctgggcg gcctggtggg catgaaaaaa ccggaaaacc atggcgtgcc gtatagcctg   1140
accgaagaat ttgtgagcgt gtatcgcatg catcagctgc tgccggataa actgcagctg   1200
cgcaacattg ataccaccag cggcccgaac aaaagcctgc cgctgaccaa cgaaattccg   1260
atggaagatc tgattggcgg caaaggcgcg aaaaacctga gcaaaattgg ctttattacc   1320
cagatggtga gcatgggcca tcaggcgtgc ggcgcgctgg aactgtggaa ctatccggtg   1380
tggatgcgcg atctggtggc gcaggatgtg gatggcaccg atcgcccgga tcatgtggat   1440
ctgccggcgc tggaaattta tcgcgatcgc gaacgcagcg tggcgcgcta taacgaattt   1500
cgccgccgca tgctgcagat tccgattacc aaatgggaag atctgaccga tgatgaagaa   1560
gtgattaaaa ccctggatga agtgtatggc gatgatgtgg aacagctgga tctgctggtg   1620
ggcatgagcg cggaaaaaaa aattaaaggc tttgcgatta gcgaaaccgc gtttttttatt   1680
tttctgctga tggcgagccg ccgcctggaa gcggatcgct tttttaccag caactataac   1740
gaagaaacct ataccaaaaa aggcctggaa tgggtgaaca ccaccgaaag cctgaaagat   1800
gtgctggatc gccattatcc ggaaatgacc gataaatgga tgaacagcaa cagcgcgttt   1860
agcgtgtggg atagcagccc gcagccgcat aacccgctgc cgctgtattt tcgcgtgccg   1920
aaacattaa                                                           1929
```

<210> SEQ ID NO 36
<211> LENGTH: 1899
<212> TYPE: DNA
<213> ORGANISM: Solanum tuberosum

<400> SEQUENCE: 36

```
atggcgttta gcattagcct gccggatttt gtgcatccgc agctgcgcca tgtggtggcg     60
aaaatgagcc tgtttgatac cattctgttt tatgtggtgc atctggtgga taaatttgat    120
ctgtggcatc gcctgccggt gctgctgggc gcggcgtatc tgggcattcg ccgccatctg    180
catcagcgct ataacctgct gcatgtgggc aaagtgaacg gcaaaaaaata tgataccaaa    240
gaatttacct atcgcaccgc ggatggcacc tgcaaccatc cggtggatca tctggtgggc    300
agccagggca cctttttgg ccgcaacatg ctgccgagca ccagcagcta tgcgctgctg    360
gaaccgcatc cggtgaccgt ggcgaccaaa ctgctggaac gccgcaaata taccgattgc    420
ggcggccagt ttaacatgat tgcgtgcgcg tgggtgcagt ttatgattca tgattggaac    480
gatcatatgg aagataccga acaggtggaa ctgcgcgcgc cgcaggatgt ggcggcgggc    540
tgcccgctga aagctttaa atttctgaaa accaaaaaac tgccgaccgg cagcccggat    600
ctgaaatttg gccatctgaa cagccgcacc ccgtggtggg atggcagcgt gatttatggc    660
aacaacgaag aaggcatgat tcgcgtgcgc cgctttaaag aaggcaaact gcgcgtgagc    720
ggcgatggcc tgctggaaca tgatgataaa ggcattccga ttagcggcga tgtgcgcaac    780
tattgggcgg gctatagcct gctgcaggcg ctgtttgtga aagaacataa cgcgatttgc    840
gatatgctga aagaacatta tccggaattt gatgatgaaa aagtgtatcg ccatgcgcgc    900
```

-continued

```
ctgattacca gcgcggtgat tgcgaaaatt cataccattg attggaccct ggaactggtg    960

aaaaccgata ccctgatggc gggcatgcgc attaactggt atggcctgct gggcaaaaaa   1020

gtgaaagatc tgctgggccc gaaatttggc ccggtgctga gcggcctggt gggcctgaaa   1080

aaaccgcgcg atcatggcac cccgtatagc ctgaccgaag aatttgtgag cgtgtatcgc   1140

atgcatagcc tgctgccgga taccattgtg ctgcgcgatc tgaaaagcac caccagcgaa   1200

gataaaagcc tgccgattca ggatgaaatt ccgatgcgcg aaatgattgg caaagaaggc   1260

gaaaaaaacc tgagcaaaat tggcatggaa cagatgctgg tgagcatggg ccatcagagc   1320

tgcggcgcgg cgaccctgtg gaactttccg agctggatgc gcaacctggt gccgcatgat   1380

attgatggcg atgatcgcct ggatctgatt gatatggcgg cgctggatat ttatcgcgat   1440

cgcgaacgcg gcattccgcg ctataacgaa tttcgccgca acctgctgat ggtgccgatt   1500

agcaaatggg aagatctgac cgatgatgaa gaagtgattg aagcgctgca ggaagtgtat   1560

ggcgatgata ttgaaaaact ggatctgcag gtgggcctgc atgcggaaaa aaaaattaaa   1620

ggctttgcga ttagcgaaac cgcgtttttt atttttctgc tgattgcgag ccgccgcctg   1680

gaagcggatc gctttttac caccgatttt aacagccgca cctataccga aaaaggcttt    1740

gaatgggtga acaaaaccga aaccctgaaa gatgtgattg atcgcagctt tccggaaacc   1800

accgaaaaat atatgcgctg caccagcgcg tttagcgtgt ggagcagcga tccggatccg   1860

aaacattatc tgccgctgta tctgcgcccg gcgacctaa                          1899
```

```
<210> SEQ ID NO 37
<211> LENGTH: 631
<212> TYPE: PRT
<213> ORGANISM: Arabidopsis thaliana

<400> SEQUENCE: 37

Met Gly Phe Ser Pro Ser Ser Ser Trp Phe Leu His Pro Gln Leu His
1               5                   10                  15

His Val Val Ser Lys Met Ser Tyr Phe Asp Ala Phe Leu Phe Tyr Ile
            20                  25                  30

Val His Leu Val Asp Lys Leu Gly Leu Trp His Arg Phe Pro Val Leu
        35                  40                  45

Leu Gly Val Ala Tyr Leu Gly Leu Arg Arg His Leu His Gln Arg Tyr
    50                  55                  60

Asn Leu Val His Val Gly Pro Ile Asn Gly Gln Gly Tyr Asp Thr Asp
65                  70                  75                  80

Glu Phe Cys Tyr Arg Thr Ala Asp Gly Lys Cys Asn His Pro Ser Asp
                85                  90                  95

Asn Thr Ile Gly Ser Gln Gly Ser Phe Ile Gly Arg Asn Met Pro Pro
            100                 105                 110

Ser Thr Ser Gln Tyr Gly Ile Leu Asp Pro His Pro Ser Val Val Ala
        115                 120                 125

Thr Lys Leu Leu Ala Arg Lys Arg Phe Ile Asp Asn Gly Asp Gln Phe
    130                 135                 140

Asn Val Ile Ala Cys Ser Trp Ile Gln Phe Met Ile His Asp Trp Val
145                 150                 155                 160

Asp His Leu Glu Asp Thr His Gln Ile Glu Leu Glu Ala Pro Glu Glu
                165                 170                 175

Val Ala Ser Gly Cys Pro Leu Lys Ser Phe Lys Phe Leu Arg Thr Lys
            180                 185                 190
```

```
Lys Val Pro Thr Asp Asp His His Lys Ser Gly Ala Val Asn Thr Arg
        195                 200                 205

Thr Pro Trp Trp Asp Gly Ser Val Ile Tyr Gly Asn Asp Glu Thr Gly
    210                 215                 220

Met Arg Arg Val Arg Val Phe Lys Asp Gly Lys Leu Lys Ile Ser Gly
225                 230                 235                 240

Asp Gly Leu Leu Glu Arg Asp Glu Arg Gly Val Pro Ile Ser Gly Asp
                245                 250                 255

Ile Arg Asn Ser Trp Ser Gly Phe Ser Leu Leu Gln Ala Leu Phe Val
            260                 265                 270

Lys Glu His Asn Ser Val Cys Asp Met Leu Lys Glu Arg Tyr Pro Asp
        275                 280                 285

Phe Asp Asp Glu Lys Leu Tyr Arg Thr Ala Arg Leu Val Thr Ala Ala
    290                 295                 300

Val Ile Ala Lys Val His Thr Ile Asp Trp Thr Ile Glu Leu Leu Lys
305                 310                 315                 320

Thr Asp Thr Leu Thr Ala Gly Met Arg Ile Asn Trp Tyr Gly Phe Phe
                325                 330                 335

Gly Lys Lys Val Lys Asp Met Val Gly Ala Arg Phe Gly Pro Leu Phe
            340                 345                 350

Ser Gly Leu Val Gly Leu Lys Lys Pro Asn Asp His Gly Val Pro Tyr
        355                 360                 365

Ser Leu Thr Glu Glu Phe Val Ser Val Tyr Arg Met His Cys Leu Leu
    370                 375                 380

Pro Glu Thr Leu Ile Leu Arg Asp Met Asn Ser Glu Asn Val Asp Lys
385                 390                 395                 400

Glu Asn Pro Ala Ile Glu Arg Glu Ile Pro Met Thr Glu Leu Ile Gly
                405                 410                 415

Lys Lys Ala Gly Glu Lys Ala Ser Lys Leu Gly Phe Glu Gln Leu Leu
            420                 425                 430

Val Ser Met Gly His Gln Ser Cys Gly Ala Leu Thr Leu Trp Asn Tyr
        435                 440                 445

Pro Asn Trp Met Arg Asn Leu Val Ala Gln Asp Ile Asp Gly Glu Asp
    450                 455                 460

Arg Pro His Leu Ile Asp Met Ala Ala Leu Glu Ile Tyr Arg Asp Arg
465                 470                 475                 480

Glu Arg Gly Val Pro Arg Tyr Asn Glu Phe Arg Lys Asn Leu Leu Met
                485                 490                 495

Ser Pro Ile Ser Lys Trp Glu Glu Leu Thr Asp Asp Glu Glu Ala Ile
            500                 505                 510

Lys Val Leu Arg Glu Val Tyr Glu Asp Asp Ile Glu Lys Leu Asp Leu
        515                 520                 525

Asn Val Gly Leu His Ala Glu Lys Lys Ile Lys Gly Phe Ala Ile Ser
    530                 535                 540

Glu Thr Ala Phe Phe Ile Phe Leu Leu Val Ala Ser Arg Arg Leu Glu
545                 550                 555                 560

Ala Asp Arg Phe Phe Thr Thr Asn Phe Asn Glu Lys Thr Tyr Thr Lys
                565                 570                 575

Glu Gly Leu Glu Trp Val Asn Thr Thr Glu Thr Leu Lys Asp Val Ile
            580                 585                 590

Asp Arg His Phe Pro Arg Leu Thr Asp Gln Trp Met Arg Cys Ser Ser
        595                 600                 605
```

```
Ala Phe Ser Val Trp Gly Ser Asp Pro Asn Pro Lys Asn Trp Val Pro
    610                 615                 620

Leu Tyr Leu Arg Ser Ala Pro
625                 630


<210> SEQ ID NO 38
<211> LENGTH: 639
<212> TYPE: PRT
<213> ORGANISM: Arabidopsis thaliana

<400> SEQUENCE: 38

Met Lys Val Ile Thr Ser Leu Ile Ser Ser Ile Leu Leu Lys Phe Ile
1               5                   10                  15

His Lys Asp Phe His Glu Ile Tyr Ala Arg Met Ser Leu Leu Asp Arg
            20                  25                  30

Phe Leu Leu Leu Ile Val His Gly Val Asp Lys Met Val Pro Trp His
        35                  40                  45

Lys Leu Pro Val Phe Leu Gly Leu Thr Tyr Leu Glu Val Arg Arg His
    50                  55                  60

Leu His Gln Gln Tyr Asn Leu Leu Asn Val Gly Gln Thr Pro Thr Gly
65                  70                  75                  80

Ile Arg Phe Asp Pro Ala Asn Tyr Pro Tyr Arg Thr Ala Asp Gly Lys
                85                  90                  95

Phe Asn Asp Pro Phe Asn Glu Gly Val Gly Ser Gln Asn Ser Phe Phe
            100                 105                 110

Gly Arg Asn Cys Pro Pro Val Asp Gln Lys Ser Lys Leu Arg Arg Pro
        115                 120                 125

Asp Pro Met Val Val Ala Thr Lys Leu Leu Gly Arg Lys Lys Phe Ile
    130                 135                 140

Asp Thr Gly Lys Gln Phe Asn Met Ile Ala Ala Ser Trp Ile Gln Phe
145                 150                 155                 160

Met Ile His Asp Trp Ile Asp His Leu Glu Asp Thr His Gln Ile Glu
                165                 170                 175

Leu Val Ala Pro Lys Glu Val Ala Ser Lys Cys Pro Leu Ser Ser Phe
            180                 185                 190

Arg Phe Leu Lys Thr Lys Glu Val Pro Thr Gly Phe Phe Glu Ile Lys
        195                 200                 205

Thr Gly Ser Gln Asn Ile Arg Thr Pro Trp Trp Asp Ser Ser Val Ile
    210                 215                 220

Tyr Gly Ser Asn Ser Lys Thr Leu Asp Arg Val Arg Thr Tyr Lys Asp
225                 230                 235                 240

Gly Lys Leu Lys Ile Ser Glu Glu Thr Gly Leu Leu Leu His Asp Glu
                245                 250                 255

Asp Gly Leu Ala Ile Ser Gly Asp Ile Arg Asn Ser Trp Ala Gly Val
            260                 265                 270

Ser Ala Leu Gln Ala Leu Phe Ile Lys Glu His Asn Ala Val Cys Asp
        275                 280                 285

Ala Leu Lys Asp Glu Asp Asp Asp Leu Glu Asp Glu Asp Leu Tyr Arg
    290                 295                 300

Tyr Ala Arg Leu Val Thr Ser Ala Val Val Ala Lys Ile His Thr Ile
305                 310                 315                 320

Asp Trp Thr Val Gln Leu Leu Lys Thr Asp Thr Leu Leu Ala Gly Met
                325                 330                 335

Arg Ala Asn Trp Tyr Gly Leu Leu Gly Lys Lys Phe Lys Asp Ser Phe
            340                 345                 350
```

Gly His Ala Gly Ser Ser Ile Leu Gly Gly Val Val Gly Met Lys Lys
355 360 365

Pro Gln Asn His Gly Val Pro Tyr Ser Leu Thr Glu Asp Phe Thr Ser
370 375 380

Val Tyr Arg Met His Ser Leu Leu Pro Asp Gln Leu His Ile Leu Asp
385 390 395 400

Ile Asp Asp Val Pro Gly Thr Asn Lys Ser Leu Pro Leu Ile Gln Glu
405 410 415

Ile Ser Met Arg Asp Leu Ile Gly Arg Lys Gly Glu Glu Thr Met Ser
420 425 430

His Ile Gly Phe Thr Lys Leu Met Val Ser Met Gly His Gln Ala Ser
435 440 445

Gly Ala Leu Glu Leu Met Asn Tyr Pro Met Trp Leu Arg Asp Ile Val
450 455 460

Pro His Asp Pro Asn Gly Gln Ala Arg Pro Asp His Val Asp Leu Ala
465 470 475 480

Ala Leu Glu Ile Tyr Arg Asp Arg Glu Arg Ser Val Pro Arg Tyr Asn
485 490 495

Glu Phe Arg Arg Ser Met Phe Met Ile Pro Ile Thr Lys Trp Glu Asp
500 505 510

Leu Thr Glu Asp Glu Glu Ala Ile Glu Val Leu Asp Asp Val Tyr Asp
515 520 525

Gly Asp Val Glu Glu Leu Asp Leu Leu Val Gly Leu Met Ala Glu Lys
530 535 540

Lys Ile Lys Gly Phe Ala Ile Ser Glu Thr Ala Phe Tyr Ile Phe Leu
545 550 555 560

Ile Met Ala Thr Arg Arg Leu Glu Ala Asp Arg Phe Phe Thr Ser Asp
565 570 575

Phe Asn Glu Thr Ile Tyr Thr Lys Lys Gly Leu Glu Trp Val Asn Thr
580 585 590

Thr Glu Ser Leu Lys Asp Val Ile Asp Arg His Tyr Pro Asp Met Thr
595 600 605

Asp Lys Trp Met Asn Ser Glu Ser Ala Phe Ser Val Trp Asp Ser Pro
610 615 620

Pro Leu Thr Lys Asn Pro Ile Pro Leu Tyr Leu Arg Ile Pro Ser
625 630 635

<210> SEQ ID NO 39
<211> LENGTH: 643
<212> TYPE: PRT
<213> ORGANISM: Capsicum annuum

<400> SEQUENCE: 39

Met Ser Phe Ile Met Ser Ser Leu Arg Asn Leu Phe Leu Ser Pro Leu
1 5 10 15

Arg Ser Phe Ile Gln Lys Asp Phe His Asp Ala Phe Asp Ser Met Thr
20 25 30

Leu Leu Asp Lys Leu Leu Phe Met Met Val His Phe Val Asp Lys Leu
35 40 45

Ile Leu Trp His Arg Leu Pro Val Phe Leu Gly Leu Ala Tyr Leu Ala
50 55 60

Ala Arg Arg His Leu His Gln Glu Tyr Asn Leu Ile Asn Val Gly Arg
65 70 75 80

```
Thr Pro Thr Gly Val Arg Ser Asn Pro Glu Asp Tyr Pro Tyr Arg Thr
                85                  90                  95

Ala Asp Gly Lys Tyr Asn Asp Pro Phe Asn Glu Gly Ala Gly Ser Gln
            100                 105                 110

Phe Ser Phe Phe Gly Arg Asn Val Met Pro Val Asp Gln His Asp Lys
        115                 120                 125

Leu Lys Lys Pro Asp Pro Met Val Val Ala Thr Lys Leu Leu Ala Arg
    130                 135                 140

Lys Asn Phe Met Asp Thr Gly Lys Gln Phe Asn Met Ile Ala Ala Ser
145                 150                 155                 160

Trp Ile Gln Phe Met Ile His Asp Trp Ile Asp His Leu Glu Asp Thr
                165                 170                 175

His Gln Ile Glu Leu Arg Ala Pro Glu Glu Val Ala Ser Glu Cys Pro
            180                 185                 190

Leu Lys Ser Phe Lys Phe Tyr Lys Ser Lys Lys Thr Pro Thr Gly Phe
        195                 200                 205

Tyr Glu Ile Lys Thr Gly Tyr Leu Asn Arg Arg Thr Pro Trp Trp Asp
    210                 215                 220

Gly Ser Ala Ile Tyr Gly Ser Asn Thr Glu Ala Leu Lys Lys Val Arg
225                 230                 235                 240

Thr Phe Glu Asp Gly Lys Leu Lys Leu Ser Ala Asp Gly Leu Leu Glu
                245                 250                 255

Gln Asp Glu Asn Gly Asn Ile Ile Ser Gly Asp Val Arg Asn Pro Trp
            260                 265                 270

Ala Gly Leu Leu Ala Leu Gln Ala Leu Phe Ile Gln Glu His Asn Leu
        275                 280                 285

Val Cys Asp Thr Leu Lys Lys Glu Tyr Pro Lys Leu Glu Asp Glu Asp
    290                 295                 300

Leu Tyr Arg His Ala Arg Leu Val Thr Ser Ala Val Ile Ala Lys Val
305                 310                 315                 320

His Thr Ile Asp Trp Thr Val Glu Leu Leu Lys Thr Asp Thr Leu Leu
                325                 330                 335

Ser Gly Met Arg Ala Asn Trp Tyr Gly Leu Leu Gly Lys Lys Phe Lys
            340                 345                 350

Asp Thr Phe Gly His Val Gly Gly Ser Ser Leu Gly Gly Phe Val Gly
        355                 360                 365

Met Lys Lys Pro Glu Asn His Gly Val Pro Tyr Ser Leu Thr Glu Glu
    370                 375                 380

Phe Val Ser Val Tyr Arg Met His Gln Leu Leu Pro Asp Thr Leu Gln
385                 390                 395                 400

Leu Arg Asn Ile Asp Ala Thr Pro Gly Pro Asn Lys Ser Leu Pro Leu
                405                 410                 415

Thr Asn Glu Ile Pro Met Glu Asp Leu Ile Gly Gly Lys Gly Glu Glu
            420                 425                 430

Asn Leu Ser Arg Ile Gly Tyr Thr Lys Gln Met Val Ser Met Gly His
        435                 440                 445

Gln Ala Cys Gly Ala Leu Glu Leu Met Asn Tyr Pro Ile Trp Met Arg
    450                 455                 460

Asp Leu Ile Pro Gln Asp Val Asp Gly Asn Asp Arg Pro Asp His Ile
465                 470                 475                 480

Asp Leu Ala Ala Leu Glu Ile Tyr Arg Asp Arg Glu Arg Ser Val Ala
                485                 490                 495
```

```
Arg Tyr Asn Glu Phe Arg Arg Arg Met Leu Gln Ile Pro Ile Ser Lys
            500                 505                 510

Trp Glu Asp Leu Thr Asp Asp Glu Glu Ala Ile Lys Met Leu Arg Glu
        515                 520                 525

Val Tyr Gly Asp Asp Val Glu Glu Leu Glu Phe Val Ser Gly Asn Val
    530                 535                 540

Cys Gly Glu Lys Asp Lys Gly Phe Ala Ile Ser Glu Thr Ala Phe Phe
545                 550                 555                 560

Ile Phe Leu Ile Met Ala Ser Arg Arg Leu Glu Ala Asp Lys Phe Phe
                565                 570                 575

Thr Ser Asn Tyr Asn Glu Glu Thr Tyr Thr Lys Lys Gly Leu Glu Trp
            580                 585                 590

Val Asn Thr Thr Glu Ser Leu Lys Asp Val Leu Asp Arg His Tyr Pro
        595                 600                 605

Glu Met Thr Gly Lys Trp Met Asn Ser Asn Ser Ala Phe Ser Val Trp
    610                 615                 620

Asp Ser Ser Pro Glu Pro His Asn Pro Ile Pro Ile Tyr Phe Arg Val
625                 630                 635                 640

Pro Gln Gln


<210> SEQ ID NO 40
<211> LENGTH: 651
<212> TYPE: PRT
<213> ORGANISM: Cercospora beticola

<400> SEQUENCE: 40

Met Ala Ala His Pro Ser Gln Leu Cys Ile Asp Arg Ala Val Gly Pro
1               5                   10                  15

Leu Pro His Leu Ala Ser Tyr Pro Pro Cys Pro Leu Ala Ile Thr Met
            20                  25                  30

Val Tyr Thr Phe Gly Gln Arg Val Leu Val Ala Leu Phe Lys Ala Val
        35                  40                  45

Asn Ala Ile Ile Ala Trp His Lys Leu Pro Pro Leu Ile Gly Ala Leu
    50                  55                  60

Asn Leu Leu Ala Leu Arg Asp Glu Leu Arg Glu Lys Asn Leu Tyr Asp
65                  70                  75                  80

Thr Tyr Pro Thr Glu Asp Phe Gln Gly Thr Thr Lys Ser Asp Pro Ile
                85                  90                  95

Val Asp Thr Lys Phe Ile Cys Ala Arg Asn Ser Asp Gly Leu His Asn
            100                 105                 110

Asp Leu Glu Arg Pro Lys Met Gly Cys Ala Ala Met Arg Phe Gly Arg
        115                 120                 125

Asn Val Pro Arg Gln Tyr Thr Ala Pro Pro Ser Asp His Asp Leu Met
    130                 135                 140

Thr Pro Asp Pro Arg Leu Val Ser Ala Lys Leu Leu Gln Arg Thr Glu
145                 150                 155                 160

Phe Lys Pro Ala Thr Ile Val Asn Leu Leu Ala Ala Ala Trp Ile Gln
                165                 170                 175

Phe Gln Val His Asp Trp Ala Gln His Thr Asn Ser Lys Thr Lys Phe
            180                 185                 190

His His Ile Pro Leu Lys Ala Asp Asp Pro Trp Pro Glu Asn Pro Met
        195                 200                 205

Lys Val Ala Lys Thr Val Gln Asp Glu Pro Leu Asp Glu Glu Asp Gln
    210                 215                 220
```

```
Lys Tyr Pro Ala Tyr Lys Asn Glu Asn Thr His Trp Trp Asp Ala Ser
225                 230                 235                 240

Gln Ile Tyr Gly Ser Thr Glu Glu Ala Thr Arg Lys Leu Arg Gly Lys
                245                 250                 255

His Gln Asp Gly Thr Leu Asp Val Asp Arg Ile Glu Gly Glu His Phe
            260                 265                 270

Leu Pro Arg Gly His Asp Gly Ile Pro Lys Thr Gly Phe Lys Glu Asn
        275                 280                 285

Trp Trp Leu Gly Leu Glu Leu Leu His Thr Leu Phe Ala Leu Glu His
    290                 295                 300

Asn Ala Ile Cys Ser Met Leu Lys Thr Lys Asn Pro Ser Trp Ser Gly
305                 310                 315                 320

Asp Glu Ile Phe Asp Val Ala Arg Leu Ile Asn Cys Ala Leu Met Ala
                325                 330                 335

Lys Ile His Thr Ile Glu Trp Thr Pro Ala Ile Leu Pro His Pro Thr
            340                 345                 350

Leu Asp Ile Gly Met Asn Ala Asn Trp Ser Gly Leu Leu Gly Pro Ser
        355                 360                 365

Trp Ser Lys Leu Phe Ser Asn Phe Gly Lys Ser Glu Ala Phe Thr Gly
    370                 375                 380

Ile Pro Glu Ser Gly Ala Asp Ser Gly Lys Thr Pro Tyr Cys Leu Thr
385                 390                 395                 400

Glu Glu Phe Val Ser Val Tyr Arg Leu His Ser Leu Ile Pro Asp Asp
                405                 410                 415

Val Ala Phe Phe Lys Leu Arg Thr Gly Glu His Thr Ser Asn Ile Pro
            420                 425                 430

Ile Gln Asp Ile Ala Phe Glu Asn Ala Arg Ser Val Phe Glu Gly Pro
        435                 440                 445

Gln Asn Leu Asn Phe Ala Asp Ala Phe Tyr Ser Phe Gly Ile Asn Phe
    450                 455                 460

Pro Gly Ala Ile Thr Ala His Asn Met Pro Ser Phe Leu Arg Asp Leu
465                 470                 475                 480

Lys Lys Pro Asp Gly Glu His Leu Asp Met Gly Cys Val Asp Val Leu
                485                 490                 495

Arg Asp Arg Glu Arg Gly Val Pro Arg Tyr Cys Gln Phe Arg Arg Leu
            500                 505                 510

Phe His Met Pro Val Pro Lys Ser Phe Ser Ala Leu Thr Gly Gly Asn
        515                 520                 525

Ala Thr Leu Ala Thr Glu Leu Ser Gln Val Tyr Asp Gly Asp Ile Glu
    530                 535                 540

Lys Val Asp Leu Leu Ile Gly Cys Leu Cys Glu Pro Leu Pro Lys Gly
545                 550                 555                 560

Phe Gly Phe Ser Asp Thr Ala Phe Arg Val Phe Ile Leu Met Ala Ser
                565                 570                 575

Arg Arg Leu Lys Ser Asp Arg Phe Ile Ala Ser Asp Phe Lys His Glu
            580                 585                 590

Ile Tyr Thr Lys Glu Gly Ile Asp Trp Val Gln Asp Asn Asp Met Arg
        595                 600                 605

Asp Val Leu Val Arg His Phe Pro Asp Leu Arg Ala Pro Leu Lys Asp
    610                 615                 620
```

Val Lys Asn Ala Phe Ala Pro Trp Gly Lys Val Gly Arg Thr Glu Glu
625 630 635 640

Tyr Arg Gly Val Gln Ile Thr Ala Pro Glu Lys
645 650

<210> SEQ ID NO 41
<211> LENGTH: 632
<212> TYPE: PRT
<213> ORGANISM: Cucumis sativus

<400> SEQUENCE: 41

Met Gly Phe Ala Leu Phe Ser Ser Pro Phe Val His Pro Gln Leu Gln
1 5 10 15

Gln Ile Val Ala Lys Met Thr Leu Leu Asp Thr Leu Leu Phe Tyr Val
20 25 30

Val His Phe Val Asp Lys Leu Gly Leu Trp His Arg Leu Pro Val Leu
35 40 45

Leu Gly Leu Ala Tyr Leu Gly Met Arg Arg His Leu His Gln Arg Tyr
50 55 60

Asn Leu Leu His Val Gly Ser Met Tyr Gly Gln Lys Tyr Asp His Gln
65 70 75 80

Gln Phe Cys Tyr Arg Thr Ala Asp Gly Ser Cys Asn His Pro Phe Asp
85 90 95

Ser Leu Val Gly Ser Gln Gly Thr Phe Phe Gly Arg Asn Met Pro Pro
100 105 110

Ser Asn Ser Pro Tyr Gly Val Leu Asp Pro His Pro Thr Val Val Ala
115 120 125

Thr Lys Leu Leu Glu Arg Lys Lys Tyr Ile Asp Asn Gly Lys Gln Phe
130 135 140

Asn Met Ile Ala Cys Ser Trp Ile Gln Phe Met Ile His Asp Trp Ile
145 150 155 160

Asp His Leu Glu Asp Thr Lys Gln Val Glu Leu Thr Ala Pro Glu Glu
165 170 175

Val Ala Asn Gly Cys Pro Leu Lys Ser Phe Lys Phe Phe Gly Thr Lys
180 185 190

Val Val Ser Thr Asp Ser Pro Tyr Leu Lys Thr Gly Thr Leu Asn Thr
195 200 205

Arg Thr Pro Trp Trp Asp Gly Ser Val Ile Tyr Gly Asn Asn Glu Glu
210 215 220

Gly Met Arg Arg Val Arg Ala Phe Gln Asp Gly Lys Met Lys Ile Ala
225 230 235 240

Gly Asp Gly Leu Leu Glu His Asp Glu Lys Gly Ile Pro Ile Ser Gly
245 250 255

Asp Val Arg Asn Cys Trp Ala Gly Phe Ser Leu Leu Gln Ala Leu Phe
260 265 270

Val Lys Glu His Asn Ala Val Cys Asp Met Leu Lys Glu Arg Tyr Pro
275 280 285

Asp Leu Asp Asp Glu Gln Leu Tyr Arg His Ala Arg Leu Val Thr Ser
290 295 300

Ala Val Ile Ala Lys Ile His Thr Ile Asp Trp Thr Val Glu Leu Leu
305 310 315 320

Lys Thr Glu Thr Leu Leu Ala Gly Met Arg Ile Asn Trp Tyr Gly Phe
325 330 335

Leu Gly Lys Lys Phe Lys Asp Thr Phe Gly His Ile Cys Gly Pro Ile
340 345 350

Leu Ser Gly Leu Val Gly Leu Lys Lys Pro Arg Asp His Gly Ile Pro
355 360 365

Tyr Ser Leu Thr Glu Glu Phe Val Ser Val Tyr Arg Met His Cys Leu
370 375 380

Leu Pro Asp Thr Leu Val Ile Arg Asp Leu Asn Ser Thr Asn Ser Asp
385 390 395 400

Tyr Ser Asp Pro Pro Ile Ile Glu Glu Val Pro Met Glu Gln Leu Val
405 410 415

Gly Lys Asp Gly Glu Lys Arg Ser Ala Lys Leu Gly Met Glu Gln Met
420 425 430

Leu Val Ser Met Gly His Gln Ala Cys Gly Ala Leu Ser Leu Trp Asn
435 440 445

Tyr Pro Ser Trp Met Arg Lys Leu Ile Ala His Asp Val Asp Gly Asp
450 455 460

Asp Arg Pro Asp Pro Val Asp Met Ala Ala Met Glu Ile Tyr Arg Asp
465 470 475 480

Arg Glu Arg Gly Val Ala Arg Tyr Asn Glu Phe Arg Arg Asn Leu Leu
485 490 495

Met Ser Pro Ile Ser Lys Trp Glu Asp Leu Thr Asp Asp Asn Glu Val
500 505 510

Val Ser Ala Leu Glu Glu Val Tyr Gly Asn Asp Val Glu Lys Leu Asp
515 520 525

Leu Leu Val Gly Leu His Ala Glu Lys Lys Ile Lys Gly Phe Ala Ile
530 535 540

Ser Glu Thr Ser Phe Phe Ile Phe Leu Leu Ile Ala Ser Arg Arg Leu
545 550 555 560

Glu Ala Asp Arg Phe Phe Thr Thr Asn Tyr Asn Ser Lys Thr Tyr Thr
565 570 575

Glu Glu Gly Leu Glu Trp Val Asn Lys Thr Glu Thr Leu Lys Asp Val
580 585 590

Ile Asp Arg His Phe Pro Asp Met Thr Lys Arg Trp Met Arg Cys Ser
595 600 605

Ser Ala Phe Ser Val Trp Asp Ser Leu Pro Asn Pro Thr Asn Tyr Ile
610 615 620

Pro Leu Tyr Leu Arg Pro Ala Thr
625 630

<210> SEQ ID NO 42
<211> LENGTH: 643
<212> TYPE: PRT
<213> ORGANISM: Cucumis sativus

<400> SEQUENCE: 42

Met Leu Ser Gln Leu Leu Lys Pro Ile Lys Ile Val Leu Arg Gly Glu
1 5 10 15

Leu Gln Lys Phe Val His Lys Asp Phe His Glu Val Val Gln Arg Met
20 25 30

Thr Val Ile Asp Thr Phe Leu Phe Leu Ile Val His Phe Val Asp Lys
35 40 45

Leu Gly Ile Trp His Lys Leu Pro Val Ile Leu Gly Leu Leu Tyr Leu
50 55 60

```
Ala Val Arg Arg His Leu His Gln Glu Tyr Asn Leu Phe Asn Val Gly
65                  70                  75                  80

Arg Thr Pro Val Gly Val Arg Phe Asn Pro Val Asp Phe Pro Tyr Arg
                85                  90                  95

Thr Ala Asp Gly Lys Tyr Asn Asp Pro Phe Asn Glu Gly Ala Gly Ala
            100                 105                 110

Gln Gly Ser Phe Phe Gly Arg Asn Ile His Pro Val Asp Gln Ser Lys
        115                 120                 125

Thr Leu Leu Lys Pro Asp Pro Met Val Val Ala Thr Lys Leu Leu Ala
    130                 135                 140

Arg Arg Lys Leu Ile Asp Thr Gly Lys Gln Phe Asn Met Ile Ala Ala
145                 150                 155                 160

Ser Trp Ile Gln Phe Met Ile His Asp Trp Ile Asp His Leu Glu Asp
                165                 170                 175

Thr Lys Gln Val Glu Leu Val Ala Pro Arg Glu Val Ala Ser Glu Cys
            180                 185                 190

Pro Leu Lys Ser Phe Lys Phe Phe Lys Thr Lys Gln Val Ser Thr Gly
        195                 200                 205

Phe Phe Asp Asn Lys Thr Gly Ser Ile Asn Val Arg Thr Pro Trp Trp
    210                 215                 220

Asp Gly Ser Val Leu Tyr Gly Ser Asn Ala Glu Lys Leu Gly Lys Val
225                 230                 235                 240

Arg Thr Tyr Lys Asp Gly Lys Leu Lys Ile Ala Asp Asp Asp Leu Leu
                245                 250                 255

Leu His Asp Asn Asp Gly Val Ala Ile Ser Gly Asp Val Arg Asn Ser
            260                 265                 270

Trp Ala Gly Val Ser Thr Leu Gln Ala Leu Phe Ile Arg Glu His Asn
        275                 280                 285

Ala Val Cys Asp Ala Leu Lys Lys Glu Asp Glu Asp Leu Glu Asp Glu
    290                 295                 300

Asp Leu Tyr Arg Tyr Ala Arg Leu Val Thr Ser Ala Val Ile Ala Lys
305                 310                 315                 320

Val His Thr Ile Asp Trp Thr Val Glu Leu Leu Lys Met Asp Thr Leu
                325                 330                 335

Leu Ala Gly Met Arg Gly Asn Trp Tyr Gly Leu Leu Gly Lys Lys Phe
            340                 345                 350

Lys Asp Thr Phe Gly His Val Gly Gly Ala Ile Leu Gly Gly Leu Val
        355                 360                 365

Gly Leu Lys Lys Pro Asp Asn His Gly Val Pro Tyr Ser Leu Thr Glu
    370                 375                 380

Glu Phe Ala Ser Val Tyr Arg Met His Ser Leu Leu Pro Asp Asp Phe
385                 390                 395                 400

His Leu Arg Asp Ile Ser Val Asp Pro Asp His Asn Lys Ser Pro Pro
                405                 410                 415

Leu Val Glu Lys Val Pro Met Ala Asn Met Ile Gly His Lys Gly Glu
            420                 425                 430

Glu Thr Ser Lys Lys Met Gly Phe Thr Ala Leu Leu Val Ser Met Gly
        435                 440                 445

His Gln Ser Ser Gly Ala Leu Glu Leu Trp Asn Tyr Pro Gln Trp Leu
    450                 455                 460

Arg Asp Leu Ile Pro His Asp Met Asp Gly Lys Asp Arg Ala Asp His
465                 470                 475                 480
```

```
Ile Asp Leu Ala Ala Leu Glu Val Tyr Arg Asp Arg Glu Arg Arg Val
                485                 490                 495

Ala Arg Tyr Asn Asp Phe Arg Arg Gly Leu Phe Leu Ile Pro Ile Ser
            500                 505                 510

Lys Trp Glu Asp Leu Thr Asp Asp Glu Gly Ala Ile Glu Val Leu Arg
        515                 520                 525

Glu Val Tyr Gly Asp Asp Val Glu Glu Leu Asp Ile Leu Val Gly Leu
    530                 535                 540

Met Ala Glu Lys Lys Ile Lys Gly Phe Ala Ile Ser Glu Thr Ala Phe
545                 550                 555                 560

Val Ile Phe Leu Ile Met Ala Ser Arg Arg Leu Glu Ala Asp Arg Phe
                565                 570                 575

Phe Thr Ser His Phe Asn Glu Glu Thr Tyr Thr Lys Lys Gly Leu Glu
            580                 585                 590

Trp Val Asn Thr Thr Glu Ser Leu Lys Asp Val Ile Glu Arg His Tyr
        595                 600                 605

Pro Glu Ile Ser Asn Lys Trp Met Asn Ser Ser Ser Ala Phe Ser Val
    610                 615                 620

Trp Asp Ser Pro Pro Asn Lys Pro Asn Pro Ile Pro Ile Tyr Phe Arg
625                 630                 635                 640

Leu Pro His


<210> SEQ ID NO 43
<211> LENGTH: 645
<212> TYPE: PRT
<213> ORGANISM: Cucumis sativus

<400> SEQUENCE: 43

Met Leu Ser Val Leu Leu Lys Pro Ile Lys Ala Ile Leu Leu Leu Leu
1               5                   10                  15

Val Arg Leu Phe Val His Arg Asp Phe His Glu Leu Ala Arg Arg Met
            20                  25                  30

Thr Val Leu Asp Ile Tyr Arg Phe Leu Ile Ile His Ser Ile Asp Lys
        35                  40                  45

Met Gly Ile Trp Pro Lys Leu Pro Val Leu Leu Gly Leu Leu Tyr Leu
    50                  55                  60

Ala Ala Arg Arg His Leu His Gln Arg Tyr Ser Leu Tyr Lys Val Gly
65                  70                  75                  80

Lys Asn Thr Pro Val Gly Val Arg Ser His Pro Glu Asp Cys Pro Tyr
                85                  90                  95

Arg Thr Pro Asp Gly Arg Tyr Thr Asp Pro Phe Asp Asp Asp Ala Gly
            100                 105                 110

Ser Gln Gly Thr Phe Phe Gly Arg Asn Val His Pro Val Asp Gln Ser
        115                 120                 125

Glu Arg Leu Leu Lys Pro Asp Pro Met Val Val Ala Thr Lys Leu Leu
    130                 135                 140

Ala Arg Lys Lys Leu Ile Asp Thr Gly Lys Gln Phe Asn Val Ile Ala
145                 150                 155                 160

Ala Ser Trp Ile Gln Phe Met Val His Asp Trp Met Asp His Leu Glu
                165                 170                 175

Asp Thr Lys Gln Val Glu Leu Val Ala Pro Ser Asp Val Ala Lys Ser
            180                 185                 190

Cys Pro Leu Lys Ser Phe Lys Phe Phe Lys Thr Lys Glu Glu Ser Thr
        195                 200                 205
```

-continued

```
Asp Leu Phe Asp Ile Arg Thr Gly Ser Ile Asn Ile Arg Thr Pro Trp
    210                 215                 220

Trp Asp Gly Ser Val Leu Tyr Gly Ser Asn Glu Gln Met Leu Asn Lys
225                 230                 235                 240

Val Arg Thr Tyr Glu Asp Gly Lys Leu Lys Ile Ala Asp Asp Gly Leu
                245                 250                 255

Leu Pro His Asp Lys Asp Gly Ile Ala Ile Ser Gly Asp Val Arg Asn
            260                 265                 270

Ser Trp Ala Gly Val Ser Thr Leu Gln Ala Leu Phe Ile Lys Glu His
        275                 280                 285

Asn Ala Val Cys Asp Val Leu Lys Lys Glu Tyr Gly Asn Met Glu Asp
    290                 295                 300

Glu Glu Leu Tyr Arg Arg Ala Arg Leu Val Thr Ser Ala Val Ile Ala
305                 310                 315                 320

Lys Val His Thr Ile Asp Trp Thr Val Glu Leu Leu Lys Thr Asp Thr
                325                 330                 335

Leu Leu Ala Gly Met Arg Gly Asn Trp Tyr Gly Leu Leu Gly Lys Lys
            340                 345                 350

Phe Lys Asp Thr Phe Gly His Val Gly Gly Ser Ile Leu Gly Gly Leu
        355                 360                 365

Val Gly Leu Lys Lys Pro Asn Asn His Gly Val Thr Tyr Ser Leu Thr
    370                 375                 380

Glu Glu Phe Thr Ser Val Tyr Arg Met His Gln Leu Leu Pro Asp Ser
385                 390                 395                 400

Phe Tyr Leu Arg Asp Val Thr Val Asp Pro Asp Gln His Asn Lys Ser
                405                 410                 415

Pro Pro Leu Ile Glu Tyr Val Pro Met Ala Asn Met Ile Gly His Lys
            420                 425                 430

Gly Glu Glu Thr Ser Lys Lys Met Gly Phe Thr Ala Leu Leu Val Ser
        435                 440                 445

Met Gly His Gln Ala Ser Gly Ala Leu Glu Leu Phe Asn Tyr Pro Leu
    450                 455                 460

Trp Leu Arg Asp Leu Ile Ala His Asp Met Asp Asn Lys Asp Arg Pro
465                 470                 475                 480

Asp His Ile Asp Leu Ala Ala Leu Glu Val Tyr Arg Asp Arg Glu Arg
                485                 490                 495

Arg Val Ala Arg Tyr Asn Asp Phe Arg Arg Gly Leu Phe Leu Ile Pro
            500                 505                 510

Ile Ser Lys Trp Glu Asp Leu Thr Asp Asp Lys Asp Thr Ile Lys Val
        515                 520                 525

Leu Arg Glu Val Tyr Asp Asp Asp Val Glu Gln Leu Asp Ile Leu Val
    530                 535                 540

Gly Leu Met Ala Glu Lys Lys Ile Lys Gly Phe Ala Ile Ser Glu Thr
545                 550                 555                 560

Ala Phe Val Ile Phe Leu Ile Met Ala Ser Arg Arg Leu Glu Ala Asp
                565                 570                 575

Ser Phe Phe Thr Cys Tyr Tyr Asn Glu Glu Thr Tyr Thr Lys Lys Gly
            580                 585                 590

Leu Glu Trp Val Lys Thr Thr Glu Ser Leu Lys Asp Val Ile Glu Arg
        595                 600                 605

His His Pro Glu Ile Ser Lys Lys Trp Ile Asn Ser Ser Ser Ala Phe
    610                 615                 620
```

Ser Val Trp Asp Ser Pro Pro Asn Lys Pro Asn His Val Pro Leu Tyr
625 630 635 640

Leu Arg Ile Pro Asn
645

<210> SEQ ID NO 44
<211> LENGTH: 639
<212> TYPE: PRT
<213> ORGANISM: Solanum lycopersicum

<400> SEQUENCE: 44

Met Ser Phe Val Met Leu Lys Asn Leu Leu Leu Ser Ser Leu Arg Lys
1 5 10 15

Phe Ile His Lys Asp Phe His Glu Ile Phe Asp Lys Met Thr Leu Ile
20 25 30

Asp Lys Leu Phe Phe Leu Ile Val His Phe Ile Asp Lys His Asn Phe
35 40 45

Trp His Arg Leu Pro Val Phe Phe Gly Leu Leu Tyr Leu Gly Ala Arg
50 55 60

Arg Ser Leu His Gln Gln Tyr Asn Leu Ile Asn Val Gly Arg Thr Pro
65 70 75 80

Thr Gly Val Arg Ser Asn Pro Ala Asp Tyr Pro Tyr Arg Thr Ala Asp
85 90 95

Gly Lys Phe Asn Asp Pro Phe Asn Glu Gly Thr Gly Ser Gln Phe Ser
100 105 110

Phe Phe Gly Arg Asn Met Met Pro Leu His Gln Asn Asn Lys Leu Lys
115 120 125

Lys Pro Asp Pro Met Val Val Ala Thr Lys Leu Leu Ala Arg Arg Lys
130 135 140

Phe Ile Asp Thr Gly Lys Gln Phe Asn Met Ile Ala Ala Ser Trp Ile
145 150 155 160

Gln Phe Met Val His Asp Trp Ile Asp His Leu Glu Asp Thr Gln Gln
165 170 175

Val Glu Leu Arg Ala Pro Lys Glu Val Ala Asn Glu Cys Pro Leu Lys
180 185 190

Ser Phe Arg Phe Asn Lys Ser Lys Glu Thr Pro Thr Asp Phe Tyr Glu
195 200 205

Ile Lys Thr Gly His Leu Asn Ser Arg Thr Pro Trp Trp Asp Gly Ser
210 215 220

Val Ile Tyr Gly Ser Asn Glu Asp Val Leu Lys Lys Val Arg Thr Phe
225 230 235 240

Arg Asp Gly Lys Leu Lys Leu Gly Glu Asn Gly Leu Ile Gln Gln Asp
245 250 255

Glu Asn Gly Lys Ile Ile Ser Gly Asp Val Arg Asn Thr Trp Ala Gly
260 265 270

Leu Leu Thr Leu Gln Ala Leu Phe Val Gln Glu His Asn Ala Val Cys
275 280 285

Asp Thr Leu Lys Lys Glu Tyr Pro Glu Leu Glu Asp Glu Glu Leu Tyr
290 295 300

Arg His Ala Arg Leu Val Thr Ser Ala Val Ile Ala Lys Val His Thr
305 310 315 320

Ile Asp Trp Thr Val Gln Leu Leu Lys Thr Asp Thr Met Leu Ala Gly
325 330 335

Met Arg Ala Asn Trp Tyr Gly Leu Leu Gly Lys Lys Phe Lys Asp Thr
340 345 350

Phe Gly His Val Gly Ser Ile Leu Ser Gly Val Val Gly Met Lys Lys
355 360 365

Pro Glu Asn His Gly Val Pro Tyr Ser Leu Thr Glu Glu Phe Thr Ser
370 375 380

Val Tyr Arg Met His Gln Leu Leu Pro Asp Thr Leu Gln Leu Arg Asn
385 390 395 400

Ile Asp Ala Thr Pro Gly Pro Asn Lys Ser Leu Pro Leu Thr Asn Glu
405 410 415

Ile Pro Met Glu Glu Val Val Gly Ser Lys Gly Lys Glu Asn Leu Ser
420 425 430

Arg Ile Gly Phe Thr Lys Gln Met Val Ser Met Gly His Gln Ala Ser
435 440 445

Gly Ala Leu Glu Leu Trp Asn Tyr Pro Val Trp Met Arg Asp Leu Ile
450 455 460

Ala Gln Asp Val Asp Gly Thr Asp Arg Pro Asp Pro Ile Asp Leu Ala
465 470 475 480

Ala Leu Glu Ile Tyr Arg Asp Arg Glu Arg Ser Val Pro Arg Tyr Asn
485 490 495

Asp Phe Arg Arg Gly Met Leu Gln Ile Pro Ile Ser Lys Trp Glu Asp
500 505 510

Leu Thr Asp Asp Glu Glu Ala Ile Lys Thr Leu Gly Glu Val Tyr Asp
515 520 525

Asp Asp Ile Gln Glu Leu Asp Leu Leu Val Gly Leu Met Ala Glu Lys
530 535 540

Lys Ile Lys Gly Phe Ala Ile Ser Glu Thr Ala Phe Asn Ile Phe Leu
545 550 555 560

Leu Met Ala Ile Arg Arg Leu Glu Ala Asp Arg Phe Phe Thr Ser Asn
565 570 575

Tyr Asn Asp Glu Thr Tyr Thr Lys Lys Gly Leu Glu Trp Val Asn Thr
580 585 590

Thr Glu Ser Leu Lys Asp Val Leu Asp Arg His Tyr Pro Glu Met Thr
595 600 605

Asp Lys Trp Met Asn Ser Asn Ser Ala Phe Ser Val Trp Asp Ser Ser
610 615 620

Pro Gln Pro His Asn Pro Ile Pro Leu Tyr Phe Arg Val Pro Gln
625 630 635

<210> SEQ ID NO 45
<211> LENGTH: 632
<212> TYPE: PRT
<213> ORGANISM: Solanum lycopersicum

<400> SEQUENCE: 45

Met Ala Phe Ser Ile Ser Leu Pro Asp Phe Val His Pro Gln Leu Arg
1 5 10 15

His Val Val Ala Lys Met Ser Phe Phe Asp Thr Ile Leu Phe Tyr Val
20 25 30

Val His Leu Val Asp Lys Phe Asp Leu Trp His Arg Leu Pro Val Leu
35 40 45

Leu Gly Ala Ala Tyr Leu Gly Ile Arg Arg His Leu His Gln Arg Tyr
50 55 60

Asn Leu Leu His Val Gly Lys Val Asn Gly Lys Lys Tyr Asp Thr Glu
65 70 75 80

Glu Phe Thr Tyr Arg Thr Ala Asp Gly Ser Cys Asn His Pro Val Asp
85 90 95

His Leu Val Gly Ser Gln Gly Thr Phe Phe Gly Arg Asn Met Leu Pro
100 105 110

Ser Thr Ser Ser Tyr Ala Leu Leu Glu Pro His Pro Val Thr Val Ala
115 120 125

Ser Lys Leu Leu Glu Arg Arg Lys Tyr Thr Asp Cys Gly Gly Gln Phe
130 135 140

Asn Met Ile Ala Cys Ala Trp Leu Gln Phe Met Ile His Asp Trp Asn
145 150 155 160

Asp His Met Glu Asp Thr Glu Gln Val Glu Leu Arg Ala Pro Gln Asp
165 170 175

Val Ala Ala Gly Cys Pro Leu Lys Ser Phe Lys Phe Leu Lys Thr Lys
180 185 190

Lys Leu Pro Thr Gly Ser Pro Asp Leu Lys Phe Gly His Leu Asn Ser
195 200 205

Arg Thr Pro Trp Trp Asp Gly Ser Val Ile Tyr Gly Asn Asn Glu Glu
210 215 220

Gly Met Ile Arg Val Arg Arg Phe Lys Asp Gly Lys Leu Arg Leu Ser
225 230 235 240

Gly Asp Gly Leu Leu Glu His Asp Asp Lys Gly Ile Pro Ile Ser Gly
245 250 255

Asp Val Arg Asn Tyr Trp Ala Gly Tyr Ser Leu Leu Gln Ala Leu Phe
260 265 270

Val Lys Glu His Asn Ala Ile Cys Asp Met Leu Lys Glu His Tyr Pro
275 280 285

Glu Phe Asp Asp Glu Lys Val Tyr Arg His Ala Arg Leu Ile Thr Ser
290 295 300

Ala Val Ile Ala Lys Ile His Thr Ile Asp Trp Thr Leu Glu Ile Val
305 310 315 320

Lys Thr Asp Thr Leu Met Ala Gly Met Arg Ile Asn Trp Tyr Gly Leu
325 330 335

Leu Gly Lys Arg Val Lys Asp Leu Leu Gly Pro Lys Phe Gly Pro Val
340 345 350

Leu Ser Gly Leu Val Gly Leu Lys Lys Pro Arg Asp His Gly Thr Pro
355 360 365

Tyr Ser Leu Thr Glu Glu Phe Val Ser Val Tyr Arg Met His Ser Leu
370 375 380

Leu Pro Asp Thr Ile Val Leu Arg Asp Leu Lys Ser Thr Thr Ser Glu
385 390 395 400

Asp Lys Ser Leu Pro Ile Gln Asp Glu Ile Pro Met Arg Glu Met Ile
405 410 415

Gly Lys Glu Gly Glu Lys Asn Leu Ser Lys Ile Gly Met Glu Gln Met
420 425 430

Leu Val Ser Met Gly His Gln Ser Ser Gly Ala Gly Thr Leu Trp Asn
435 440 445

Phe Pro Ser Trp Met Arg Asn Leu Val Pro His Asp Ile Asp Gly Asp
450 455 460

Asp Arg Pro Asp Ser Ile Asp Met Ala Ala Leu Asp Ile Tyr Arg Asp
465 470 475 480

Arg Glu Arg Gly Val Pro Arg Tyr Asn Glu Phe Arg Arg Asn Leu Leu
485 490 495

Met Val Pro Ile Ser Lys Trp Glu Asp Leu Thr Asn Asp Glu Glu Val
500 505 510

Ile Glu Ala Leu Gln Glu Val Tyr Gly Asp Asp Ile Glu Lys Leu Asp
515 520 525

Leu Gln Ile Gly Leu His Ala Glu Lys Lys Ile Lys Gly Phe Ala Ile
530 535 540

Ser Glu Thr Ala Phe Phe Ile Phe Leu Leu Ile Ala Ser Arg Arg Leu
545 550 555 560

Glu Ala Asp Arg Phe Phe Thr Thr Asp Phe Asn Ser Arg Thr Tyr Thr
565 570 575

Glu Lys Gly Phe Glu Trp Val Asn Lys Thr Glu Thr Leu Lys Asp Val
580 585 590

Ile Asp Arg Tyr Phe Pro Glu Met Thr Glu Lys Tyr Met Arg Cys Thr
595 600 605

Ser Ala Phe Ser Val Trp Ser Ser Asp Pro Asp Pro Lys His Tyr Leu
610 615 620

Pro Leu Tyr Leu Arg Pro Ala Thr
625 630

<210> SEQ ID NO 46
<211> LENGTH: 632
<212> TYPE: PRT
<213> ORGANISM: Nicotiana attenuata

<400> SEQUENCE: 46

Met Val Phe Ser Phe Ser Leu Thr Ser Phe Val His Pro Gln Leu Arg
1 5 10 15

His Val Val Gly Lys Met Ser Leu Phe Asp Thr Ile Leu Phe Tyr Val
20 25 30

Val His Leu Leu Asp Lys Phe Asp Leu Trp His Arg Leu Pro Val Leu
35 40 45

Leu Gly Leu Ala Tyr Leu Gly Leu Arg Arg His Leu His Gln Arg Tyr
50 55 60

His Leu Leu His Val Gly Lys Val Asn Gly Lys Lys Tyr Asp Thr Glu
65 70 75 80

Glu Phe Ser Tyr Arg Thr Ala Asp Gly Thr Cys Asn His Pro Val Asp
85 90 95

His Leu Val Gly Ser His Gly Thr Phe Phe Gly Arg Asn Met Pro Pro
100 105 110

Ser Thr Ser Thr Tyr Gly Leu Leu Glu Pro His Pro Ala Thr Val Ala
115 120 125

Thr Lys Leu Leu Glu Arg Arg Lys Cys Thr Asp Cys Gly Ser Gln Leu
130 135 140

Asn Met Ile Gly Cys Ala Trp Val Gln Phe Met Ile His Asp Trp Asn
145 150 155 160

Asp His Met Glu Asp Thr Glu Gln Val Glu Leu Arg Ala Pro Glu Asp
165 170 175

Val Ala Ala Gly Cys Pro Leu Lys Ser Phe Lys Phe Phe Lys Thr Arg
180 185 190

Lys Val Pro Thr Asp Ser Pro Asp Pro Lys Phe Gly His Leu Asn Ser
195 200 205

Arg Thr Pro Trp Trp Asp Gly Ser Val Ile Tyr Gly Asn Asn Lys Glu
210 215 220

```
Gly Met Ile Arg Val Arg Thr Phe Lys Asp Gly Lys Leu Arg Val Ser
225                 230                 235                 240

Gly Asp Gly Leu Leu Glu His Asp Asn Asn Gly Ile Pro Ile Ser Gly
                245                 250                 255

Asp Val Arg Asn Asn Trp Ala Gly Phe Ser Leu Leu Gln Ala Leu Phe
            260                 265                 270

Met Lys Glu His Asn Ala Ile Cys Asp Met Leu Lys Glu His Tyr Pro
        275                 280                 285

Glu Phe Asp Asp Glu Lys Leu Tyr Arg His Ala Arg Leu Thr Thr Ser
    290                 295                 300

Ala Val Ile Ala Lys Ile His Thr Leu Asp Leu Ser Ile Glu Leu Ala
305                 310                 315                 320

Lys Thr Asp Thr Val Val Ala Gly Thr Arg Ile Asn Trp Tyr Gly Phe
                325                 330                 335

Leu Gly Lys Lys Ile Lys Asp Leu Leu Gly Leu Lys Phe Gly Pro Ile
            340                 345                 350

Leu Ser Gly Leu Val Gly Leu Lys Arg Pro Arg Asp His Gly Thr Pro
        355                 360                 365

Tyr Ser Leu Thr Glu Glu Phe Val Ser Val Tyr Arg Met His Ser Leu
    370                 375                 380

Leu Pro Asp Lys Ile Ile Leu Arg Asp Leu Lys Ser Thr Thr Ser Glu
385                 390                 395                 400

Asp Lys Ser Leu Pro Ile Gln Glu Glu Ile Pro Met Thr Glu Met Ile
                405                 410                 415

Gly Lys Glu Gly Glu Lys Ser Leu Ser Lys Ile Gly Ile Glu Gln Met
            420                 425                 430

Leu Val Ser Met Gly His Gln Ser Cys Gly Ala Ala Thr Leu Trp Asn
        435                 440                 445

Tyr Pro Thr Trp Met Arg Asn Leu Val Pro His Asp Val Asp Gly Glu
    450                 455                 460

Glu Arg Pro Asp Leu Val Asp Met Ala Ala Leu Glu Ile Tyr Arg Asp
465                 470                 475                 480

Arg Glu Arg Gly Val Pro Arg Tyr Asn Glu Phe Arg Arg Asn Leu Leu
                485                 490                 495

Met Ile Pro Ile Ser Lys Trp Glu Asp Leu Thr Asp Asp Glu Glu Val
            500                 505                 510

Ile Glu Ala Leu Gln Glu Val Tyr Gly Asp Asp Val Glu Lys Leu Asp
        515                 520                 525

Leu Gln Val Gly Leu His Ala Glu Lys Lys Ile Lys Gly Phe Ala Ile
    530                 535                 540

Ser Glu Thr Ala Phe Asn Ile Phe Leu Leu Ile Ala Ser Arg Arg Leu
545                 550                 555                 560

Glu Ala Asp Arg Phe Phe Thr Thr Asn Phe Asn Ala Arg Thr Tyr Thr
                565                 570                 575

Glu Lys Gly Phe Glu Trp Val Asn Lys Thr Glu Thr Leu Lys Asp Val
            580                 585                 590

Ile Asp Arg His Phe Pro Glu Met Thr Glu Lys Tyr Met Arg Cys Thr
        595                 600                 605

Ser Ala Phe Ala Val Trp Asn Ser Asp Pro Asn Pro Arg Arg Tyr Leu
    610                 615                 620

Pro Leu Tyr Leu Arg Pro Ala Thr
625                 630
```

<210> SEQ ID NO 47
<211> LENGTH: 643
<212> TYPE: PRT
<213> ORGANISM: Nicotiana attenuata

<400> SEQUENCE: 47

```
Met Ser Leu Val Met Ala Ser Leu Lys Asn Leu Leu Leu Ser Pro Leu
1               5                   10                  15

Arg Gly Phe Ile His Lys Asp Phe His Asp Ile Phe Glu Arg Met Thr
            20                  25                  30

Leu Leu Asp Lys Leu Phe Phe Leu Ile Val His Phe Val Asp Lys Leu
        35                  40                  45

Asn Leu Trp His Arg Leu Pro Val Phe Leu Gly Leu Leu Tyr Leu Gly
    50                  55                  60

Ala Arg Arg His Leu His Gln Glu Tyr Asn Leu Ile Asn Val Gly Lys
65                  70                  75                  80

Thr Pro Val Gly Val Arg Ser Asn Pro Ala Asp His Pro Tyr Arg Thr
                85                  90                  95

Ala Asp Gly Lys Tyr Asn Asp Pro Phe Asn Glu Gly Ala Gly Ser Glu
            100                 105                 110

Leu Ser Phe Phe Gly Arg Asn Met Leu Pro Val Asp Gln His Asn Gln
        115                 120                 125

Leu Lys Lys Pro Asp Pro Met Val Val Ala Thr Lys Leu Leu Ala Arg
    130                 135                 140

Arg Asn Val Val Asp Thr Gly Lys Gln Phe Asn Met Ile Ala Ala Ser
145                 150                 155                 160

Trp Ile Gln Phe Met Ile His Asp Trp Ile Asp His Leu Glu Asp Thr
                165                 170                 175

Lys Gln Ile Glu Leu Arg Ala Pro Glu Glu Val Ala Ser Gln Cys Pro
            180                 185                 190

Leu Lys Ser Phe Lys Phe Phe Lys Thr Lys Glu Ile Pro Thr Gly Phe
        195                 200                 205

Tyr Glu Ile Lys Thr Gly His Leu Asn Arg Arg Thr Pro Trp Trp Asp
    210                 215                 220

Gly Ser Ala Ile Tyr Gly Ser Asn Ala Glu Val Leu Lys Lys Val Arg
225                 230                 235                 240

Thr Phe Lys Tyr Gly Lys Leu Lys Leu Ser Ala Asp Gly Leu Leu Glu
                245                 250                 255

Ile Asp Glu Asn Gly Lys Ile Ile Ser Gly Asp Val Arg Asn Thr Trp
            260                 265                 270

Ala Gly Leu Ser Ala Leu Gln Ala Leu Phe Val Gln Glu His Asn Ser
        275                 280                 285

Val Cys Asp Val Leu Lys Lys Glu Tyr Pro Glu Leu Glu Asp Glu Asp
    290                 295                 300

Leu Tyr Arg His Ala Arg Leu Val Thr Ser Ala Val Ile Ala Lys Val
305                 310                 315                 320

His Thr Ile Asp Trp Thr Val Glu Leu Leu Lys Thr Asp Thr Leu Leu
                325                 330                 335

Ala Gly Met Arg Ala Asn Trp Tyr Gly Leu Leu Gly Lys Lys Phe Lys
            340                 345                 350

Asp Thr Phe Gly His Val Gly Gly Ser Ile Leu Gly Gly Phe Val Gly
        355                 360                 365

Met Lys Lys Pro Glu Asn Tyr Gly Val Pro Tyr Ser Leu Thr Glu Glu
    370                 375                 380
```

```
Phe Thr Ser Val Tyr Arg Met His Gln Leu Leu Pro Asp Asn Leu Gln
385                 390                 395                 400

Leu Arg Asn Ile Asp Ala Thr Pro Gly Pro Asn Lys Ser Leu Pro Leu
                405                 410                 415

Thr Asn Glu Ile Pro Met Glu Asp Leu Ile Gly Ser Lys Gly Glu Glu
            420                 425                 430

Asn Leu Ala Arg Ile Gly Phe Thr Lys Gln Met Val Ser Met Gly His
        435                 440                 445

Gln Ala Cys Gly Ala Leu Glu Leu Trp Asn Tyr Pro Met Trp Met Arg
    450                 455                 460

Asp Leu Ile Pro Gln Asp Val Asp Gly Thr Asp Arg Pro Asp His Val
465                 470                 475                 480

Asp Leu Ala Ala Leu Glu Ile Tyr Arg Asp Arg Glu Arg Ser Val Ala
                485                 490                 495

Arg Tyr Asn Glu Phe Arg Arg Gly Met Leu Gln Ile Pro Ile Ser Lys
            500                 505                 510

Trp Glu Asp Leu Thr Asp Asp Glu Glu Val Ile Asn Thr Leu Arg Glu
        515                 520                 525

Val Tyr Gly Asp Asp Val Glu Glu Leu Asp Leu Met Val Gly Met Ala
    530                 535                 540

Ala Glu Lys Lys Ile Lys Gly Phe Ala Ile Ser Glu Thr Ala Phe Phe
545                 550                 555                 560

Ile Phe Leu Ile Met Ala Ser Arg Arg Leu Glu Ala Asp Arg Phe Phe
                565                 570                 575

Thr Ser Asn Tyr Asn Glu Glu Thr Tyr Thr Lys Lys Gly Leu Glu Trp
            580                 585                 590

Val Asn Thr Thr Glu Ser Leu Lys Asp Val Leu Asp Arg His Tyr Pro
        595                 600                 605

Glu Met Thr Glu Lys Trp Met Asn Ser Ser Ser Ala Phe Ser Val Trp
    610                 615                 620

Asp Ser Ser Pro Glu Pro His Asn Pro Ile Pro Leu Tyr Phe Arg Val
625                 630                 635                 640

Pro Pro Gln
```

<210> SEQ ID NO 48
<211> LENGTH: 643
<212> TYPE: PRT
<213> ORGANISM: Nicotiana tabacum

<400> SEQUENCE: 48

```
Met Ser Leu Val Met Asp Ser Leu Lys Asn Leu Leu Leu Ser Pro Leu
1               5                   10                  15

Arg Gly Phe Ile His Lys Asp Leu His Asp Ile Phe Glu Arg Met Thr
            20                  25                  30

Leu Leu Ser Lys Leu Leu Phe Leu Ile Val His Leu Val Asp Lys Leu
        35                  40                  45

Asn Leu Trp His Arg Leu Pro Val Leu Leu Gly Leu Leu Tyr Leu Gly
    50                  55                  60

Ala Arg Arg His Leu His Gln Glu Tyr Asn Leu Ile Asn Val Gly Lys
65                  70                  75                  80

Thr Pro Ile Gly Val Arg Ser Asn Pro Ala Asp His Pro Tyr Arg Thr
                85                  90                  95

Ala Asp Gly Lys Tyr Asn Asp Pro Phe Asn Glu Gly Ala Gly Ser Glu
            100                 105                 110
```

```
Leu Ser Phe Phe Gly Arg Asn Met Leu Pro Val Asp Gln His Asn Gln
        115                 120                 125

Leu Lys Lys Pro Asp Pro Met Val Val Ala Thr Lys Leu Leu Ala Arg
    130                 135                 140

Arg Asn Phe Val Asp Thr Gly Lys Gln Phe Asn Met Ile Ala Ala Ser
145                 150                 155                 160

Trp Ile Gln Phe Met Ile His Asp Trp Ile Asp His Leu Glu Asp Thr
                165                 170                 175

Lys Gln Ile Glu Leu Lys Ala Ala Glu Glu Val Ala Ser Gln Cys Pro
            180                 185                 190

Leu Lys Ser Phe Arg Phe Phe Lys Thr Lys Glu Ile Pro Thr Gly Phe
        195                 200                 205

Tyr Glu Ile Lys Thr Gly His Leu Asn Thr Arg Thr Pro Trp Trp Asp
    210                 215                 220

Gly Ser Ala Ile Tyr Gly Ser Asn Ala Glu Val Leu Lys Lys Val Arg
225                 230                 235                 240

Thr Phe Lys Asp Gly Lys Leu Lys Leu Ser Ala Asp Gly Leu Leu Glu
                245                 250                 255

Ile Asp Lys Asn Gly Lys Ile Ile Ser Gly Asp Val Arg Asn Thr Trp
            260                 265                 270

Ala Gly Leu Ser Ala Leu Gln Ala Leu Phe Val Gln Glu His Asn Ser
        275                 280                 285

Val Cys Asp Ala Leu Lys Lys Glu Tyr Pro Glu Leu Glu Glu Glu Asp
    290                 295                 300

Leu Tyr Arg His Ala Arg Leu Val Thr Ser Ala Val Ile Ala Lys Val
305                 310                 315                 320

His Thr Ile Asp Trp Thr Val Glu Leu Leu Lys Thr Asp Thr Leu Leu
                325                 330                 335

Ala Gly Met Arg Ala Asn Trp Tyr Gly Leu Leu Gly Lys Lys Phe Lys
            340                 345                 350

Asp Thr Phe Gly His Val Gly Gly Ser Ile Leu Gly Gly Phe Val Gly
        355                 360                 365

Met Lys Lys Pro Glu Asn Tyr Gly Val Pro Tyr Ser Leu Thr Glu Glu
    370                 375                 380

Phe Thr Ser Val Tyr Arg Met His Gln Leu Leu Pro Asp Lys Leu Gln
385                 390                 395                 400

Leu Arg Asn Ile Asp Ala Thr Pro Gly Pro Asn Lys Ser Leu Pro Leu
                405                 410                 415

Thr Asn Glu Ile Pro Leu Glu Asp Leu Ile Gly Gly Lys Gly Glu Lys
            420                 425                 430

Asn Leu Ser Lys Ile Gly Phe Thr Lys Gln Met Val Ser Met Gly His
        435                 440                 445

Gln Ala Cys Gly Ala Leu Glu Leu Trp Asn Tyr Pro Val Trp Met Arg
    450                 455                 460

Asp Leu Ile Pro Gln Asp Val Asp Gly Thr Asp Arg Pro Asp His Ile
465                 470                 475                 480

Asp Leu Ala Ala Leu Glu Ile Tyr Arg Asp Arg Glu Arg Ser Val Ala
                485                 490                 495

Arg Tyr Asn Glu Phe Arg Arg Gly Met Leu Gln Ile Pro Ile Ser Lys
            500                 505                 510

Trp Glu Asp Leu Thr Asp Asp Glu Glu Val Ile Asn Thr Leu Gly Glu
        515                 520                 525
```

Val Tyr Gly Asp Asp Val Glu Glu Leu Asp Leu Met Val Gly Met Ala
530 535 540

Ala Glu Lys Lys Ile Lys Gly Phe Ala Ile Ser Glu Thr Ala Phe Phe
545 550 555 560

Ile Phe Leu Val Met Ala Ser Arg Arg Leu Glu Ala Asp Arg Phe Phe
565 570 575

Thr Ser Asn Tyr Asn Glu Glu Thr Tyr Thr Lys Lys Gly Leu Glu Trp
580 585 590

Val Asn Thr Thr Glu Ser Leu Lys Asp Val Leu Asp Arg His Tyr Pro
595 600 605

Glu Ile Thr Glu Lys Trp Met Asn Ser Ser Ser Ala Phe Ser Val Trp
610 615 620

Asp Ser Thr Pro Gln Pro His Asn Pro Ile Pro Leu Tyr Phe Arg Val
625 630 635 640

Pro Pro Gln

<210> SEQ ID NO 49
<211> LENGTH: 644
<212> TYPE: PRT
<213> ORGANISM: Physcomitrella patens

<400> SEQUENCE: 49

Met Gly Gln Val Phe Gly Ala Leu Thr Ser Trp Met Val Leu Pro Asp
1 5 10 15

Leu Arg Pro Thr Tyr Arg Gln Met Ser Phe Val His Glu Thr Met Phe
20 25 30

Leu Val Val His Phe Ser Asp Arg Phe Trp Arg Trp Tyr Asn Thr Pro
35 40 45

Val Val Phe Gly Leu Leu Tyr Leu Glu Leu Arg Arg Thr Ile Gln Gln
50 55 60

Asn Tyr Asn Leu Ile Ala Val Gly Asn Ala Lys Asp Arg Asn Leu Gln
65 70 75 80

Val Pro Thr Pro Ser Arg Met Ala Val Val Asn Tyr Ile Asp Gln Pro
85 90 95

Gly Ser Ser Ser His Thr Thr Phe Asp Glu Glu Asp Tyr Ala Gly Phe
100 105 110

Phe Gly Arg Asn Met Gly Pro Gln Lys Ser Glu Leu Val Asn Pro His
115 120 125

Pro Ser Val Val Ala Ala Lys Leu Leu Ser Arg Thr Glu Leu Lys Asp
130 135 140

Tyr Gly Lys Gln Phe Asn Met Ile Ala Ala Ser Trp Ile Asn Phe Met
145 150 155 160

Ile His Asp Trp Val Asp His Leu Glu Glu Leu Ser Lys Glu Val Glu
165 170 175

Ile Thr Ala Pro Pro Ser Val Ser Ala Gln Cys Pro Leu Lys Asn Phe
180 185 190

Met Phe Tyr Pro Thr Lys Glu Val Pro Ala Gly Asn Asn Val Thr Gly
195 200 205

His Ile Asn Thr Arg Thr Pro Trp Trp Asp Ala Ser Val Ile Tyr Gly
210 215 220

Ser Thr Lys Glu Ala Glu Arg Asn Val Arg Thr Phe Arg Asp Gly Lys
225 230 235 240

Leu Lys Val Arg Pro Asp Gly Trp Leu Met Thr Asp Glu Asp Asn Leu
245 250 255

```
Pro Val Thr Gly Asp Ile Arg Asn Leu Trp Val Gly Val Ala Met Leu
            260                 265                 270

Gln Ser Leu Phe Ile Ala Glu His Asn Met Val Cys Asp Thr Ile Lys
        275                 280                 285

Lys Ala His Pro Asp Phe Asn Asp Glu Glu Leu Phe Gln His Ala Arg
    290                 295                 300

Val Val Thr Ala Ala Val Leu Ala Lys Ile His Thr Ile Asp Trp Thr
305                 310                 315                 320

Pro Gln Leu Leu Lys Asn Asn Val Leu Leu Ala Ala Met Arg Ala Asn
                325                 330                 335

Trp Tyr Gly Leu Leu Gly Lys Arg Phe Lys Asp Thr Phe Gly Thr Thr
            340                 345                 350

Pro Ile Ser Leu Leu Ser Gly Leu Val Gly Met Lys Lys Pro Val Asp
        355                 360                 365

His Gly Val Pro Tyr Ser Leu Thr Glu Glu Phe Thr Ala Val Tyr Arg
    370                 375                 380

Leu His Pro Leu Leu Pro Glu Lys Ile Asp Ile Lys Asn Ile Thr Ala
385                 390                 395                 400

Thr Ala Ser Ser Ser Leu His Thr Pro Pro Thr Val Asp Glu Ile Ala
                405                 410                 415

Val Pro Glu Leu Leu Gly Asn Lys Gly Asn Asp Lys Ala Leu Lys Leu
            420                 425                 430

Gly Leu Lys Thr Leu Leu Thr Ser Leu Gly His Gln Ser Ala Gly Ala
        435                 440                 445

Leu Gln Leu Phe Asn Tyr Pro Gln Trp Met Arg Glu Val Thr Ser Gln
    450                 455                 460

Asn Arg Asp Gly Thr Asp Arg Pro Asp Lys Val Asp Met Ala Ser Leu
465                 470                 475                 480

Glu Ile Tyr Arg Asp Arg Glu Arg Ser Val Ala Arg Tyr Asn Gln Phe
                485                 490                 495

Arg Arg Asn Leu Val Met Pro Thr Ile Gly Lys Trp Glu Asp Leu Thr
            500                 505                 510

Glu Asp Lys Gln Thr Leu Ala Ile Leu Arg Glu Leu Tyr Gly Asn Asn
        515                 520                 525

Val Glu Ser Leu Asp Leu Leu Val Gly Leu Leu Val Glu Lys Lys Pro
    530                 535                 540

Pro Gly Phe Ala Ile Ser Glu Thr Ala Phe Val Ile Phe Val Leu Met
545                 550                 555                 560

Ala Ser Arg Arg Leu Glu Ala Asp Pro Leu Phe Thr Ser His Phe Asn
                565                 570                 575

Glu Lys Val Tyr Thr Glu Glu Gly Leu Lys Trp Val Asn Thr Thr Glu
            580                 585                 590

Gly Leu Lys Asp Val Leu Arg Arg His His Pro Glu Leu Val Gly Asp
        595                 600                 605

Trp Met Thr Ala Ser Ser Ala Phe Ser Leu Trp Asn Gln Thr Pro Glu
    610                 615                 620

Lys Pro Ser Trp Ile Pro Leu Tyr Leu Arg Trp Gly Ala Asn Ser Pro
625                 630                 635                 640

Ala Ala Ser Ser
```

<210> SEQ ID NO 50
<211> LENGTH: 643
<212> TYPE: PRT
<213> ORGANISM: Pisum sativum

<400> SEQUENCE: 50

Met Trp Ser Ile Val Thr Asp Pro Ile Lys Asp Leu Ile Ser Lys Val
1               5                   10                  15

Val Lys Asn Ser Ile His Pro Asp Phe His Asp Ala Val Ser Lys Met
            20                  25                  30

Thr Ile Ile Asp Ala Phe Leu Phe Phe Ile Val His Ser Ile Asp Lys
        35                  40                  45

Leu Gly Ile Trp His Arg Leu Pro Val Phe Phe Gly Leu Leu Tyr Leu
    50                  55                  60

Ala Ile Arg Arg His Leu His Gln Glu Tyr Asn Leu Leu Asn Val Gly
65                  70                  75                  80

Thr Thr Pro Val Gly Ile Arg Ser Asn Pro Ser Asp Phe Pro Tyr Arg
                85                  90                  95

Thr Ala Asp Gly Arg Tyr Asn Asp Pro Phe Asn Asp Gly Ala Gly Ser
            100                 105                 110

Gln Gly Ser Phe Phe Gly Arg Asn Ile Leu Pro Val Asp Gln Lys Asn
        115                 120                 125

Lys Leu Leu Lys Pro Asp Pro Met Val Val Val Thr Lys Leu Leu Glu
    130                 135                 140

Arg Lys Thr Tyr Lys Asp Thr Gly Thr Gln Phe Asn Val Ile Ala Ala
145                 150                 155                 160

Ser Trp Ile Gln Phe Met Ile His Asp Trp Ile Asp His Met Glu Asp
                165                 170                 175

Thr Lys Gln Val Glu Leu Ser Ala Pro Ser Glu Val Ala Ser Gln Cys
            180                 185                 190

Pro Leu Lys Ser Phe Lys Phe Phe Lys Thr Lys Glu Ile Pro Thr Gly
        195                 200                 205

Phe Tyr Asp Ile Lys Thr Gly His Ala Asn Val Arg Thr Pro Trp Trp
    210                 215                 220

Asp Gly Ser Val Val Tyr Gly Ser Asn Glu Gln Val Leu Asn Lys Val
225                 230                 235                 240

Arg Thr Phe Lys Asp Gly Lys Leu Lys Ile Ser Lys Glu Gly His Leu
                245                 250                 255

Leu His Asn Glu Asp Gly Thr Ala Ile Ser Gly Asp Ile Arg Asn Ser
            260                 265                 270

Trp Ala Gly Val Thr Thr Leu Gln Thr Leu Phe Val Gln Glu His Asn
        275                 280                 285

Ala Val Cys Asp Ala Leu Lys Lys Glu Asn Ser Asp Leu Glu Asp Glu
    290                 295                 300

Asp Leu Tyr Arg His Ala Arg Leu Val Thr Ser Ala Val Ile Ala Lys
305                 310                 315                 320

Ile His Thr Ile Asp Trp Thr Val Glu Leu Leu Lys Thr Asp Thr Leu
                325                 330                 335

Leu Ala Gly Met Arg Ala Asn Trp Tyr Gly Leu Leu Gly Lys Gln Phe
            340                 345                 350

Lys Asp Arg Phe Gly His Val Gly Asn Ser Ile Leu Ser Gly Phe Val
        355                 360                 365

Gly Met Lys Arg Ser Glu Asn His Gly Val Pro Tyr Ser Leu Thr Glu
    370                 375                 380

Glu Phe Ala Thr Val Tyr Arg Met His Pro Leu Leu Pro Asp Ser Leu
385                 390                 395                 400

His Leu Arg Asp Ile Ser Ala Ser Pro Gly Pro Asn Lys Ser Pro Pro
405 410 415

Leu Ile Lys Glu Ile Pro Met Asn Asp Leu Ile Gly Leu Gln Gly Glu
420 425 430

Lys Thr Leu Leu Glu Ile Gly Asn Ala Lys Lys Leu Val Ser Met Gly
435 440 445

His Gln Ala Cys Gly Ala Leu Glu Leu Trp Asn Tyr Pro Ser Trp Leu
450 455 460

Arg Asn Leu Val Pro His Asn Ile Asp Gly Thr Glu Arg Ser Asp His
465 470 475 480

Val Asp Leu Ala Ala Leu Glu Val Tyr Arg Asp Arg Glu Arg Asn Val
485 490 495

Ala Arg Tyr Asn Gln Phe Arg Arg Gly Leu Leu Leu Ile Pro Ile Ser
500 505 510

Lys Trp Glu Asp Leu Thr Asp Asp Glu Glu Ala Ile Lys Val Leu Glu
515 520 525

Glu Val Tyr Gly Asp Asp Val Glu Glu Leu Asp Val Leu Val Gly Leu
530 535 540

Met Ala Glu Lys Lys Ile Lys Gly Phe Ala Ile Ser Glu Thr Ala Phe
545 550 555 560

Val Ile Phe Leu Leu Met Ala Ser Arg Arg Leu Glu Ala Asp Arg Phe
565 570 575

Phe Thr Ser Asn Phe Asn Glu Glu Thr Tyr Thr Lys Lys Gly Leu Glu
580 585 590

Trp Val Asn Thr Thr Glu Ser Leu Lys Asp Val Ile Asp Arg His His
595 600 605

Pro Glu Met Thr His Lys Trp Leu Asn Ser Ser Ser Ala Phe Ser Val
610 615 620

Trp Asp Thr Ser Pro Asn Lys His Asn His Ile Pro Ile Tyr Phe Arg
625 630 635 640

Val Pro Asn

<210> SEQ ID NO 51
<211> LENGTH: 632
<212> TYPE: PRT
<213> ORGANISM: Solanum lycopersicum

<400> SEQUENCE: 51

Met Ala Phe Ser Ile Ser Leu Pro Asp Phe Val His Pro Gln Leu Arg
1 5 10 15

His Val Val Ala Lys Met Ser Phe Phe Asp Thr Ile Leu Phe Tyr Val
20 25 30

Val His Leu Val Asp Lys Phe Asp Leu Trp His Arg Leu Pro Val Leu
35 40 45

Leu Gly Ala Ala Tyr Leu Gly Ile Arg Arg His Leu His Gln Arg Tyr
50 55 60

Asn Leu Leu His Val Gly Lys Val Asn Gly Lys Lys Tyr Asp Thr Glu
65 70 75 80

Glu Phe Thr Tyr Arg Thr Ala Asp Gly Ser Cys Asn His Pro Val Asp
85 90 95

His Leu Val Gly Ser Gln Gly Thr Phe Phe Gly Arg Asn Met Leu Pro
100 105 110

Ser Thr Ser Ser Tyr Ala Leu Leu Glu Pro His Pro Val Thr Val Ala
115 120 125

```
Ser Lys Leu Leu Glu Arg Arg Lys Tyr Thr Asp Cys Gly Gly Gln Phe
    130                 135                 140

Asn Met Ile Ala Cys Ala Trp Leu Gln Phe Met Ile His Asp Trp Asn
145                 150                 155                 160

Asp His Met Glu Asp Thr Glu Gln Val Glu Leu Arg Ala Pro Gln Asp
                165                 170                 175

Val Ala Ala Gly Cys Pro Leu Lys Ser Phe Lys Phe Leu Lys Thr Lys
            180                 185                 190

Lys Leu Pro Thr Gly Ser Pro Asp Leu Lys Phe Gly His Leu Asn Ser
        195                 200                 205

Arg Thr Pro Trp Trp Asp Gly Ser Val Ile Tyr Gly Asn Asn Glu Glu
    210                 215                 220

Gly Met Ile Arg Val Arg Arg Phe Lys Asp Gly Lys Leu Arg Leu Ser
225                 230                 235                 240

Gly Asp Gly Leu Leu Glu His Asp Asp Lys Gly Ile Pro Ile Ser Gly
                245                 250                 255

Asp Val Arg Asn Tyr Trp Ala Gly Tyr Ser Leu Leu Gln Ala Leu Phe
            260                 265                 270

Val Lys Glu His Asn Ala Ile Cys Asp Met Leu Lys Glu His Tyr Pro
        275                 280                 285

Glu Phe Asp Asp Glu Lys Val Tyr Arg His Ala Arg Leu Ile Thr Ser
    290                 295                 300

Ala Val Ile Ala Lys Ile His Thr Ile Asp Trp Thr Leu Glu Ile Val
305                 310                 315                 320

Lys Thr Asp Thr Leu Met Ala Gly Met Arg Ile Asn Trp Tyr Gly Leu
                325                 330                 335

Leu Gly Lys Arg Val Lys Asp Leu Leu Gly Pro Lys Phe Gly Pro Val
            340                 345                 350

Leu Ser Gly Leu Val Gly Leu Lys Lys Pro Arg Asp His Gly Thr Pro
        355                 360                 365

Tyr Ser Leu Thr Glu Glu Phe Val Ser Val Tyr Arg Met His Ser Leu
    370                 375                 380

Leu Pro Asp Thr Ile Val Leu Arg Asp Leu Lys Ser Thr Thr Ser Glu
385                 390                 395                 400

Asp Lys Ser Leu Pro Ile Gln Asp Glu Ile Pro Met Arg Glu Met Ile
                405                 410                 415

Gly Lys Glu Gly Glu Lys Asn Leu Ser Lys Ile Gly Met Glu Gln Met
            420                 425                 430

Leu Val Ser Met Gly His Gln Ser Ser Gly Ala Gly Thr Leu Trp Asn
        435                 440                 445

Phe Pro Ser Trp Met Arg Asn Leu Val Pro His Asp Ile Asp Gly Asp
    450                 455                 460

Asp Arg Pro Asp Ser Ile Asp Met Ala Ala Leu Asp Ile Tyr Arg Asp
465                 470                 475                 480

Arg Glu Arg Gly Val Pro Arg Tyr Asn Glu Phe Arg Arg Asn Leu Leu
                485                 490                 495

Met Val Pro Ile Ser Lys Trp Glu Asp Leu Thr Asn Asp Glu Glu Val
            500                 505                 510

Ile Glu Ala Leu Gln Glu Val Tyr Gly Asp Asp Ile Glu Lys Leu Asp
        515                 520                 525

Leu Gln Ile Gly Leu His Ala Glu Lys Lys Ile Lys Gly Phe Ala Ile
    530                 535                 540
```

Ser Glu Thr Ala Phe Phe Ile Phe Leu Leu Ile Ala Ser Arg Arg Leu
545 550 555 560

Glu Ala Asp Arg Phe Phe Thr Thr Asp Phe Asn Ser Arg Thr Tyr Thr
565 570 575

Glu Lys Gly Phe Glu Trp Val Asn Lys Thr Glu Thr Leu Lys Asp Val
580 585 590

Ile Asp Arg Tyr Phe Pro Glu Met Thr Glu Lys Tyr Met Arg Cys Thr
595 600 605

Ser Ala Phe Ser Val Trp Ser Ser Asp Pro Asp Pro Lys His Tyr Leu
610 615 620

Pro Leu Tyr Leu Arg Pro Ala Thr
625 630

<210> SEQ ID NO 52
<211> LENGTH: 639
<212> TYPE: PRT
<213> ORGANISM: Solanum tuberosum

<400> SEQUENCE: 52

Met Ser Phe Val Met Leu Lys Asn Leu Leu Leu Ser Pro Leu Arg Lys
1 5 10 15

Phe Ile His Lys Asp Phe His Glu Ile Phe Glu Lys Met Thr Leu Ile
20 25 30

Asp Lys Leu Phe Phe Leu Ile Val His Phe Ile Asp Lys Tyr Asn Phe
35 40 45

Trp His Arg Leu Pro Val Phe Phe Gly Leu Leu Tyr Leu Gly Ala Arg
50 55 60

Arg Thr Leu His Gln Gln Tyr Asn Leu Ile Asn Val Gly Arg Thr Pro
65 70 75 80

Thr Gly Val Arg Ser Asn Pro Ala Asp Tyr Pro Tyr Arg Thr Ala Asp
85 90 95

Gly Lys Phe Asn Asp Pro Phe Asn Glu Gly Ala Gly Ser Gln Phe Ser
100 105 110

Phe Phe Gly Arg Asn Met Met Pro Val His Gln Asp Asn Lys Leu Lys
115 120 125

Lys Pro Asp Pro Met Val Val Ala Thr Lys Leu Leu Ala Arg Lys Lys
130 135 140

Phe Ile Asp Thr Gly Lys Gln Phe Asn Met Ile Ala Ala Ser Trp Ile
145 150 155 160

Gln Phe Met Val His Asp Trp Ile Asp His Leu Glu Asp Thr Gln Gln
165 170 175

Val Glu Leu Arg Ala Pro Lys Glu Val Ala Asn Glu Cys Pro Leu Lys
180 185 190

Ser Phe Arg Phe Asn Lys Ser Lys Glu Thr Pro Thr Asp Phe Tyr Glu
195 200 205

Ile Lys Lys Gly His Leu Asn Ile Arg Thr Pro Trp Trp Asp Gly Ser
210 215 220

Val Ile Tyr Gly Ser Asn Glu Asp Val Leu Lys Lys Val Arg Thr Phe
225 230 235 240

Lys Asp Gly Lys Leu Lys Leu Ser Glu Asn Gly Leu Ile Gln Gln Asp
245 250 255

Glu Asn Gly Lys Ile Ile Ser Gly Asp Val Arg Asn Thr Trp Ala Gly
260 265 270

Leu Leu Thr Leu Gln Ala Leu Phe Val Gln Glu His Asn Ala Val Cys
275 280 285

```
Asp Thr Leu Lys Lys Glu Tyr Pro Glu Leu Lys Asp Glu Glu Leu Tyr
    290                 295                 300

Arg His Ala Arg Leu Val Thr Ser Ala Val Ile Ala Lys Val His Thr
305                 310                 315                 320

Ile Asp Trp Thr Val Gln Leu Leu Lys Thr Asp Thr Leu Leu Ala Gly
                325                 330                 335

Met Arg Ala Asn Trp Tyr Gly Leu Leu Gly Lys Lys Phe Lys Asp Thr
            340                 345                 350

Phe Gly His Val Gly Ser Ile Leu Ser Gly Val Val Gly Met Lys Lys
        355                 360                 365

Pro Glu Asn His Gly Val Pro Tyr Ser Leu Thr Glu Glu Phe Val Cys
    370                 375                 380

Val Tyr Arg Met His Gln Leu Leu Pro Asp Thr Leu Gln Leu Arg Asn
385                 390                 395                 400

Ile Asp Ala Thr Pro Gly Pro Asn Lys Ser Leu Pro Leu Thr Asn Glu
                405                 410                 415

Ile Pro Met Glu Glu Val Val Gly Ser Lys Gly Lys Glu Asn Leu Ser
            420                 425                 430

Arg Ile Gly Phe Thr Lys Gln Met Val Ser Met Gly His Gln Ala Ser
        435                 440                 445

Gly Ala Leu Glu Leu Trp Asn Tyr Pro Val Trp Met Arg Asp Leu Ile
    450                 455                 460

Ala Gln Asp Val Asp Gly Thr Asp Arg Pro His His Ile Asp Leu Ala
465                 470                 475                 480

Ala Leu Glu Ile Tyr Arg Asp Arg Glu Arg Ser Val Ala Arg Tyr Asn
                485                 490                 495

Asp Phe Arg Arg Gly Met Leu Gln Ile Pro Ile Ser Lys Trp Glu Asp
            500                 505                 510

Leu Thr Asp Asp Glu Glu Ala Ile Lys Thr Leu Arg Glu Val Tyr Asp
        515                 520                 525

Asp Asp Ile Glu Glu Leu Asp Leu Leu Val Gly Leu Met Ala Glu Lys
    530                 535                 540

Lys Ile Lys Gly Phe Ala Ile Ser Glu Thr Ala Phe Asn Ile Phe Leu
545                 550                 555                 560

Leu Met Ala Ile Arg Arg Leu Glu Ala Asp Arg Phe Phe Thr Ser Asn
                565                 570                 575

Tyr Asn Glu Glu Thr Tyr Thr Lys Lys Gly Leu Glu Trp Val Asn Thr
            580                 585                 590

Thr Glu Gly Leu Lys Asp Val Leu Asp Arg His Tyr Pro Glu Met Thr
        595                 600                 605

Glu Lys Trp Met Asn Ser Asn Ser Ala Phe Ser Val Trp Asp Ser Ser
    610                 615                 620

Pro Glu Pro His Asn Pro Ile Pro Leu Tyr Phe Arg Val Pro Gln
625                 630                 635
```

<210> SEQ ID NO 53
<211> LENGTH: 638
<212> TYPE: PRT
<213> ORGANISM: Solanum tuberosum

<400> SEQUENCE: 53

```
Met Ser Phe Leu Glu Asn Leu Leu Leu Ser His Leu Leu Asn Phe Ile
1               5                   10                  15
```

```
His Arg Asp Phe His Glu Val Phe Glu Glu Met Thr Leu Ile Asn Lys
            20                  25                  30

Phe Leu Phe Leu Met Val His Phe Val Asp Lys Leu Asn Phe Trp His
        35                  40                  45

Arg Leu Pro Val Phe Leu Gly Leu Ala Tyr Leu Gly Ala Arg Arg Arg
    50                  55                  60

Leu His Gln Gln Tyr Asn Leu Ile Asn Val Gly Thr Thr His Thr Gly
65                  70                  75                  80

Asn Ser Gly Asp Tyr Pro Tyr Arg Thr Ala Asp Gly Lys Tyr Asn Asp
                85                  90                  95

Pro Phe Asn Glu Asn Ala Gly Ser Glu Phe Ser Phe Phe Gly Arg Asn
            100                 105                 110

Met Met Pro Val His Gln Leu Asn Lys Leu Lys Lys Pro Asp Pro Met
        115                 120                 125

Val Val Ala Thr Lys Leu Leu Ala Arg Arg Lys Phe Ile Asp Thr Gly
    130                 135                 140

Lys Gln Leu Asn Ile Ile Ala Ala Ser Trp Ile Gln Phe Met Ile His
145                 150                 155                 160

Asp Trp Ile Asp His Met Glu Asp Thr Asn Gln Met Lys Leu Asp Ala
                165                 170                 175

Pro Lys Asp Val Ala Ser Gln Cys Pro Leu Lys Ser Phe Lys Phe Tyr
            180                 185                 190

Lys Ser Thr Glu Thr Pro Thr Gly Leu Asp Glu Ile Lys Thr Gly His
        195                 200                 205

Leu Asn Arg Arg Thr Pro Trp Trp Asp Gly Ser Ala Ile Tyr Gly Asn
    210                 215                 220

Asn Ala Asp Asp Leu Lys Lys Val Arg Thr Phe Ile Asp Gly Lys Leu
225                 230                 235                 240

Lys Leu Ser Glu Asn Gly Leu Ile Gln Gln Asp Glu Asn Gly Lys Ile
                245                 250                 255

Ile Ser Gly Asp Val Arg Asn Thr Trp Ala Gly Leu Leu Thr Leu Tyr
            260                 265                 270

Ala Leu Phe Val Gln Glu His Asn Ala Val Cys Asp Ala Leu Lys Lys
        275                 280                 285

Glu Tyr Pro Glu Leu Lys Asp Glu Asp Leu Tyr Arg His Ala Arg Leu
    290                 295                 300

Val Thr Ser Ala Val Ile Ala Lys Val His Thr Ile Asp Trp Thr Val
305                 310                 315                 320

Glu Leu Leu Lys Thr Asp Thr Leu Leu Ala Gly Met Arg Ile Ser Trp
                325                 330                 335

Tyr Gly Leu Leu Gly Lys Lys Phe Lys Asp Thr Phe Gly His Ile Gly
            340                 345                 350

Gly Asp Phe Trp Leu Ser Gly Phe Val Gly Met Lys Lys Pro Arg Asn
        355                 360                 365

His Gly Val Pro Tyr Ser Leu Thr Glu Glu Phe Ser Ser Val Tyr Arg
    370                 375                 380

Leu His Gln Leu Val Pro Asp Thr Leu Gln Leu Arg Asn Ile Asp Ala
385                 390                 395                 400

Thr Pro Ala Pro Asn Lys Ser Leu Pro Leu Ile Asn Glu Ile Pro Met
                405                 410                 415

Glu Asp Leu Ile Gly Gly Lys Gly Ala Glu Lys Leu Ser Lys Ile Gly
            420                 425                 430
```

```
Phe Leu Asn Gln Met Val Ser Met Gly His Gln Ser Cys Gly Ala Leu
        435                 440                 445

Glu Leu Trp Asn Tyr Pro Val Trp Met Arg Asp Leu Val Ala Gln Asp
    450                 455                 460

Val Asp Gly Thr Asp Arg Pro Asp His Val Asp Leu Pro Ala Leu Glu
465                 470                 475                 480

Ile Tyr Arg Asp Arg Glu Arg Ser Val Ala Arg Tyr Asn Glu Phe Arg
                485                 490                 495

Arg Arg Ile Phe Gln Ile Pro Ile Thr Lys Trp Glu Asp Leu Ser Asp
            500                 505                 510

Asp Lys Glu Val Ile Glu Thr Leu Val Glu Val Tyr Gly Asp Asn Asn
        515                 520                 525

Val Glu Glu Leu Asp Leu Leu Val Gly Ile Met Ala Glu Lys Lys Ile
    530                 535                 540

Lys Gly Phe Val Ile Ser Glu Thr Ala Phe Phe Ile Phe Leu Phe Met
545                 550                 555                 560

Ala Gly Arg Arg Leu Glu Gly Asp Arg Phe Phe Thr Ser Asn Tyr Asn
                565                 570                 575

Glu Glu Thr Tyr Thr Lys Arg Gly Leu Glu Trp Val Asn Thr Thr Glu
            580                 585                 590

Ser Leu Lys Asp Val Leu Asp Arg His Tyr Pro Lys Met Thr Glu Lys
        595                 600                 605

Trp Met Asn Ser Ser Ser Ala Phe Ser Val Trp Asp Ser Ser Pro Gln
    610                 615                 620

Pro Tyr Asn Pro Ile Pro Leu Tyr Leu Arg Leu Pro His Lys
625                 630                 635


<210> SEQ ID NO 54
<211> LENGTH: 633
<212> TYPE: PRT
<213> ORGANISM: Solanum tuberosum

<400> SEQUENCE: 54

Met Ser Phe Val Asn Leu Leu Leu Phe Pro Leu Arg Cys Phe Ile His
1               5                   10                  15

Lys Asp Phe His Asp Val Val Asp Arg Met Ser Leu Leu Asn Lys Leu
            20                  25                  30

Leu Phe Met Met Val His Leu Val Asp Lys Leu Asn Leu Trp His Arg
        35                  40                  45

Leu Pro Val Phe Leu Gly Leu Leu Tyr Leu Ala Ala Arg Arg His Leu
    50                  55                  60

His Gln Glu Tyr Asn Leu Ile Asn Val Gly Val Gly Arg Lys Pro Ile
65                  70                  75                  80

Asp Val Thr Ser Asn Arg Ala Val Gly Lys Tyr Asn Asp Pro Phe Asn
                85                  90                  95

Glu Gly Gly Gly Ser Glu Phe Pro Phe Phe Gly Arg Asn Met Met Pro
            100                 105                 110

Val Asp Gln His Glu Lys Leu Lys Asn Pro Asp Pro Met Val Val Ala
        115                 120                 125

Thr Lys Leu Leu Ala Arg Arg Lys Phe Ile Asp Thr Gly Lys Gln Phe
    130                 135                 140

Asn Met Ile Ala Ala Ser Trp Ile Gln Phe Met Ile His Asp Trp Ile
145                 150                 155                 160

Asp His Leu Glu Asp Thr Gln Gln Ile Glu Leu Arg Ala Pro Glu Glu
                165                 170                 175
```

```
Val Ala Ser Glu Cys Pro Leu Lys Ser Phe Lys Phe Phe Lys Thr Lys
            180                 185                 190

Gln Thr Pro Thr Gly Leu Cys Asp Ile Gln Thr Gly His Leu Asn Ile
        195                 200                 205

Arg Thr Pro Gln Trp Asp Gly Ser Ala Ile Tyr Gly Asn Asn Ala Glu
    210                 215                 220

Val Ser Lys Lys Val Arg Thr Phe Lys Asp Gly Lys Leu Lys Leu Ser
225                 230                 235                 240

Glu Asn Gly Leu Leu Glu Gln Asp Glu Asn Gly Lys Ile Ile Ser Gly
                245                 250                 255

Asp Val Arg Asn Asn Trp Ala Gly Leu Leu Ser Leu Gln Ala Leu Phe
            260                 265                 270

Val Gln Glu His Asn Leu Val Cys Asp Thr Leu Lys Lys Glu Tyr Pro
        275                 280                 285

Glu Leu Lys Asp Glu Asp Leu Tyr Arg His Ala Lys Leu Val Thr Ser
    290                 295                 300

Ala Val Ile Ala Lys Ile His Thr Ile Asp Trp Thr Val Glu Leu Leu
305                 310                 315                 320

Asn Thr Asp Thr Leu Leu Ala Gly Met Arg Ala Asn Trp Tyr Gly Leu
                325                 330                 335

Leu Gly Lys Lys Phe Lys Asp Thr Phe Gly His Val Gly Gly Ser Ile
            340                 345                 350

Leu Gly Gly Phe Val Gly Met Lys Lys Pro Glu Asp His Gly Val Pro
        355                 360                 365

Tyr Ser Leu Thr Glu Glu Phe Thr Ser Val Tyr Arg Met His Gln Leu
    370                 375                 380

Leu Pro Asp Thr Leu Gln Leu Arg Asn Ile Asp Ala Thr Pro Gly Leu
385                 390                 395                 400

Asn Lys Ser Leu Pro Leu Thr Asn Glu Ile Leu Met Glu Asp Leu Ile
                405                 410                 415

Gly Gly Lys Gly Lys Glu Asn Leu Ser Arg Ile Gly Phe Thr Lys Gln
            420                 425                 430

Met Val Ser Met Gly His Gln Ala Ser Gly Ala Leu Glu Leu Trp Asn
        435                 440                 445

Tyr Pro Ile Trp Met Arg Asp Leu Ile Ala Gln Asp Val Asp Gly Thr
    450                 455                 460

Asp Arg Pro His His Ile Asp Leu Ala Ala Leu Glu Ile Tyr Arg Asp
465                 470                 475                 480

Arg Glu Arg Ser Val Ala Arg Tyr Asn Glu Phe Arg Arg Arg Met Leu
                485                 490                 495

Gln Ile Pro Ile Ser Lys Trp Glu Asp Leu Thr Asp Asp Glu Glu Val
            500                 505                 510

Ile Lys Thr Leu His Glu Val Tyr Gly Asp Glu Val Glu Gln Leu Asp
        515                 520                 525

Leu Leu Val Gly Met Ser Ala Glu Lys Lys Ile Lys Gly Phe Ala Ile
    530                 535                 540

Ser Glu Thr Ala Phe Ile Ile Phe Leu Ile Met Ala Ser Arg Arg Leu
545                 550                 555                 560

Glu Ala Asp Lys Phe Phe Thr Ser Tyr Tyr Asn Asp Glu Thr Tyr Thr
                565                 570                 575

Lys Lys Gly Leu Glu Trp Val Asn Thr Thr Glu Ser Leu Lys Asp Val
            580                 585                 590
```

Leu Asp Arg His Tyr Pro Glu Met Thr Glu Lys Trp Met Asn Ser Asn
595 600 605

Ser Ala Phe Ser Val Trp Asp Ser Ser Pro Glu Pro His Asn Pro Ile
610 615 620

Pro Leu Tyr Phe Arg Val Pro Arg Thr
625 630

<210> SEQ ID NO 55
<211> LENGTH: 642
<212> TYPE: PRT
<213> ORGANISM: Solanum tuberosum

<400> SEQUENCE: 55

Met Thr Met Ile Met Leu Lys Asn Leu Leu Phe Ser Pro Leu Arg Gly
1 5 10 15

Phe Ile His Lys Asp Phe His Gln Ile Leu Asp Lys Met Asn Leu Arg
20 25 30

Asp Lys Leu Ser Phe Leu Ile Val His Ile Val Asp Lys His Asn Leu
35 40 45

Trp His Arg Val Pro Val Phe Leu Gly Leu Val Tyr Leu Ala Leu Arg
50 55 60

Arg His Leu Asn Gln Glu Tyr Asn Leu Ile Asn Val Gly Arg Thr Pro
65 70 75 80

Thr Gly Val Arg Ser Asn Pro Gly Asp Phe Pro Tyr Arg Thr Ala Asp
85 90 95

Gly Lys Tyr Asn Asp Pro Phe Asn Glu Gly Ala Gly Ser Glu Phe Ser
100 105 110

Phe Phe Gly Arg Asn Met Met Pro Val Asp Gln His Asp Lys Leu Lys
115 120 125

Asn Pro Asp Pro Met Val Val Ala Thr Lys Leu Leu Ala Arg Arg Lys
130 135 140

Phe Ile Asp Thr Gly Lys Gln Phe Asn Met Ile Ala Ala Ser Trp Ile
145 150 155 160

Gln Phe Met Ile His Asp Trp Ile Asp His Leu Glu Asp Thr Gln Gln
165 170 175

Ile Glu Glu Leu Arg Ala Pro Glu Glu Val Ala Ser Gln Cys Pro Leu
180 185 190

Lys Ser Phe Lys Phe Tyr Lys Ser Lys Glu Thr Pro Thr Gly Phe Tyr
195 200 205

Glu Ile Lys Thr Gly Tyr Leu Asn Arg Arg Thr Pro Trp Trp Asp Gly
210 215 220

Ser Ala Ile Tyr Gly Ser Asp Val Glu Ile Leu Lys Lys Val Arg Thr
225 230 235 240

Phe Lys Asp Gly Lys Leu Lys Leu Ser Glu Asn Gly Leu Leu Glu Gln
245 250 255

Asp Glu Asn Gly Lys Ile Ile Ser Gly Asp Val Arg Asn Thr Trp Ala
260 265 270

Gly Leu Leu Ser Leu Gln Ala Leu Phe Val Gln Glu His Asn Leu Val
275 280 285

Cys Asp Ala Leu Lys Lys Glu Tyr Pro Glu Leu Glu Asp Glu Val Leu
290 295 300

Tyr Arg His Ala Arg Leu Val Thr Ser Ala Val Ile Ala Lys Val His
305 310 315 320

Thr Ile Asp Trp Thr Val Glu Leu Leu Lys Thr Asp Thr Leu Leu Ala
325 330 335

```
Ala Met Arg Ala Asn Trp Tyr Gly Leu Leu Gly Lys Lys Phe Lys Asp
            340                 345                 350

Thr Phe Gly His Val Gly Gly Ala Ile Leu Gly Gly Leu Val Gly Met
        355                 360                 365

Lys Lys Pro Glu Asn His Gly Val Pro Tyr Ser Leu Thr Glu Glu Phe
    370                 375                 380

Val Ser Val Tyr Arg Met His Gln Leu Leu Pro Asp Lys Leu Gln Leu
385                 390                 395                 400

Arg Asn Ile Asp Thr Thr Ser Gly Pro Asn Lys Ser Leu Pro Leu Thr
            405                 410                 415

Asn Glu Ile Pro Met Glu Asp Leu Ile Gly Gly Lys Gly Ala Lys Asn
            420                 425                 430

Leu Ser Lys Ile Gly Phe Ile Thr Gln Met Val Ser Met Gly His Gln
        435                 440                 445

Ala Cys Gly Ala Leu Glu Leu Trp Asn Tyr Pro Val Trp Met Arg Asp
    450                 455                 460

Leu Val Ala Gln Asp Val Asp Gly Thr Asp Arg Pro Asp His Val Asp
465                 470                 475                 480

Leu Pro Ala Leu Glu Ile Tyr Arg Asp Arg Glu Arg Ser Val Ala Arg
            485                 490                 495

Tyr Asn Glu Phe Arg Arg Arg Met Leu Gln Ile Pro Ile Thr Lys Trp
            500                 505                 510

Glu Asp Leu Thr Asp Asp Glu Glu Val Ile Lys Thr Leu Asp Glu Val
        515                 520                 525

Tyr Gly Asp Asp Val Glu Gln Leu Asp Leu Leu Val Gly Met Ser Ala
    530                 535                 540

Glu Lys Lys Ile Lys Gly Phe Ala Ile Ser Glu Thr Ala Phe Phe Ile
545                 550                 555                 560

Phe Leu Leu Met Ala Ser Arg Arg Leu Glu Ala Asp Arg Phe Phe Thr
            565                 570                 575

Ser Asn Tyr Asn Glu Glu Thr Tyr Thr Lys Lys Gly Leu Glu Trp Val
            580                 585                 590

Asn Thr Thr Glu Ser Leu Lys Asp Val Leu Asp Arg His Tyr Pro Glu
        595                 600                 605

Met Thr Asp Lys Trp Met Asn Ser Asn Ser Ala Phe Ser Val Trp Asp
    610                 615                 620

Ser Ser Pro Gln Pro His Asn Pro Leu Pro Leu Tyr Phe Arg Val Pro
625                 630                 635                 640

Lys His


<210> SEQ ID NO 56
<211> LENGTH: 632
<212> TYPE: PRT
<213> ORGANISM: Solanum tuberosum

<400> SEQUENCE: 56

Met Ala Phe Ser Ile Ser Leu Pro Asp Phe Val His Pro Gln Leu Arg
1               5                   10                  15

His Val Val Ala Lys Met Ser Leu Phe Asp Thr Ile Leu Phe Tyr Val
            20                  25                  30

Val His Leu Val Asp Lys Phe Asp Leu Trp His Arg Leu Pro Val Leu
        35                  40                  45

Leu Gly Ala Ala Tyr Leu Gly Ile Arg Arg His Leu His Gln Arg Tyr
    50                  55                  60
```

```
Asn Leu Leu His Val Gly Lys Val Asn Gly Lys Lys Tyr Asp Thr Lys
65                  70                  75                  80

Glu Phe Thr Tyr Arg Thr Ala Asp Gly Thr Cys Asn His Pro Val Asp
                85                  90                  95

His Leu Val Gly Ser Gln Gly Thr Phe Phe Gly Arg Asn Met Leu Pro
            100                 105                 110

Ser Thr Ser Ser Tyr Ala Leu Leu Glu Pro His Pro Val Thr Val Ala
        115                 120                 125

Thr Lys Leu Leu Glu Arg Arg Lys Tyr Thr Asp Cys Gly Gly Gln Phe
    130                 135                 140

Asn Met Ile Ala Cys Ala Trp Val Gln Phe Met Ile His Asp Trp Asn
145                 150                 155                 160

Asp His Met Glu Asp Thr Glu Gln Val Glu Leu Arg Ala Pro Gln Asp
                165                 170                 175

Val Ala Ala Gly Cys Pro Leu Lys Ser Phe Lys Phe Leu Lys Thr Lys
            180                 185                 190

Lys Leu Pro Thr Gly Ser Pro Asp Leu Lys Phe Gly His Leu Asn Ser
        195                 200                 205

Arg Thr Pro Trp Trp Asp Gly Ser Val Ile Tyr Gly Asn Asn Glu Glu
    210                 215                 220

Gly Met Ile Arg Val Arg Arg Phe Lys Glu Gly Lys Leu Arg Val Ser
225                 230                 235                 240

Gly Asp Gly Leu Leu Glu His Asp Asp Lys Gly Ile Pro Ile Ser Gly
                245                 250                 255

Asp Val Arg Asn Tyr Trp Ala Gly Tyr Ser Leu Leu Gln Ala Leu Phe
            260                 265                 270

Val Lys Glu His Asn Ala Ile Cys Asp Met Leu Lys Glu His Tyr Pro
        275                 280                 285

Glu Phe Asp Asp Glu Lys Val Tyr Arg His Ala Arg Leu Ile Thr Ser
    290                 295                 300

Ala Val Ile Ala Lys Ile His Thr Ile Asp Trp Thr Leu Glu Leu Val
305                 310                 315                 320

Lys Thr Asp Thr Leu Met Ala Gly Met Arg Ile Asn Trp Tyr Gly Leu
                325                 330                 335

Leu Gly Lys Lys Val Lys Asp Leu Leu Gly Pro Lys Phe Gly Pro Val
            340                 345                 350

Leu Ser Gly Leu Val Gly Leu Lys Lys Pro Arg Asp His Gly Thr Pro
        355                 360                 365

Tyr Ser Leu Thr Glu Glu Phe Val Ser Val Tyr Arg Met His Ser Leu
    370                 375                 380

Leu Pro Asp Thr Ile Val Leu Arg Asp Leu Lys Ser Thr Thr Ser Glu
385                 390                 395                 400

Asp Lys Ser Leu Pro Ile Gln Asp Glu Ile Pro Met Arg Glu Met Ile
                405                 410                 415

Gly Lys Glu Gly Glu Lys Asn Leu Ser Lys Ile Gly Met Glu Gln Met
            420                 425                 430

Leu Val Ser Met Gly His Gln Ser Cys Gly Ala Ala Thr Leu Trp Asn
        435                 440                 445

Phe Pro Ser Trp Met Arg Asn Leu Val Pro His Asp Ile Asp Gly Asp
    450                 455                 460

Asp Arg Leu Asp Leu Ile Asp Met Ala Ala Leu Asp Ile Tyr Arg Asp
465                 470                 475                 480
```

```
Arg Glu Arg Gly Ile Pro Arg Tyr Asn Glu Phe Arg Arg Asn Leu Leu
                485                 490                 495

Met Val Pro Ile Ser Lys Trp Glu Asp Leu Thr Asp Asp Glu Glu Val
            500                 505                 510

Ile Glu Ala Leu Gln Glu Val Tyr Gly Asp Asp Ile Glu Lys Leu Asp
        515                 520                 525

Leu Gln Val Gly Leu His Ala Glu Lys Lys Ile Lys Gly Phe Ala Ile
    530                 535                 540

Ser Glu Thr Ala Phe Phe Ile Phe Leu Leu Ile Ala Ser Arg Arg Leu
545                 550                 555                 560

Glu Ala Asp Arg Phe Phe Thr Thr Asp Phe Asn Ser Arg Thr Tyr Thr
                565                 570                 575

Glu Lys Gly Phe Glu Trp Val Asn Lys Thr Glu Thr Leu Lys Asp Val
            580                 585                 590

Ile Asp Arg Ser Phe Pro Glu Thr Thr Glu Lys Tyr Met Arg Cys Thr
        595                 600                 605

Ser Ala Phe Ser Val Trp Ser Ser Asp Pro Asp Pro Lys His Tyr Leu
    610                 615                 620

Pro Leu Tyr Leu Arg Pro Ala Thr
625                 630


<210> SEQ ID NO 57
<211> LENGTH: 1512
<212> TYPE: DNA
<213> ORGANISM: Acinetobacter sp. strain M1

<400> SEQUENCE: 57

atgcattacg ttgatccgaa tcagagcggt agcaaaattc attttaaaga tcagtacgag      60

aacttcattg gtggccagtg ggttgcaccg gtgaaaggtg tttattttga taatattagc     120

ccggttgatg gcaaaagttt tacccgtatt ccgcgcagca gtgcagaaga tattgaactg     180

gccctggatg ccgcccataa agcaaaaaag gaatggaata agagcagtcc gaccacccgt     240

agtaatctgc tgctgaaaat tgccgataga atggaagcca atctggaaat gctggccgtt     300

gcagaaacct gggataatgg taaaccggtg cgcgaaaccc tggcagcaga tattccgctg     360

gccattgatc attttcgcta ttttgccggc tgtattcgtg cccaggaagg cggcattagt     420

gaaattgatg aagataccat tgcatatcat ttccatgaac cgctgggtgt tgttggccag     480

attattccgt ggaattttcc gattctgatg gccgcatgga aactggcacc ggccctggca     540

gccggtaatt gcgtggttat taagccggcc gaacagaccc cggttggtat tctgctggtt     600

gccgaactga ttcaggatct gctgccggca ggcgtgctga atattgtgaa tggttatggt     660

gcagaagttg gccgcccgct ggcaaccagt ccgcgtattg caaaaattgc attcactggt     720

agtacccagg ttggtcagct gattatgcag tatgccaccg aaaatattat tccggtgacc     780

ctggaactgg gtggtaaaag cccgaatgtt ttctttgccg atgttatgga tcatgatgat     840

gattttctgg ataaaaccct ggaaggtttt gccatgtttg ccctgaatca gggcgaagtt     900

tgcacctgcc cgagtcgtgc actgattcag gaaagtattg cagatcagtt tatggaaaaa     960

gcaattgaac gtgttaagcg tattaagctg ggccatccgc tggataccga taccatggtg    1020

ggtgcacagg ccagcctgga acagcaggaa aaaattctgc gctgtattga taccggccgc    1080

caggaaggcg ccgaagttct gctgggtggc catggtcgtc aggaagttgg caatggttat    1140

tatattgaac cgaccatttt caaaggtcat aataatatgc aggtgtttca ggaagaaatt    1200

tttggcccgg ttctgagcgt taccaccttt aaagattttg atgaagccat tcagatcgca    1260
```

aatgatacca tgtatggcct gggtgcaggc gtttggagcc gcagtaccca taccgcctat 1320
cgtgccggcc gcgccattga agcaggccgt gtttggacca attgctatca tatctatccg 1380
gcccatgcag catttggtgg ttataaaaaa tcaggtgttg gtcgtgaaaa tcataaaatg 1440
atgctggatc attaccagca gaccaaaaat ctgctggtta gctatagtac caaagccatg 1500
ggtttctttt aa 1512

<210> SEQ ID NO 58
<211> LENGTH: 1590
<212> TYPE: DNA
<213> ORGANISM: Yarrowia lipolytica

<400> SEQUENCE: 58
atgaccacca ccgccaccga aaccccgacc accaatgtga ccccgaccac aagtctgccg 60
aaagaaaccg caagtccggg cggcaccgca agcgttaata ccagctttga ttgggaaagt 120
atttgcggta aaaccccgct ggaagaaatt gaaagtgata ttagccgtct gaaaaagact 180
tttcgtagcg gtaaaaccct ggatctggat tatcgcctgg atcagattcg caatctggca 240
tacgctattc gtgataatga aaataagatc cgtgatgcca ttaaggcaga tttgaaacgc 300
ccggattttg aaaccatggc agccgaattt tctgtgcaga tgggcgagtt taattatgtt 360
gttaaaaacc tgccgaagtg ggtgaaagat gaaaaagtta aaggtacaag catggcatat 420
tggaatagca gtccgaaaat tcgtaaacgc ccgctgggca gtgttctggt tattaccccg 480
tggaattatc cgctgattct ggccgtgagc ccggttctgg gcgcaattgc cgcaggcaat 540
accgttgcac tgaaaatgag tgaaatgagt ccgaatgcca gcaaagttat tggtgacatt 600
atgaccgccg ccctggaccc tcagctgttt cagtgctttt tcggtggcgt gccggaaacc 660
accgaaattc tgaaacatcg ttgggataaa attatgtata ccggtaatgg taaagtgggt 720
cgtattattt gcgaagccgc aaataagtat ctgaccccgg ttgaactgga actgggcggt 780
aaaagcccgg tgtttgttac caaacattgc agcaatctgg aaatggcagc acgccgtatt 840
atttggggca aatttgttaa tggcggccag acctgtgttg ccccggatta tgtgctggtt 900
tgcccggaag ttcatgataa atttgttgca gcctgtcaga aagttctgga taaattttat 960
ccgaataaca gtgccgaaag tgaaatggcc catattgcaa ccccgctgca ttatgaacgt 1020
ctgaccggtc tgctgaatag cacccgcggc aaagtggtgg ccggcggtac attcaatagc 1080
gccacccgtt ttattgcacc gaccattgtt gatggtgtgg atgcaaatga tagtctgatg 1140
cagggtgaac tgtttggtcc gctgctgccg attgttaaag caatgagtac cgaagcagca 1200
tgtaattttg tgctggaaca tcatccgacc ccgctggcag aatatatttt tagcgataat 1260
aacagcgaga tcgattatat tcgtgatcgc gttagcagcg gcggtctggt tattaatgat 1320
accctgattc atgttggctg tgttcaggcc ccgtttggcg gtgtgggtga cagtggcaat 1380
ggtggttatc atggtaaaca tacctttgat ctgtttagtc atagtcagac cgttctgcgt 1440
cagccgggtt gggtggaaat gctgcagaaa aaacgttatc cgccgtataa taagagcaat 1500
gaaaaatttg tgcgccgcat ggttgtgccg agtccgggct ttccgcgcga aggtgacgtt 1560
cgtggctttt ggagccgcct gtttaattaa 1590

<210> SEQ ID NO 59
<211> LENGTH: 503
<212> TYPE: PRT
<213> ORGANISM: Acinetobacter sp. strain M1

<400> SEQUENCE: 59

Met His Tyr Val Asp Pro Asn Gln Ser Gly Ser Lys Ile His Phe Lys
1               5                   10                  15

Asp Gln Tyr Glu Asn Phe Ile Gly Gly Gln Trp Val Ala Pro Val Lys
            20                  25                  30

Gly Val Tyr Phe Asp Asn Ile Ser Pro Val Asp Gly Lys Ser Phe Thr
        35                  40                  45

Arg Ile Pro Arg Ser Ser Ala Glu Asp Ile Glu Leu Ala Leu Asp Ala
    50                  55                  60

Ala His Lys Ala Lys Lys Glu Trp Asn Lys Ser Ser Pro Thr Thr Arg
65                  70                  75                  80

Ser Asn Leu Leu Leu Lys Ile Ala Asp Arg Met Glu Ala Asn Leu Glu
                85                  90                  95

Met Leu Ala Val Ala Glu Thr Trp Asp Asn Gly Lys Pro Val Arg Glu
            100                 105                 110

Thr Leu Ala Ala Asp Ile Pro Leu Ala Ile Asp His Phe Arg Tyr Phe
        115                 120                 125

Ala Gly Cys Ile Arg Ala Gln Glu Gly Gly Ile Ser Glu Ile Asp Glu
    130                 135                 140

Asp Thr Ile Ala Tyr His Phe His Glu Pro Leu Gly Val Val Gly Gln
145                 150                 155                 160

Ile Ile Pro Trp Asn Phe Pro Ile Leu Met Ala Ala Trp Lys Leu Ala
                165                 170                 175

Pro Ala Leu Ala Ala Gly Asn Cys Val Val Ile Lys Pro Ala Glu Gln
            180                 185                 190

Thr Pro Val Gly Ile Leu Leu Val Ala Glu Leu Ile Gln Asp Leu Leu
        195                 200                 205

Pro Ala Gly Val Leu Asn Ile Val Asn Gly Tyr Gly Ala Glu Val Gly
    210                 215                 220

Arg Pro Leu Ala Thr Ser Pro Arg Ile Ala Lys Ile Ala Phe Thr Gly
225                 230                 235                 240

Ser Thr Gln Val Gly Gln Leu Ile Met Gln Tyr Ala Thr Glu Asn Ile
                245                 250                 255

Ile Pro Val Thr Leu Glu Leu Gly Gly Lys Ser Pro Asn Val Phe Phe
            260                 265                 270

Ala Asp Val Met Asp His Asp Asp Asp Phe Leu Asp Lys Thr Leu Glu
        275                 280                 285

Gly Phe Ala Met Phe Ala Leu Asn Gln Gly Glu Val Cys Thr Cys Pro
    290                 295                 300

Ser Arg Ala Leu Ile Gln Glu Ser Ile Ala Asp Gln Phe Met Glu Lys
305                 310                 315                 320

Ala Ile Glu Arg Val Lys Arg Ile Lys Leu Gly His Pro Leu Asp Thr
                325                 330                 335

Asp Thr Met Val Gly Ala Gln Ala Ser Leu Glu Gln Gln Glu Lys Ile
            340                 345                 350

Leu Arg Cys Ile Asp Thr Gly Arg Gln Glu Gly Ala Glu Val Leu Leu
        355                 360                 365

Gly Gly His Gly Arg Gln Glu Val Gly Asn Gly Tyr Tyr Ile Glu Pro
    370                 375                 380

Thr Ile Phe Lys Gly His Asn Asn Met Gln Val Phe Gln Glu Glu Ile
385                 390                 395                 400

Phe Gly Pro Val Leu Ser Val Thr Thr Phe Lys Asp Phe Asp Glu Ala
                405                 410                 415

Ile Gln Ile Ala Asn Asp Thr Met Tyr Gly Leu Gly Ala Gly Val Trp
420 425 430

Ser Arg Ser Thr His Thr Ala Tyr Arg Ala Gly Arg Ala Ile Glu Ala
435 440 445

Gly Arg Val Trp Thr Asn Cys Tyr His Ile Tyr Pro Ala His Ala Ala
450 455 460

Phe Gly Gly Tyr Lys Lys Ser Gly Val Gly Arg Glu Asn His Lys Met
465 470 475 480

Met Leu Asp His Tyr Gln Gln Thr Lys Asn Leu Leu Val Ser Tyr Ser
485 490 495

Thr Lys Ala Met Gly Phe Phe
500

<210> SEQ ID NO 60
<211> LENGTH: 529
<212> TYPE: PRT
<213> ORGANISM: Yarrowia lipolytica

<400> SEQUENCE: 60

Met Thr Thr Thr Ala Thr Glu Thr Pro Thr Thr Asn Val Thr Pro Thr
1 5 10 15

Thr Ser Leu Pro Lys Glu Thr Ala Ser Pro Gly Gly Thr Ala Ser Val
20 25 30

Asn Thr Ser Phe Asp Trp Glu Ser Ile Cys Gly Lys Thr Pro Leu Glu
35 40 45

Glu Ile Glu Ser Asp Ile Ser Arg Leu Lys Lys Thr Phe Arg Ser Gly
50 55 60

Lys Thr Leu Asp Leu Asp Tyr Arg Leu Asp Gln Ile Arg Asn Leu Ala
65 70 75 80

Tyr Ala Ile Arg Asp Asn Glu Asn Lys Ile Arg Asp Ala Ile Lys Ala
85 90 95

Asp Leu Lys Arg Pro Asp Phe Glu Thr Met Ala Ala Glu Phe Ser Val
100 105 110

Gln Met Gly Glu Phe Asn Tyr Val Val Lys Asn Leu Pro Lys Trp Val
115 120 125

Lys Asp Glu Lys Val Lys Gly Thr Ser Met Ala Tyr Trp Asn Ser Ser
130 135 140

Pro Lys Ile Arg Lys Arg Pro Leu Gly Ser Val Leu Val Ile Thr Pro
145 150 155 160

Trp Asn Tyr Pro Leu Ile Leu Ala Val Ser Pro Val Leu Gly Ala Ile
165 170 175

Ala Ala Gly Asn Thr Val Ala Leu Lys Met Ser Glu Met Ser Pro Asn
180 185 190

Ala Ser Lys Val Ile Gly Asp Ile Met Thr Ala Ala Leu Asp Pro Gln
195 200 205

Leu Phe Gln Cys Phe Phe Gly Gly Val Pro Glu Thr Thr Glu Ile Leu
210 215 220

Lys His Arg Trp Asp Lys Ile Met Tyr Thr Gly Asn Gly Lys Val Gly
225 230 235 240

Arg Ile Ile Cys Glu Ala Ala Asn Lys Tyr Leu Thr Pro Val Glu Leu
245 250 255

Glu Leu Gly Gly Lys Ser Pro Val Phe Val Thr Lys His Cys Ser Asn
260 265 270

```
Leu Glu Met Ala Ala Arg Arg Ile Ile Trp Gly Lys Phe Val Asn Gly
        275                 280                 285

Gly Gln Thr Cys Val Ala Pro Asp Tyr Val Leu Val Cys Pro Glu Val
    290                 295                 300

His Asp Lys Phe Val Ala Ala Cys Gln Lys Val Leu Asp Lys Phe Tyr
305                 310                 315                 320

Pro Asn Asn Ser Ala Glu Ser Glu Met Ala His Ile Ala Thr Pro Leu
                325                 330                 335

His Tyr Glu Arg Leu Thr Gly Leu Leu Asn Ser Thr Arg Gly Lys Val
            340                 345                 350

Val Ala Gly Gly Thr Phe Asn Ser Ala Thr Arg Phe Ile Ala Pro Thr
        355                 360                 365

Ile Val Asp Gly Val Asp Ala Asn Asp Ser Leu Met Gln Gly Glu Leu
    370                 375                 380

Phe Gly Pro Leu Leu Pro Ile Val Lys Ala Met Ser Thr Glu Ala Ala
385                 390                 395                 400

Cys Asn Phe Val Leu Glu His His Pro Thr Pro Leu Ala Glu Tyr Ile
                405                 410                 415

Phe Ser Asp Asn Asn Ser Glu Ile Asp Tyr Ile Arg Asp Arg Val Ser
            420                 425                 430

Ser Gly Gly Leu Val Ile Asn Asp Thr Leu Ile His Val Gly Cys Val
        435                 440                 445

Gln Ala Pro Phe Gly Gly Val Gly Asp Ser Gly Asn Gly Gly Tyr His
    450                 455                 460

Gly Lys His Thr Phe Asp Leu Phe Ser His Ser Gln Thr Val Leu Arg
465                 470                 475                 480

Gln Pro Gly Trp Val Glu Met Leu Gln Lys Lys Arg Tyr Pro Pro Tyr
                485                 490                 495

Asn Lys Ser Asn Glu Lys Phe Val Arg Arg Met Val Val Pro Ser Pro
            500                 505                 510

Gly Phe Pro Arg Glu Gly Asp Val Arg Gly Phe Trp Ser Arg Leu Phe
        515                 520                 525

Asn
```

<210> SEQ ID NO 61
<211> LENGTH: 1359
<212> TYPE: DNA
<213> ORGANISM: Lactobacillus sanfranciscensis

<400> SEQUENCE: 61

```
atgaaagtta ttgtagtagg ttgtactcac gctggcactt ttgcagttaa gcaaacgatt     60

gccgatcacc ccgatgcaga tgtgactgta tatgaaatga atgataacat ttccttttta    120

tcatgtggaa tcgcccttta cttaggtaaa gaaattaaaa acaatgatcc ccgagggctt    180

ttctactcaa gtccagaaga attaagcaat cttggagcta acgtccaaat gcgtcatcaa    240

gttacaaacg ttgatccaga aacaaaaaca atcaaagtta aagatttaat caccaacgaa    300

gaaaaaacag aagcatatga caaattaatt atgaccactg gttctaagcc tactgttcct    360

ccaatccctg gaatcgatag tagtcgcgtt tacctttgta aaaactataa cgatgctaaa    420

aagttatttg aagaagctcc caaagctaaa acgattacta tcattggttc tggttatatt    480

ggtgccgaac tggctgaagc ctactcaaac caaaattata acgttaattt aattgatggt    540

catgaacgag ttctttacaa gtattttgat aaagaattta ctgatatttt agccaaagat    600
```

```
tatgaagctc atggtgttaa cctggttctt ggttcaaaag tagctgcttt tgaagaagtc    660

gatgatgaaa ttatcactaa aaccctagat ggtaaagaaa ttaaatctga tattgcaatt    720

ctttgtatcg gtttccgccc taacactgaa ttacttaaag gtaaagttgc catgttggat    780

aacggtgcaa tcattactga tgaatacatg cattcatcaa atcgcgacat ttttgctgct    840

ggtgatagtg ccgccgttca ctacaacccc actaattcta acgcctacat tcctttagct    900

accaacgccg tacgccaagg gagattagtt ggcctaaatc tgactgaaga caaagtaaaa    960

gacatgggaa cccaatcttc atctggtctt aaactatacg gtcggactta tgtctcaact   1020

ggaatcaata cggctcttgc taaagccaat aatttaaaag ttagcgaagt aatcatagct   1080

gataattatc gtccagaatt tatgttatca acggatgaag ttttaatgtc attagtgtat   1140

gatcctaaga ctcgtgtaat tttgggaggg gcgctttcaa gtatgcacga tgtttcgcaa   1200

tcagcgaacg tcttatcagt atgtattcaa aataaaaaca cgattgacga tttagcaatg   1260

gtggatatgt tattccaacc acaatttgat cgtccgttta actacttaaa cattctaggc   1320

caagctgctc aagcacaagc tgacaaagca cataaataa                          1359
```

<210> SEQ ID NO 62
<211> LENGTH: 452
<212> TYPE: PRT
<213> ORGANISM: Lactobacillus sanfranciscensis

<400> SEQUENCE: 62

```
Met Lys Val Ile Val Val Gly Cys Thr His Ala Gly Thr Phe Ala Val
1               5                   10                  15

Lys Gln Thr Ile Ala Asp His Pro Asp Ala Asp Val Thr Val Tyr Glu
            20                  25                  30

Met Asn Asp Asn Ile Ser Phe Leu Ser Cys Gly Ile Ala Leu Tyr Leu
        35                  40                  45

Gly Lys Glu Ile Lys Asn Asn Asp Pro Arg Gly Leu Phe Tyr Ser Ser
    50                  55                  60

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
                85                  90                  95

Ile Thr Asn Glu Glu Lys Thr Glu Ala Tyr Asp Lys Leu Ile Met Thr
            100                 105                 110

Thr Gly Ser Lys Pro Thr Val Pro Pro Ile Pro Gly Ile Asp Ser Ser
        115                 120                 125

Arg Val Tyr Leu Cys Lys Asn Tyr Asn Asp Ala Lys Lys Leu Phe Glu
    130                 135                 140

Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
                165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
        195                 200                 205

Val Leu Gly Ser Lys Val Ala Ala Phe Glu Glu Val Asp Asp Glu Ile
    210                 215                 220

Ile Thr Lys Thr Leu Asp Gly Lys Glu Ile Lys Ser Asp Ile Ala Ile
225                 230                 235                 240
```

```
Leu Cys Ile Gly Phe Arg Pro Asn Thr Glu Leu Leu Lys Gly Lys Val
            245                 250                 255

Ala Met Leu Asp Asn Gly Ala Ile Ile Thr Asp Glu Tyr Met His Ser
            260                 265                 270

Ser Asn Arg Asp Ile Phe Ala Ala Gly Asp Ser Ala Ala Val His Tyr
        275                 280                 285

Asn Pro Thr Asn Ser Asn Ala Tyr Ile Pro Leu Ala Thr Asn Ala Val
    290                 295                 300

Arg Gln Gly Arg Leu Val Gly Leu Asn Leu Thr Glu Asp Lys Val Lys
305                 310                 315                 320

Asp Met Gly Thr Gln Ser Ser Ser Gly Leu Lys Leu Tyr Gly Arg Thr
            325                 330                 335

Tyr Val Ser Thr Gly Ile Asn Thr Ala Leu Ala Lys Ala Asn Asn Leu
            340                 345                 350

Lys Val Ser Glu Val Ile Ile Ala Asp Asn Tyr Arg Pro Glu Phe Met
        355                 360                 365

Leu Ser Thr Asp Glu Val Leu Met Ser Leu Val Tyr Asp Pro Lys Thr
    370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
            405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
        435                 440                 445

Lys Ala His Lys
    450
```

<210> SEQ ID NO 63
<211> LENGTH: 1356
<212> TYPE: DNA
<213> ORGANISM: Lactobacillus brevis

<400> SEQUENCE: 63

```
atgaaagtga ccgtggtggg ctgcacccat gcgggcacct ttgcgattaa acagattctg     60

gcggaacatc cggatgcgga agtgaccgtg tatgaaaaaa acgataacat tagctttctg    120

agctgcggca ttgcgctgta tctgggcggc aaagtggcgg atccgcaggg cctgttttat    180

agcagcccgg aagaactgaa aagcctgggc gcgaacgtgc agatgaacca taacgtgctg    240

aacattgatc cggatcagaa aaccgtgacc gtggaaaaca tgaacaccca tgaacagacc    300

accgcggatt atgataaact ggtgatgacc agcggcagct ggccgattgt gccgaaaatt    360

ccgggcattg atggcgatca tgtgaaactg tgcaaaaact ggaaccatgc gcagaccctg    420

attgaagatg cgaaaagcgc gaaacatatt accgtgattg gcgcgggcta tattggcgcg    480

gaactggcgg aagcgtatag caccaccggc catgatgtga ccctgattga tgcgatggat    540

cgcgtgatgc cgaaatattt tgatagcgaa tttaccgatg tgattgaaca ggattatcgc    600

gataacaacg tgcagctggc gctgggcgaa accgtgcaga gctttaccga taccggcgat    660

ggcgtgacca ttaaaaccga taaaggcagc tatgatacca acctggcgat tctgtgcatt    720

ggctttcgcc cgaacaccgg cctgctgaaa ggcaaagtgg atatggcgaa aaacggcgcg    780

attattaccg atgattatat gcgcagcagc aacccggata tttttgcggc gggcgatagc    840

gcggcggtgc attataaccc gacccatcag aacgcgtata ttccgctggc gaccaacgcg    900
```

```
gtgcgccagg gcattctggt gggcaaaaac ctggtgaaac cgaccgtgaa atatatgggc    960

acccagagca gcagcggcct ggcgctgtat gatcgcacca ttgtgagcac cggcctgacc   1020

ctggcggcgg cgaaacagca gggcattaac gcggaacagg tgattgtgaa agataactat   1080

cgcccggaat ttatgccgac caccgaaccg gtgctgatga gcctggtgtt tgatccggat   1140

agccgccgca ttctgggcgg cgcgctgatg agccgctatg atgtgagcca gagcgcgaac   1200

accctgagcg tgtgcattca gaacgaaaac accattgatg atctggcgat ggtggatatg   1260

ctgtttcagc cgaactttga tcgcccgttt aactatctga acattctggc gcaggcggcg   1320

caggaaaaag tggcgaaatt tcagccggcg gaataa                             1356
```

```
<210> SEQ ID NO 64
<211> LENGTH: 451
<212> TYPE: PRT
<213> ORGANISM: Lactobacillus brevis

<400> SEQUENCE: 64

Met Lys Val Thr Val Val Gly Cys Thr His Ala Gly Thr Phe Ala Ile
1               5                   10                  15

Lys Gln Ile Leu Ala Glu His Pro Asp Ala Glu Val Thr Val Tyr Glu
            20                  25                  30

Lys Asn Asp Asn Ile Ser Phe Leu Ser Cys Gly Ile Ala Leu Tyr Leu
        35                  40                  45

Gly Gly Lys Val Ala Asp Pro Gln Gly Leu Phe Tyr Ser Ser Pro Glu
    50                  55                  60

Glu Leu Lys Ser Leu Gly Ala Asn Val Gln Met Asn His Asn Val Leu
65                  70                  75                  80

Asn Ile Asp Pro Asp Gln Lys Thr Val Thr Val Glu Asn Met Asn Thr
                85                  90                  95

His Glu Gln Thr Thr Ala Asp Tyr Asp Lys Leu Val Met Thr Ser Gly
            100                 105                 110

Ser Trp Pro Ile Val Pro Lys Ile Pro Gly Ile Asp Gly Asp His Val
        115                 120                 125

Lys Leu Cys Lys Asn Trp Asn His Ala Gln Thr Leu Ile Glu Asp Ala
    130                 135                 140

Lys Ser Ala Lys His Ile Thr Val Ile Gly Ala Gly Tyr Ile Gly Ala
145                 150                 155                 160

Glu Leu Ala Glu Ala Tyr Ser Thr Thr Gly His Asp Val Thr Leu Ile
                165                 170                 175

Asp Ala Met Asp Arg Val Met Pro Lys Tyr Phe Asp Ser Glu Phe Thr
            180                 185                 190

Asp Val Ile Glu Gln Asp Tyr Arg Asp Asn Asn Val Gln Leu Ala Leu
        195                 200                 205

Gly Glu Thr Val Gln Ser Phe Thr Asp Thr Gly Asp Gly Val Thr Ile
    210                 215                 220

Lys Thr Asp Lys Gly Ser Tyr Asp Thr Asn Leu Ala Ile Leu Cys Ile
225                 230                 235                 240

Gly Phe Arg Pro Asn Thr Gly Leu Leu Lys Gly Lys Val Asp Met Ala
                245                 250                 255

Lys Asn Gly Ala Ile Ile Thr Asp Asp Tyr Met Arg Ser Ser Asn Pro
            260                 265                 270

Asp Ile Phe Ala Ala Gly Asp Ser Ala Ala Val His Tyr Asn Pro Thr
        275                 280                 285
```

-continued

```
His Gln Asn Ala Tyr Ile Pro Leu Ala Thr Asn Ala Val Arg Gln Gly
    290                 295                 300

Ile Leu Val Gly Lys Asn Leu Val Lys Pro Thr Val Lys Tyr Met Gly
305                 310                 315                 320

Thr Gln Ser Ser Ser Gly Leu Ala Leu Tyr Asp Arg Thr Ile Val Ser
                325                 330                 335

Thr Gly Leu Thr Leu Ala Ala Ala Lys Gln Gln Gly Ile Asn Ala Glu
            340                 345                 350

Gln Val Ile Val Lys Asp Asn Tyr Arg Pro Glu Phe Met Pro Thr Thr
        355                 360                 365

Glu Pro Val Leu Met Ser Leu Val Phe Asp Pro Asp Ser Arg Arg Ile
    370                 375                 380

Leu Gly Gly Ala Leu Met Ser Arg Tyr Asp Val Ser Gln Ser Ala Asn
385                 390                 395                 400

Thr Leu Ser Val Cys Ile Gln Asn Glu Asn Thr Ile Asp Asp Leu Ala
                405                 410                 415

Met Val Asp Met Leu Phe Gln Pro Asn Phe Asp Arg Pro Phe Asn Tyr
            420                 425                 430

Leu Asn Ile Leu Ala Gln Ala Ala Gln Glu Lys Val Ala Lys Phe Gln
        435                 440                 445

Pro Ala Glu
    450
```